US011384141B2

(12) United States Patent
Hussack et al.

(10) Patent No.: US 11,384,141 B2
(45) Date of Patent: Jul. 12, 2022

(54) SERUM ALBUMIN BINDING ANTIBODIES FOR TUNEABLE HALF-LIFE EXTENSION OF BIOLOGICS

(71) Applicant: National Research Council of Canada, Ottawa (CA)

(72) Inventors: Gregory Hussack, Ottawa (CA); Jamshid Tanha, Orleans (CA); Kevin Henry, Ottawa (CA); Traian Sulea, Kirkland (CA)

(73) Assignee: NATIONAL RESEARCH COUNCIL OF CANADA, Ottawa (CA)

( * ) Notice: Subject to any disclaimer, the term of this patent is extended or adjusted under 35 U.S.C. 154(b) by 0 days.

(21) Appl. No.: 17/050,072

(22) PCT Filed: Apr. 24, 2019

(86) PCT No.: PCT/CA2019/050514
§ 371 (c)(1),
(2) Date: Oct. 23, 2020

(87) PCT Pub. No.: WO2019/204925
PCT Pub. Date: Oct. 31, 2019

(65) Prior Publication Data
US 2021/0253679 A1 Aug. 19, 2021

Related U.S. Application Data

(60) Provisional application No. 62/661,871, filed on Apr. 24, 2018.

(51) Int. Cl.
*C07K 16/18* (2006.01)
(52) U.S. Cl.
CPC .......... *C07K 16/18* (2013.01); *C07K 2317/24* (2013.01); *C07K 2317/565* (2013.01); *C07K 2317/569* (2013.01)
(58) Field of Classification Search
None
See application file for complete search history.

(56) References Cited

U.S. PATENT DOCUMENTS

2007/0269422 A1   11/2007   Beirnaert et al.

FOREIGN PATENT DOCUMENTS

WO    WO2010094722 A2    8/2010

OTHER PUBLICATIONS

Henry, K.A., et al.; Identification of cross-reactive single-domain antibodies against serum albumin using next-generation DNA sequencing. Protein Eng. Des. Sel. Oct. 2015, vol. 28, No. 10, pp. 379-383, ISSN 1741-0126.

Van Roy, M. et al.; The preclinical pharmacology of the high affinity anti-IL-6R Nanobody ALX-0061 supports its clinical development in rheumatoid arthritis. Arthritis Res. Ther. May 20, 2015, vol. 17:135, ISSN 1478-6362.
International Search Report of PCT/CA2019/050514; dated Jul. 8, 2019; Tan, Ernest.
Arbabi-Ghahroudi M et al., Selection and identification of single domain antibody fragments from camel heavy-chain antibodies, (1997) FEBS Lett 414:521-6.
Baral TN et al., (2013) Single-Domain Antibodies and Their Utility, Curr Protoc Immunol 103: pp. 2.17.
Bell, A., Wang, Z.J., Arbabi-Ghahroudi, M., Chang, T.A., Durocher, Y., Trojahn, U., Baardsnes, J., Jaramillo, M.L., Li, S., Baral, T.N., O'Connor-McCourt, M., MacKenzie, R., Zhang, J. (2010) Cancer Lett 289:81-90.
Chakravarthy B et al. (2014) Evidence that a synthetic amyloid-β oligomer-binding peptide (ABP) targets amyloid-β deposits in transgenic mouse brain and human Alzheimer's disease brain, Biochem Biophys Res Commun 445:656-60.
Chothia, C. et al. (1987), Canonical Structures for the Hypervariable Regions of Immunoglobulins, J. Mol. Biol. 196, 901-917.
Davies J et al., (1996) Affinity improvement of single antibody VH domains: residues in all three hypervariable regions affect antigen binding, Immunotechnology 2:169-79.
De Kruif, J. et al., Leucine Zipper Dimerized Bivalent and Bispecific scFv Antibodies from a Semi-Synthetic Antibody Phage Display Library (1996) J. Biol. Chem. 271, 7630-7634.
Dumoulin M et al. (2002) Single-domain antibody fragments with high conformational stability, Protein Sci 11:500-15.
Coppieters K et al., Formatted anti-tumor necrosis factor alpha VHH proteins derived from camelids show superior potency and targeting to inflamed joints in a murine model of collagen-induced arthritis. Arthritis Rheum. Jun. 2006;54 (6):1856-66. doi: 10.1002/art.21827. PMID: 16736523.
Durocher Y et al. (2002) High-level and high-throughput recombinant protein production by transient transfection of suspension-growing human 293-EBNA1 cells, Nucleic Acids Res 30(2):E9.
Hamers-Casterman, C. et al., Naturally Occurring Antibodies Devoid of Light Chains; (1993) Nature 363, 446-448.
Haqqani AS et al. (2013) Multiplexed Evaluation of Serum and CSF Pharmacokinetics of Brain-Targeting SingleDomain Antibodies Using a NanoLC-SRM-ILIS Method, Mol Pharm 10:1542-56.
Holt LJ et al., Anti-serum albumin domain antibodies for extending the half-lives of short lived drugs. Protein Eng Des Sel. May 2008;21(5):283-8. doi: 10.1093/protein/gzm067. Epub Apr. 2, 2008. PMID: 18387938.
Igawa T , et al., pH-dependent antigen-binding antibodies as a novel therapeutic modality. Biochim Biophys Acta. Nov. 2014;1844(11):1943-1950. doi: 10.1016/j.bbapap.2014.08.003. Epub Aug. 12, 2014. PMID: 25125373.

(Continued)

*Primary Examiner* — Adam Weidner
(74) *Attorney, Agent, or Firm* — Benoît & Côté, Inc.; Mathieu Miron

(57) ABSTRACT

The present document describes an antibody or an antigen-binding fragment that bind to serum albumin comprising three complementarity determining regions (CDR1, CDR2 and CDR3), for half-life extension of biologics. The present invention also relates to pharmaceutical compositions, nucleic acid vectors, cells comprising the nucleic acid vectors, and methods of removing molecules from serum.

20 Claims, 16 Drawing Sheets

Specification includes a Sequence Listing.

(56) References Cited

OTHER PUBLICATIONS

Iqbal, U. et al., Kinetic Analysis of Novel Mono- and Multivalent VHH-fragments and Their Application for Molecular Imaging of Brain Tumours (2010) Br. J. Pharmacol. 160, 1016-1028.

Jespers L et al. (2004) Crystal Structure of HEL4, a Soluble, Refoldable Human VH Single Domain with a Germ-line Scaffold, J Mol Biol 337:893-903.

Jevsevar S et al., PEGylation of therapeutic proteins. Biotechnol J. Jan. 2010;5(1):113-28. doi: 10.1002/biot.200900218 PMID: 20069580.

Kabat, E.A., Identical V Region Amino Acid Sequences and Segments of Sequences in Antibodies of Different Specificities; (1991) J. Immunol. 147:1709-19.

Kim DY et al. (2012) Disulfide linkage engineering for improving biophysical properties of human VH domains, Protein Eng Des Sel 25:581-9.

Kontermann RE, Strategies for extended serum half-life of protein therapeutics. Curr Opin Biotechnol. Dec. 2011;22 (6):868-76. doi: 10.1016/j.copbio.2011.06.012. Epub Aug. 20, 2011. PMID: 21862310.

Li S et al. (2009) Pentabody-mediated antigen delivery induces antigen-specific mucosal immune response, Mol Immunol 46:1718-26.

Magoč T et al. (2011) FLASH: fast length adjustment of short reads to improve genome assemblies, Bioinformatics 27:2957-63.

Merritt EA et al. (1995) AB5 toxins, Curr Opin Struct Biol 5:165-71.

Müller MR et al., Improving the pharmacokinetic properties of biologies by fusion to an anti-HSA shark VNAR domain. MAbs. Nov.-Dec. 2012;4(6):673-85. doi: 10.4161/mabs.22242. PMID: 23676205; PMCID: PMC3502234.

Murase, T., Eugenio, L., Schorr, M., Hussack, G., Tanha, J., Kitova, E.N., Klassen, J.S., Ng, K.K. (2014) J Biol Chem 289:2331-43.

Muruganandam A et al. (2002) Selection of phage-displayed llama single-domain antibodies that transmigrate across human blood-brain barrier endothelium, FASEB J 16:240-2.

Nicaise M et al. (2004) Affinity transfer by CDR grafting on a nonimmunoglobulin scaffold, Protein Sci 13:1882-91.

Nielsen UB et al. (2000) Targeting of Bivalent Anti-ErbB2 Diabody Antibody Fragments to Tumor Cells Is Independent of the Intrinsic Antibody Affinity, Cancer Res 60:6434-40.

Nuttall, S.D. et al., Isolation and Characterization of an IgNAR Variable Domain Specific for the Human Mitochondrial Translocase Receptor Tom70; (2003) Eur. J. Biochem. 270, 3543-3554.

Ridgway, J.B. et al., Knobs-Into-Holes Engineering of Antibody CH3 Domains for Heavy Chain Heterodimerization (1996) Protein Eng. 9, 617-621.

Schmieder R et al. (2011) Quality control and preprocessing of metagenomic datasets, Bioinformatics 27:863-4.

Sleep D et al., Albumin as a versatile platform for drug half-life extension. Biochim Biophys Acta. Dec. 2013; 1830 (12):5526-34. doi: 10.1016/j.bbagen.2013.04.023. Epub Apr. 29, 2013. PMID: 23639804.

Spiess C et al. (2015) Alternative molecular formats and therapeutic applications for bispecific antibodies, Mol Immunol 67:95-106.

Strohl WR, Fusion Proteins for Half-Life Extension of Biologies as a Strategy to Make Biobetters. BioDrugs. Aug. 2015;29(4):215-39. doi: 10.1007/S40259-015-0133-6. PMID: 26177629; PMCID: PMC4562006.

To R et al. (2005) Isolation of Monomeric Human VHS by a Phage Selection, J Biol Chem 280:41395-41403.

Walker A et al., Anti-serum albumin domain antibodies in the development of highly potent, efficacious and long-acting interferon. Protein Eng Des Sel. Apr. 2010;23(4):271-8. doi: 10.1093/protein/gzp091. Epub Jan. 21, 2010. PMID: 20093262.

Zhang, J. et al., The Pentavalent Single-Domain Antibody Approach to Tumor Antigen Discovery and the Development of Novel Proteomics Reagents (2004a) J. Mol. Biol. 341, 161-169.

Zhang J. et al., Pentamerization of Single-Domain Antibodies from Phage Libraries: A Novel Strategy for the Rapid Generation of High-Avidity Antibody Reagents; (2004b) J. Mol. Biol 335, 49-56.

Zhang Y et al. (2010) PKSolver: An add-in program for pharmacokinetic and pharmacodynamic data analysis in Microsoft Excel, Comput Methods Programs Biomed 99:306-14.

Zhu X et al. (2010) COMBODY: one-domain antibody multimer with improved avidity, Immunol Cell Biol 88:667-75.

Hussack, G. et al., Neutralization of Clostridium difficile Toxin A with Single-domain Antibodies Targeting the Cell Receptor Binding Domain (2011) J. Biol. Chem. 286, 8961-8976.

Hussack G et al., (2011b) Engineered Single-Domain Antibodies with High Protease Resistance and Thermal Stability, PLoS One 6(11):e28218.

Supplementary European Search Report of EP19792286.7; Le Flao, Katell; dated Jan. 4, 2022; The Hague.

| | | FR1 | CDR1 | FR2 | CDR2 | FR3 | CDR3 | FR4 |
|---|---|---|---|---|---|---|---|---|
| A | R11 | QVKLEESGGGLVQAGGSLRLSCVGPGFLLRSNTMGWYRQAPGKERELVAFIR | -- | PSGLTNYNDAVQGRFTISRDNAKNTVYLQMNALKPEDTAVYYCHTRPPFQR | ------- | DSWGQGTQVTVSS | | |
| | R11-H0 | EVQLVESGGGLVQPGGSLRLSCAASGFLLRSNTMGWYRQAPGKGLEWVSFIR | -- | PSGLTNYNDAVQGRFTISRDNSKNTLYLQMNSLRAEDTAVYYCATRPPFQR | ------- | DSWGQGTLVTVSS | | |
| | R11-H1 | EVQLVESGGGLVQPGGSLRLSCAASGFLLRSNTMGWYRQAPGKGLELVSFIR | -- | PSGLTNYNDAVQGRFTISRDNSKNTLYLQMNSLRAEDTAVYYCATRPPFQR | ------- | DSWGQGTLVTVSS | | |
| | R11-H2 | EVQLVESGGGLVQPGGSLRLSCAASGFLLRSNTMGWYRQAPGKGLELVSFIR | -- | PSGLTNYNDAVQGRFTISRDNSKNTLYLQMNSLRAEDTAVYYCHTRPPFQR | ------- | DSWGQGTLVTVSS | | |
| | R11-H3 | QVQLVESGGGLVQPGGSLRLSCAASGFLLRSNTMGWYRQAPGKERELVAFIR | -- | PSGLTNYNDAVQGRFTISRDNSKNTLYLQMNSLRAEDTAVYYCHTRPPFQR | ------- | DSWGQGTLVTVSS | | |
| | R11-H4 | QVQLVESGGGLVQPGGSLRLSCAGPGFLLRSNTMGWYRQAPGKERELVAFIR | -- | PSGLTNYNDAVQGRFTISRDNSKNTLYLQMNSLRAEDTAVYYCHTRPPFQR | ------- | DSWGQGTLVTVSS | | |
| | R11-H5 | QVQLVESGGGLVQPGGSLRLSCAGPGFLLRSNTMGWYRQAPGKERELVAFIR | -- | PSGLTNYNDAVQGRFTISRDNSKNTLYLQMNSLRAEDTAVYYCHTRPPFQR | ------- | DSWGQGTLVTVSS | | |
| | R11-H6 | QVQLVESGGGLVQPGGSLRLSCAGPGFLLRSNTMGWYRQAPGKERELVAFIR | -- | PSGLTNYNDAVQGRFTISRDNAKNTVYLQMNSLRAEDTAVYYCHTRPPFQR | ------- | DSWGQGTLVTVSS | | |
| B | R28 | QVQLVESGGGLVQAGGSLRLSCVASGRTFIAYAMGWFRQAPGKEREFVAAITNFAGGTTYYADSVKGRFTISRDNAKTTVYLQMNSLKPEDTALYYCAADRSAQTMRQVRPVLPYWGQGTQVTVSS | | | | | | |
| | R28-H0 | EVQLVESGGGLVQPGGSLRLSCAASGRTFIAYAMGWVRQAPGKGLEWVSAITNFAGGTTYYADSVKGRFTISRDNSKNTLYLQMNSLRAEDTAVYYCAADRSAQTMRQVRPVLPYWGQGTLVTVSS | | | | | | |
| | R28-H1 | EVQLVESGGGLVQPGGSLRLSCAASGRTFIAYAMGWFRQAPGKGLEFVSAITNFAGGTTYYADSVKGRFTISRDNSKNTLYLQMNSLRAEDTAVYYCAADRSAQTMRQVRPVLPYWGQGTLVTVSS | | | | | | |
| | R28-H2 | EVQLVESGGGLVQPGGSLRLSCAASGRTFIAYAMGWFRQAPGKEREFVSAITNFAGGTTYYADSVKGRFTISRDNSKNTLYLQMNSLRAEDTAVYYCAADRSAQTMRQVRPVLPYWGQGTLVTVSS | | | | | | |
| | R28-H3 | QVQLVESGGGLVQPGGSLRLSCAASGRTFIAYAMGWFRQAPGKEREFVAAITNFAGGTTYYADSVKGRFTISRDNSKNTLYLQMNSLRAEDTAVYYCAADRSAQTMRQVRPVLPYWGQGTLVTVSS | | | | | | |
| | R28-H4 | QVQLVESGGGLVQPGGSLRLSCAASGRTFIAYAMGWFRQAPGKEREFVAAITNFAGGTTYYADSVKGRFTISRDNAKTTLYLQMNSLRAEDTAVYYCAADRSAQTMRQVRPVLPYWGQGTLVTVSS | | | | | | |
| | R28-H5 | QVQLVESGGGLVQPGGSLRLSCAASGRTFIAYAMGWFRQAPGKEREFVAAITNFAGGTTYYADSVKGRFTISRDNAKTTVYLQMNSLRAEDTAVYYCAADRSAQTMRQVRPVLPYWGQGTLVTVSS | | | | | | |
| C | M75 | QVQLVESGGGFVQAGGSLRLSCAASGRTFDNYVMAWFRQAPGKEREFVASISG | - | SGSITNYANSVKDRFTISRDSAKNAIYLQMNSLKPEDTALYYCAAGSRATYYREPKF | - | YPSWGQGTQVTVSS | | |
| | M75-H0 | EVQLVESGGGLVQPGGSLRLSCAASGRTFDNYVMAWVRQAPGKGLEWVSSISG | - | SGSITNYANSVKDRFTISRDNSKNTLYLQMNSLRAEDTAVYYCAAGSRATYYREPKF | - | YPSWGQGTLVTVSS | | |
| | M75-H1 | EVQLVESGGGLVQPGGSLRLSCAASGRTFDNYVMAWFRQAPGKGLEFVSSISG | - | SGSITNYANSVKDRFTISRDNSKNTLYLQMNSLRAEDTAVYYCAAGSRATYYREPKF | - | YPSWGQGTLVTVSS | | |
| | M75-H2 | EVQLVESGGGLVQPGGSLRLSCAASGRTFDNYVMAWFRQAPGKEREFVASISG | - | SGSITNYANSVKDRFTISRDNSKNTLYLQMNSLRAEDTAVYYCAAGSRATYYREPKF | - | YPSWGQGTLVTVSS | | |
| | M75-H3 | QVQLVESGGGLVQPGGSLRLSCAASGRTFDNYVMAWFRQAPGKEREFVASISG | - | SGSITNYANSVKDRFTISRDNSKNTLYLQMNSLRAEDTAVYYCAAGSRATYYREPKF | - | YPSWGQGTLVTVSS | | |
| | M75-H4 | QVQLVESGGGLVQPGGSLRLSCAASGRTFDNYVMAWFRQAPGKEREFVASISG | - | SGSITNYANSVKDRFTISRDSSKNALYLQMNSLRAEDTAVYYCAAGSRATYYREPKF | - | YPSWGQGTLVTVSS | | |
| | M75-H5 | QVQLVESGGGLVQPGGSLRLSCAASGRTFDNYVMAWFRQAPGKEREFVASISG | - | SGSITNYANSVKDRFTISRDSAKNAIYLQMNSLRAEDTAVYYCAAGSRATYYREPKF | - | YPSWGQGTLVTVSS | | |
| D | M79 | QVKLEESGGGLVQAGGSLRLSCAASGSTFSSSSVGWYRQAPGQQRELVAAIT | -- | SGGSTNTADSVKGRFTMSRDNAKNTVYLQMRDLKPEDTAVYYCNVAGRNWVPISRYSPGFYWGQGTQVTVSS | | | | |
| | M79-H0 | EVQLVESGGGLVQPGGSLRLSCAASGSTFSSSSVGWVRQAPGKGLEWVSAIT | -- | SGGSTNTADSVKGRFTISRDNSKNTLYLQMNSLRAEDTAVYYCAVAGRNWVPISRYSPGFYWGQGTLVTVSS | | | | |
| | M79-H1 | EVQLVESGGGLVQPGGSLRLSCAASGSTFSSSSVGWYRQAPGKGLELVSAIT | -- | SGGSTNTADSVKGRFTISRDNSKNTLYLQMNSLRAEDTAVYYCAVAGRNWVPISRYSPGFYWGQGTLVTVSS | | | | |
| | M79-H2 | EVQLVESGGGLVQPGGSLRLSCAASGSTFSSSSVGWYRQAPGKQRELVSAIT | -- | SGGSTNTADSVKGRFTISRDNSKNTLYLQMNSLRAEDTAVYYCNVAGRNWVPISRYSPGFYWGQGTLVTVSS | | | | |
| | M79-H3 | EVQLVESGGGLVQPGGSLRLSCAASGSTFSSSSVGWYRQAPGKQRELVAAIT | -- | SGGSTNTADSVKGRFTISRDNSKNTLYLQMNSLRAEDTAVYYCNVAGRNWVPISRYSPGFYWGQGTLVTVSS | | | | |
| | M79-H4 | QVQLVESGGGLVQPGGSLRLSCAASGSTFSSSSVGWYRQAPGQQRELVAAIT | -- | SGGSTNTADSVKGRFTISRDNSKNTLYLQMNSLRAEDTAVYYCNVAGRNWVPISRYSPGFYWGQGTLVTVSS | | | | |
| | M79-H5 | QVQLVESGGGLVQPGGSLRLSCAASGSTFSSSSVGWYRQAPGQQRELVAAIT | -- | SGGSTNTADSVKGRFTISRDNAKNTVYLQMNSLRAEDTAVYYCNVAGRNWVPISRYSPGFYWGQGTLVTVSS | | | | |

SEQUENCE LISTING

```
<160> NUMBER OF SEQ ID NOS: 81

<210> SEQ ID NO 1
<211> LENGTH: 9
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 1

Gly Phe Leu Leu Arg Ser Asn Thr Met
1               5

<210> SEQ ID NO 2
<211> LENGTH: 7
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 2

Ile Arg Pro Ser Gly Leu Thr
1               5

<210> SEQ ID NO 3
<211> LENGTH: 10
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 3

His Thr Arg Pro Pro Phe Gln Arg Asp Ser
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 4

Ala Thr Arg Pro Pro Phe Gln Arg Asp Ser
1               5                   10
```

```
<210> SEQ ID NO 5
<211> LENGTH: 9
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 5

Gly Arg Thr Phe Ile Ala Tyr Ala Met
1               5

<210> SEQ ID NO 6
<211> LENGTH: 9
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 6

Ile Thr Asn Phe Ala Gly Gly Thr Thr
1               5

<210> SEQ ID NO 7
<211> LENGTH: 18
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 7

Ala Ala Asp Arg Ser Ala Gln Thr Met Arg Gln Val Arg Pro Val Leu
1               5                   10                  15

Pro Tyr

<210> SEQ ID NO 8
<211> LENGTH: 9
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 8

Gly Arg Thr Phe Asp Asn Tyr Val Met
1               5

<210> SEQ ID NO 9
<211> LENGTH: 8
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 9

Ile Ser Gly Ser Gly Ser Ile Thr
1               5
```

```
<210> SEQ ID NO 10
<211> LENGTH: 17
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 10

Ala Ala Gly Ser Arg Arg Thr Tyr Tyr Arg Glu Pro Lys Phe Tyr Pro
1               5                   10                  15

Ser

<210> SEQ ID NO 11
<211> LENGTH: 9
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 11

Gly Ser Thr Phe Ser Ser Ser Ser Val
1               5

<210> SEQ ID NO 12
<211> LENGTH: 7
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 12

Ile Thr Ser Gly Gly Ser Thr
1               5

<210> SEQ ID NO 13
<211> LENGTH: 18
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 13

Asn Val Ala Gly Arg Asn Trp Val Pro Ile Ser Arg Tyr Ser Pro Gly
1               5                   10                  15

Pro Tyr

<210> SEQ ID NO 14
<211> LENGTH: 18
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 14

Ala Val Ala Gly Arg Asn Trp Val Pro Ile Ser Arg Tyr Ser Pro Gly
1               5                   10                  15

Pro Tyr
```

```
<210> SEQ ID NO 15
<211> LENGTH: 9
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 15

Gly Ser Ile Glu Ser Ile Asn Arg Met
1               5

<210> SEQ ID NO 16
<211> LENGTH: 7
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 16

Ile Ser Lys Gly Gly Ser Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 17

Ala Ala Gly Pro Val Trp Glu Gln Phe
1               5

<210> SEQ ID NO 18
<211> LENGTH: 9
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 18

Gly Arg Thr Ile Ser Leu Tyr Ala Val
1               5

<210> SEQ ID NO 19
<211> LENGTH: 8
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 19

Ile Ser Trp Thr Asp Ser Ser Thr
1               5

<210> SEQ ID NO 20
<211> LENGTH: 16
```

```
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 20

Ala Ala Asp Val Ser Ile Arg Gly Leu Gln Lys Tyr Glu Tyr Asp Tyr
1               5                   10                  15

<210> SEQ ID NO 21
<211> LENGTH: 9
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 21

Thr Arg Thr Phe Ser Ser Tyr Ile Met
1               5

<210> SEQ ID NO 22
<211> LENGTH: 8
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 22

Ile Ser Trp Ser Gly Arg Met Thr
1               5

<210> SEQ ID NO 23
<211> LENGTH: 17
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 23

Ala Ala Asp Arg Thr Thr Ala Trp Gly Ala Pro Arg Ser Gln Tyr Asp
1               5                   10                  15

Ser

<210> SEQ ID NO 24
<211> LENGTH: 116
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 24

Gln Val Lys Leu Glu Glu Ser Gly Gly Gly Leu Val Gln Ala Gly Gly
1               5                   10                  15

Ser Leu Arg Leu Ser Cys Val Gly Pro Gly Phe Leu Leu Arg Ser Asn
                20                  25                  30

Thr Met Gly Trp Tyr Arg Gln Ala Pro Gly Lys Glu Arg Glu Leu Val
            35                  40                  45
```

Ala Phe Ile Arg Pro Ser Gly Leu Thr Asn Tyr Asn Asp Ala Val Gln
            50                   55                   60

Gly Arg Phe Thr Ile Ser Arg Asp Asn Ala Lys Asn Thr Val Tyr Leu
 65                   70                   75                   80

Gln Met Asn Ala Leu Lys Pro Glu Asp Thr Ala Val Tyr Tyr Cys His
                 85                   90                   95

Thr Arg Pro Pro Phe Gln Arg Asp Ser Trp Gly Gln Gly Thr Gln Val
            100                  105                  110

Thr Val Ser Ser
        115

<210> SEQ ID NO 25
<211> LENGTH: 116
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 25

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Leu Leu Arg Ser Asn
                 20                  25                  30

Thr Met Gly Trp Val Arg Gln Ala Pro Gly Lys Gly Leu Glu Trp Val
             35                  40                  45

Ser Phe Ile Arg Pro Ser Gly Leu Thr Asn Tyr Asn Asp Ala Val Gln
            50                   55                   60

Gly Arg Phe Thr Ile Ser Arg Asp Asn Ser Lys Asn Thr Leu Tyr Leu
 65                   70                   75                   80

Gln Met Asn Ser Leu Arg Ala Glu Asp Thr Ala Val Tyr Tyr Cys Ala
                 85                   90                   95

Thr Arg Pro Pro Phe Gln Arg Asp Ser Trp Gly Gln Gly Thr Leu Val
            100                  105                  110

Thr Val Ser Ser
        115

<210> SEQ ID NO 26
<211> LENGTH: 116
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 26

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Leu Leu Arg Ser Asn
                 20                  25                  30

Thr Met Gly Trp Tyr Arg Gln Ala Pro Gly Lys Gly Leu Glu Leu Val
             35                  40                  45

Ser Phe Ile Arg Pro Ser Gly Leu Thr Asn Tyr Asn Asp Ala Val Gln
            50                   55                   60

Gly Arg Phe Thr Ile Ser Arg Asp Asn Ser Lys Asn Thr Leu Tyr Leu
 65                   70                   75                   80

```
Gln Met Asn Ser Leu Arg Ala Glu Asp Thr Ala Val Tyr Tyr Cys Ala
                85                  90                  95

Thr Arg Pro Pro Phe Gln Arg Asp Ser Trp Gly Gln Gly Thr Leu Val
            100                 105                 110

Thr Val Ser Ser
        115

<210> SEQ ID NO 27
<211> LENGTH: 116
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Leu Leu Arg Ser Asn
            20                  25                  30

Thr Met Gly Trp Tyr Arg Gln Ala Pro Gly Lys Gly Leu Glu Leu Val
        35                  40                  45

Ser Phe Ile Arg Pro Ser Gly Leu Thr Asn Tyr Asn Asp Ala Val Gln
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys His
                85                  90                  95

Thr Arg Pro Pro Phe Gln Arg Asp Ser Trp Gly Gln Gly Thr Leu Val
            100                 105                 110

Thr Val Ser Ser
        115

<210> SEQ ID NO 28
<211> LENGTH: 116
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Leu Leu Arg Ser Asn
            20                  25                  30

Thr Met Gly Trp Tyr Arg Gln Ala Pro Gly Lys Glu Arg Glu Leu Val
        35                  40                  45

Ser Phe Ile Arg Pro Ser Gly Leu Thr Asn Tyr Asn Asp Ala Val Gln
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys His
                85                  90                  95

Thr Arg Pro Pro Phe Gln Arg Asp Ser Trp Gly Gln Gly Thr Leu Val
            100                 105                 110

Thr Val Ser Ser
```

<210> SEQ ID NO 29
<211> LENGTH: 116
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 29

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Leu Leu Arg Ser Asn
            20                  25                  30

Thr Met Gly Trp Tyr Arg Gln Ala Pro Gly Lys Glu Arg Glu Leu Val
        35                  40                  45

Ala Phe Ile Arg Pro Ser Gly Leu Thr Asn Tyr Asn Asp Ala Val Gln
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys His
                85                  90                  95

Thr Arg Pro Pro Phe Gln Arg Asp Ser Trp Gly Gln Gly Thr Leu Val
            100                 105                 110

Thr Val Ser Ser
        115

<210> SEQ ID NO 30
<211> LENGTH: 116
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 30

Gln Val Gln Leu Val Glu Ser Gly Gly Gly Leu Val Gln Pro Gly Gly
1               5                   10                  15

Ser Leu Arg Leu Ser Cys Ala Gly Pro Gly Phe Leu Leu Arg Ser Asn
            20                  25                  30

Thr Met Gly Trp Tyr Arg Gln Ala Pro Gly Lys Glu Arg Glu Leu Val
        35                  40                  45

Ala Phe Ile Arg Pro Ser Gly Leu Thr Asn Tyr Asn Asp Ala Val Gln
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys His
                85                  90                  95

Thr Arg Pro Pro Phe Gln Arg Asp Ser Trp Gly Gln Gly Thr Leu Val
            100                 105                 110

Thr Val Ser Ser
        115

<210> SEQ ID NO 31
<211> LENGTH: 116
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 31

```
Gln Val Gln Leu Val Glu Ser Gly Gly Gly Leu Val Gln Pro Gly Gly
1               5                   10                  15

Ser Leu Arg Leu Ser Cys Ala Gly Pro Gly Phe Leu Leu Arg Ser Asn
            20                  25                  30

Thr Met Gly Trp Tyr Arg Gln Ala Pro Gly Lys Glu Arg Glu Leu Val
        35                  40                  45

Ala Phe Ile Arg Pro Ser Gly Leu Thr Asn Tyr Asn Asp Ala Val Gln
    50                  55                  60

Gly Arg Phe Thr Ile Ser Arg Asp Asn Ala Lys Asn Thr Val Tyr Leu
65                  70                  75                  80

Gln Met Asn Ser Leu Arg Ala Glu Asp Thr Ala Val Tyr Tyr Cys His
                85                  90                  95

Thr Arg Pro Pro Phe Gln Arg Asp Ser Trp Gly Gln Gly Thr Leu Val
            100                 105                 110

Thr Val Ser Ser
        115
```

<210> SEQ ID NO 32
<211> LENGTH: 126
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 32

```
Gln Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ile Ala Tyr
            20                  25                  30

Ala Met Gly Trp Phe Arg Gln Ala Pro Gly Lys Glu Arg Glu Phe Val
        35                  40                  45

Ala Ala Ile Thr Asn Phe Ala Gly Gly Thr Thr Tyr Tyr Ala Asp Ser
    50                  55                  60

Val Lys Gly Arg Phe Thr Ile Ser Arg Asp Asn Ala Lys Thr Thr Val
65                  70                  75                  80

Tyr Leu Gln Met Asn Ser Leu Lys Pro Glu Asp Thr Ala Leu Tyr Tyr
                85                  90                  95

Cys Ala Ala Asp Arg Ser Ala Gln Thr Met Arg Gln Val Arg Pro Val
            100                 105                 110

Leu Pro Tyr Trp Gly Gln Gly Thr Gln Val Thr Val Ser Ser
        115                 120                 125
```

<210> SEQ ID NO 33
<211> LENGTH: 126
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ile Ala Tyr
            20                  25                  30

Ala Met Gly Trp Val Arg Gln Ala Pro Gly Lys Gly Leu Glu Trp Val
        35                  40                  45

Ser Ala Ile Thr Asn Phe Ala Gly Gly Thr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Ala Asp Arg Ser Ala Gln Thr Met Arg Gln Val Arg Pro Val
            100                 105                 110

Leu Pro Tyr Trp Gly Gln Gly Thr Leu Val Thr Val Ser Ser
            115                 120                 125

<210> SEQ ID NO 34
<211> LENGTH: 126
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ile Ala Tyr
            20                  25                  30

Ala Met Gly Trp Phe Arg Gln Ala Pro Gly Lys Gly Leu Glu Phe Val
        35                  40                  45

Ser Ala Ile Thr Asn Phe Ala Gly Gly Thr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Ala Asp Arg Ser Ala Gln Thr Met Arg Gln Val Arg Pro Val
            100                 105                 110

Leu Pro Tyr Trp Gly Gln Gly Thr Leu Val Thr Val Ser Ser
            115                 120                 125

<210> SEQ ID NO 35
<211> LENGTH: 126
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ile Ala Tyr
            20                  25                  30

Ala Met Gly Trp Phe Arg Gln Ala Pro Gly Lys Glu Arg Glu Phe Val

```
                35                  40                  45
Ser Ala Ile Thr Asn Phe Ala Gly Gly Thr Thr Tyr Tyr Ala Asp Ser
        50                  55                  60
Val Lys Gly Arg Phe Thr Ile Ser Arg Asp Asn Ser Lys Asn Thr Leu
 65                  70                  75                  80
Tyr Leu Gln Met Asn Ser Leu Arg Ala Glu Asp Thr Ala Val Tyr Tyr
                85                  90                  95
Cys Ala Ala Asp Arg Ser Ala Gln Thr Met Arg Gln Val Arg Pro Val
               100                 105                 110
Leu Pro Tyr Trp Gly Gln Gly Thr Leu Val Thr Val Ser Ser
               115                 120                 125

<210> SEQ ID NO 36
<211> LENGTH: 126
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 36

Gln Val Gln Leu Val Glu Ser Gly Gly Gly Leu Val Gln Pro Gly Gly
 1               5                  10                  15
Ser Leu Arg Leu Ser Cys Ala Ala Ser Gly Arg Thr Phe Ile Ala Tyr
                20                  25                  30
Ala Met Gly Trp Phe Arg Gln Ala Pro Gly Lys Glu Arg Glu Phe Val
                35                  40                  45
Ala Ala Ile Thr Asn Phe Ala Gly Gly Thr Thr Tyr Tyr Ala Asp Ser
        50                  55                  60
Val Lys Gly Arg Phe Thr Ile Ser Arg Asp Asn Ser Lys Asn Thr Leu
 65                  70                  75                  80
Tyr Leu Gln Met Asn Ser Leu Arg Ala Glu Asp Thr Ala Val Tyr Tyr
                85                  90                  95
Cys Ala Ala Asp Arg Ser Ala Gln Thr Met Arg Gln Val Arg Pro Val
               100                 105                 110
Leu Pro Tyr Trp Gly Gln Gly Thr Leu Val Thr Val Ser Ser
               115                 120                 125

<210> SEQ ID NO 37
<211> LENGTH: 126
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 37

Gln Val Gln Leu Val Glu Ser Gly Gly Gly Leu Val Gln Pro Gly Gly
 1               5                  10                  15
Ser Leu Arg Leu Ser Cys Ala Ala Ser Gly Arg Thr Phe Ile Ala Tyr
                20                  25                  30
Ala Met Gly Trp Phe Arg Gln Ala Pro Gly Lys Glu Arg Glu Phe Val
                35                  40                  45
Ala Ala Ile Thr Asn Phe Ala Gly Gly Thr Thr Tyr Tyr Ala Asp Ser
        50                  55                  60
Val Lys Gly Arg Phe Thr Ile Ser Arg Asp Asn Ala Lys Thr Thr Leu
 65                  70                  75                  80
```

```
Tyr Leu Gln Met Asn Ser Leu Arg Ala Glu Asp Thr Ala Val Tyr Tyr
                85                  90                  95

Cys Ala Ala Asp Arg Ser Ala Gln Thr Met Arg Gln Val Arg Pro Val
            100                 105                 110

Leu Pro Tyr Trp Gly Gln Gly Thr Leu Val Thr Val Ser Ser
        115                 120                 125

<210> SEQ ID NO 38
<211> LENGTH: 126
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 38

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ile Ala Tyr
            20                  25                  30

Ala Met Gly Trp Phe Arg Gln Ala Pro Gly Lys Glu Arg Glu Phe Val
        35                  40                  45

Ala Ala Ile Thr Asn Phe Ala Gly Gly Thr Thr Tyr Tyr Ala Asp Ser
    50                  55                  60

Val Lys Gly Arg Phe Thr Ile Ser Arg Asp Asn Ala Lys Thr Thr Val
65                  70                  75                  80

Tyr Leu Gln Met Asn Ser Leu Arg Ala Glu Asp Thr Ala Val Tyr Tyr
                85                  90                  95

Cys Ala Ala Asp Arg Ser Ala Gln Thr Met Arg Gln Val Arg Pro Val
            100                 105                 110

Leu Pro Tyr Trp Gly Gln Gly Thr Leu Val Thr Val Ser Ser
        115                 120                 125

<210> SEQ ID NO 39
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 39

Gln Val Gln Leu Val Glu Ser Gly Gly Gly Phe Val Gln Ala Gly Gly
1               5                   10                  15

Ser Leu Arg Leu Ser Cys Ala Ala Ser Gly Arg Thr Phe Asp Asn Tyr
            20                  25                  30

Val Met Ala Trp Phe Arg Gln Ala Pro Gly Lys Glu Arg Glu Phe Val
        35                  40                  45

Ala Ser Ile Ser Gly Ser Gly Ser Ile Thr Asn Tyr Ala Asn Ser Val
    50                  55                  60

Lys Asp Arg Phe Thr Ile Ser Arg Asp Ser Ala Lys Asn Ala Ile Tyr
65                  70                  75                  80

Leu Gln Met Asn Ser Leu Lys Pro Glu Asp Thr Ala Leu Tyr Tyr Cys
                85                  90                  95

Ala Ala Gly Ser Arg Arg Thr Tyr Arg Glu Pro Lys Phe Tyr Pro
            100                 105                 110
```

-continued

Ser Trp Gly Gln Gly Thr Gln Val Thr Val Ser Ser
        115                 120

<210> SEQ ID NO 40
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Asp Asn Tyr
            20                  25                  30

Val Met Ala Trp Val Arg Gln Ala Pro Gly Lys Gly Leu Glu Trp Val
        35                  40                  45

Ser Ser Ile Ser Gly Ser Gly Ser Ile Thr Asn Tyr Ala Asn Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Ser Arg Arg Thr Tyr Tyr Arg Glu Pro Lys Phe Tyr Pro
            100                 105                 110

Ser Trp Gly Gln Gly Thr Leu Val Thr Val Ser Ser
        115                 120

<210> SEQ ID NO 41
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Asp Asn Tyr
            20                  25                  30

Val Met Ala Trp Phe Arg Gln Ala Pro Gly Lys Gly Leu Glu Phe Val
        35                  40                  45

Ser Ser Ile Ser Gly Ser Gly Ser Ile Thr Asn Tyr Ala Asn Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Ser Arg Arg Thr Tyr Tyr Arg Glu Pro Lys Phe Tyr Pro
            100                 105                 110

Ser Trp Gly Gln Gly Thr Leu Val Thr Val Ser Ser
        115                 120

<210> SEQ ID NO 42
<211> LENGTH: 124
<212> TYPE: PRT

<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Asp Asn Tyr
            20                  25                  30

Val Met Ala Trp Phe Arg Gln Ala Pro Gly Lys Glu Arg Glu Phe Val
        35                  40                  45

Ser Ser Ile Ser Gly Ser Gly Ser Ile Thr Asn Tyr Ala Asn Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Ser Arg Arg Thr Tyr Tyr Arg Glu Pro Lys Phe Tyr Pro
            100                 105                 110

Ser Trp Gly Gln Gly Thr Leu Val Thr Val Ser Ser
        115                 120

<210> SEQ ID NO 43
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 43

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Asp Asn Tyr
            20                  25                  30

Val Met Ala Trp Phe Arg Gln Ala Pro Gly Lys Glu Arg Glu Phe Val
        35                  40                  45

Ala Ser Ile Ser Gly Ser Gly Ser Ile Thr Asn Tyr Ala Asn Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Ser Arg Arg Thr Tyr Tyr Arg Glu Pro Lys Phe Tyr Pro
            100                 105                 110

Ser Trp Gly Gln Gly Thr Leu Val Thr Val Ser Ser
        115                 120

<210> SEQ ID NO 44
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 44

-continued

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Asp Asn Tyr
            20                  25                  30

Val Met Ala Trp Phe Arg Gln Ala Pro Gly Lys Glu Arg Glu Phe Val
        35                  40                  45

Ala Ser Ile Ser Gly Ser Gly Ser Ile Thr Asn Tyr Ala Asn Ser Val
    50                  55                  60

Lys Asp Arg Phe Thr Ile Ser Arg Asp Ser Ser Lys Asn Ala Leu Tyr
65                  70                  75                  80

Leu Gln Met Asn Ser Leu Arg Ala Glu Asp Thr Ala Val Tyr Tyr Cys
                85                  90                  95

Ala Ala Gly Ser Arg Arg Thr Tyr Tyr Arg Glu Pro Lys Phe Tyr Pro
            100                 105                 110

Ser Trp Gly Gln Gly Thr Leu Val Thr Val Ser Ser
        115                 120

<210> SEQ ID NO 45
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 45

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Asp Asn Tyr
            20                  25                  30

Val Met Ala Trp Phe Arg Gln Ala Pro Gly Lys Glu Arg Glu Phe Val
        35                  40                  45

Ala Ser Ile Ser Gly Ser Gly Ser Ile Thr Asn Tyr Ala Asn Ser Val
    50                  55                  60

Lys Asp Arg Phe Thr Ile Ser Arg Asp Ser Ala Lys Asn Ala Ile Tyr
65                  70                  75                  80

Leu Gln Met Asn Ser Leu Arg Ala Glu Asp Thr Ala Val Tyr Tyr Cys
                85                  90                  95

Ala Ala Gly Ser Arg Arg Thr Tyr Tyr Arg Glu Pro Lys Phe Tyr Pro
            100                 105                 110

Ser Trp Gly Gln Gly Thr Leu Val Thr Val Ser Ser
        115                 120

<210> SEQ ID NO 46
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 46

Gln Val Lys Leu Glu Glu Ser Gly Gly Gly Leu Val Gln Ala Gly Gly
1               5                   10                  15

Ser Leu Lys Leu Ser Cys Ala Ala Ser Gly Ser Thr Phe Ser Ser Ser
            20                  25                  30

-continued

Ser Val Gly Trp Tyr Arg Gln Ala Pro Gly Gln Arg Glu Leu Val
        35                  40                  45

Ala Ala Ile Thr Ser Gly Gly Ser Thr Asn Thr Ala Asp Ser Val Lys
 50                  55                  60

Gly Arg Phe Thr Met Ser Arg Asp Asn Ala Lys Asn Thr Val Tyr Leu
 65                  70                  75                  80

Gln Met Arg Asp Leu Lys Pro Glu Asp Thr Ala Val Tyr Tyr Cys Asn
                 85                  90                  95

Val Ala Gly Arg Asn Trp Val Pro Ile Ser Arg Tyr Ser Pro Gly Pro
            100                 105                 110

Tyr Trp Gly Gln Gly Thr Gln Val Thr Val Ser Ser
        115                 120

<210> SEQ ID NO 47
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 47

Glu Val Gln Leu Val Glu Ser Gly Gly Gly Leu Val Gln Pro Gly Gly
 1               5                   10                  15

Ser Leu Arg Leu Ser Cys Ala Ala Ser Gly Ser Thr Phe Ser Ser Ser
                20                  25                  30

Ser Val Gly Trp Val Arg Gln Ala Pro Gly Lys Gly Leu Glu Trp Val
        35                  40                  45

Ser Ala Ile Thr Ser Gly Gly Ser Thr Asn Thr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Val Ala Gly Arg Asn Trp Val Pro Ile Ser Arg Tyr Ser Pro Gly Pro
            100                 105                 110

Tyr Trp Gly Gln Gly Thr Leu Val Thr Val Ser Ser
        115                 120

<210> SEQ ID NO 48
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 48

Glu Val Gln Leu Val Glu Ser Gly Gly Gly Leu Val Gln Pro Gly Gly
 1               5                   10                  15

Ser Leu Arg Leu Ser Cys Ala Ala Ser Gly Ser Thr Phe Ser Ser Ser
                20                  25                  30

Ser Val Gly Trp Tyr Arg Gln Ala Pro Gly Lys Gly Leu Glu Leu Val
        35                  40                  45

Ser Ala Ile Thr Ser Gly Gly Ser Thr Asn Thr Ala Asp Ser Val Lys
 50                  55                  60

Gly Arg Phe Thr Ile Ser Arg Asp Asn Ser Lys Asn Thr Leu Tyr Leu

```
                 65                  70                  75                  80
Gln Met Asn Ser Leu Arg Ala Glu Asp Thr Ala Val Tyr Tyr Cys Ala
                85                  90                  95

Val Ala Gly Arg Asn Trp Val Pro Ile Ser Arg Tyr Ser Pro Gly Pro
               100                 105                 110

Tyr Trp Gly Gln Gly Thr Leu Val Thr Val Ser Ser
            115                 120

<210> SEQ ID NO 49
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 49

Glu Val Gln Leu Val Glu Ser Gly Gly Gly Leu Val Gln Pro Gly Gly
1               5                  10                  15

Ser Leu Arg Leu Ser Cys Ala Ala Ser Gly Ser Thr Phe Ser Ser Ser
                20                  25                  30

Ser Val Gly Trp Tyr Arg Gln Ala Pro Gly Lys Gly Leu Glu Leu Val
            35                  40                  45

Ser Ala Ile Thr Ser Gly Gly Ser Thr Asn Thr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Val Ala Gly Arg Asn Trp Val Pro Ile Ser Arg Tyr Ser Pro Gly Pro
               100                 105                 110

Tyr Trp Gly Gln Gly Thr Leu Val Thr Val Ser Ser
            115                 120

<210> SEQ ID NO 50
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 50

Glu Val Gln Leu Val Glu Ser Gly Gly Gly Leu Val Gln Pro Gly Gly
1               5                  10                  15

Ser Leu Arg Leu Ser Cys Ala Ala Ser Gly Ser Thr Phe Ser Ser Ser
                20                  25                  30

Ser Val Gly Trp Tyr Arg Gln Ala Pro Gly Lys Gln Arg Glu Leu Val
            35                  40                  45

Ser Ala Ile Thr Ser Gly Gly Ser Thr Asn Thr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Val Ala Gly Arg Asn Trp Val Pro Ile Ser Arg Tyr Ser Pro Gly Pro
               100                 105                 110
```

```
Tyr Trp Gly Gln Gly Thr Leu Val Thr Val Ser Ser
            115                 120

<210> SEQ ID NO 51
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 51

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Ser Ser Ser
            20                  25                  30

Ser Val Gly Trp Tyr Arg Gln Ala Pro Gly Gln Gln Arg Glu Leu Val
        35                  40                  45

Ala Ala Ile Thr Ser Gly Gly Ser Thr Asn Thr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Val Ala Gly Arg Asn Trp Val Pro Ile Ser Arg Tyr Ser Pro Gly Pro
            100                 105                 110

Tyr Trp Gly Gln Gly Thr Leu Val Thr Val Ser Ser
            115                 120

<210> SEQ ID NO 52
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 52

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Ser Ser Ser
            20                  25                  30

Ser Val Gly Trp Tyr Arg Gln Ala Pro Gly Gln Gln Arg Glu Leu Val
        35                  40                  45

Ala Ala Ile Thr Ser Gly Gly Ser Thr Asn Thr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Arg Ala Glu Asp Thr Ala Val Tyr Tyr Cys Asn
                85                  90                  95

Val Ala Gly Arg Asn Trp Val Pro Ile Ser Arg Tyr Ser Pro Gly Pro
            100                 105                 110

Tyr Trp Gly Gln Gly Thr Leu Val Thr Val Ser Ser
            115                 120

<210> SEQ ID NO 53
<211> LENGTH: 115
```

```
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 53

Gln Val Gln Leu Val Glu Ser Gly Gly Gly Leu Val Gln Ala Gly Gly
1               5                   10                  15

Ser Leu Arg Leu Ser Cys Thr Ala Ser Gly Ser Ile Glu Ser Ile Asn
            20                  25                  30

Arg Met Ala Trp Tyr Arg Gln Ala Pro Gly Gln Gln Arg Glu Phe Val
        35                  40                  45

Ala Arg Ile Ser Lys Gly Gly Ser Thr Asn Tyr Pro Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Gly Pro Val Trp Glu Gln Phe Trp Gly Gln Gly Thr Gln Val Thr
            100                 105                 110

Val Ser Ser
        115

<210> SEQ ID NO 54
<211> LENGTH: 115
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Glu Ser Ile Asn
            20                  25                  30

Arg Met Ala Trp Val Arg Gln Ala Pro Gly Lys Gly Leu Glu Trp Val
        35                  40                  45

Ser Arg Ile Ser Lys Gly Gly Ser Thr Asn Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Gly Pro Val Trp Glu Gln Phe Trp Gly Gln Gly Thr Leu Val Thr
            100                 105                 110

Val Ser Ser
        115

<210> SEQ ID NO 55
<211> LENGTH: 115
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
```

-continued

```
<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Glu Ser Ile Asn
            20                  25                  30

Arg Met Ala Trp Tyr Arg Gln Ala Pro Gly Lys Gly Leu Glu Phe Val
        35                  40                  45

Ser Arg Ile Ser Lys Gly Gly Ser Thr Asn Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Gly Pro Val Trp Glu Gln Phe Trp Gly Gln Gly Thr Leu Val Thr
            100                 105                 110

Val Ser Ser
        115

<210> SEQ ID NO 56
<211> LENGTH: 115
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Glu Ser Ile Asn
            20                  25                  30

Arg Met Ala Trp Tyr Arg Gln Ala Pro Gly Lys Gln Arg Glu Phe Val
        35                  40                  45

Ser Arg Ile Ser Lys Gly Gly Ser Thr Asn Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Gly Pro Val Trp Glu Gln Phe Trp Gly Gln Gly Thr Leu Val Thr
            100                 105                 110

Val Ser Ser
        115

<210> SEQ ID NO 57
<211> LENGTH: 115
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 57

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Glu Ser Ile Asn
            20                  25                  30
```

```
Arg Met Ala Trp Tyr Arg Gln Ala Pro Gly Lys Gln Arg Glu Phe Val
            35                  40                  45

Ala Arg Ile Ser Lys Gly Gly Ser Thr Asn Tyr Pro Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Gly Pro Val Trp Glu Gln Phe Trp Gly Gln Gly Thr Leu Val Thr
            100                 105                 110

Val Ser Ser
        115

<210> SEQ ID NO 58
<211> LENGTH: 115
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 58

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Glu Ser Ile Asn
            20                  25                  30

Arg Met Ala Trp Tyr Arg Gln Ala Pro Gly Gln Gln Arg Glu Phe Val
            35                  40                  45

Ala Arg Ile Ser Lys Gly Gly Ser Thr Asn Tyr Pro Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Gly Pro Val Trp Glu Gln Phe Trp Gly Gln Gly Thr Leu Val Thr
            100                 105                 110

Val Ser Ser
        115

<210> SEQ ID NO 59
<211> LENGTH: 115
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 59

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Glu Ser Ile Asn
            20                  25                  30

Arg Met Ala Trp Tyr Arg Gln Ala Pro Gly Gln Gln Arg Glu Phe Val
            35                  40                  45

Ala Arg Ile Ser Lys Gly Gly Ser Thr Asn Tyr Pro Asp Ser Val Lys
        50                  55                  60
```

```
Gly Arg Phe Thr Ile Ser Arg Asp Asn Ala Lys Asn Thr Val Tyr Leu
 65                  70                  75                  80

Gln Met Asn Ser Leu Arg Ala Glu Asp Thr Ala Val Tyr Tyr Cys Ala
             85                  90                  95

Ala Gly Pro Val Trp Glu Gln Phe Trp Gly Gln Gly Thr Leu Val Thr
            100                 105                 110

Val Ser Ser
        115

<210> SEQ ID NO 60
<211> LENGTH: 123
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 60

Gln Val Lys Leu Glu Glu Ser Gly Gly Gly Leu Val Gln Ala Gly Gly
 1               5                  10                  15

Ser Leu Arg Leu Ser Cys Ala Ala Ser Gly Arg Thr Ile Ser Leu Tyr
            20                  25                  30

Ala Val Gly Trp Phe Arg Arg Ala Pro Gly Lys Glu Arg Glu Phe Val
        35                  40                  45

Ala Ala Ile Ser Trp Thr Asp Ser Ser Thr Tyr Tyr Ala Asp Ser Val
    50                  55                  60

Lys Gly Arg Phe Thr Ile Ser Arg Asp Asn Ala Lys Asn Thr Val Tyr
 65                  70                  75                  80

Leu Gly Met Asn Ser Leu Asn Pro Glu Asp Thr Ala Val Tyr Tyr Cys
             85                  90                  95

Ala Ala Asp Val Ser Ile Arg Gly Leu Gln Lys Tyr Glu Tyr Asp Tyr
            100                 105                 110

Trp Gly Gln Gly Thr Gln Val Thr Val Ser Ser
        115                 120

<210> SEQ ID NO 61
<211> LENGTH: 123
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 61

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Ile Ser Leu Tyr
            20                  25                  30

Ala Val Gly Trp Val Arg Gln Ala Pro Gly Lys Gly Leu Glu Trp Val
        35                  40                  45

Ser Ala Ile Ser Trp Thr Asp Ser Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Ala Asp Val Ser Ile Arg Gly Leu Gln Lys Tyr Glu Tyr Asp Tyr
```

100                 105                 110

Trp Gly Gln Gly Thr Leu Val Thr Val Ser Ser
            115                 120

<210> SEQ ID NO 62
<211> LENGTH: 123
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ile Ser Leu Tyr
            20                  25                  30

Ala Val Gly Trp Phe Arg Gln Ala Pro Gly Lys Gly Leu Glu Phe Val
        35                  40                  45

Ser Ala Ile Ser Trp Thr Asp Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ser Ile Arg Gly Leu Gln Lys Tyr Glu Tyr Asp Tyr
            100                 105                 110

Trp Gly Gln Gly Thr Leu Val Thr Val Ser Ser
            115                 120

<210> SEQ ID NO 63
<211> LENGTH: 122
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ile Ser Leu Tyr
            20                  25                  30

Ala Val Gly Trp Phe Arg Gln Ala Pro Gly Lys Glu Arg Glu Phe Val
        35                  40                  45

Ser Ala Ile Ser Trp Thr Asp Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ser Ile Arg Gly Leu Gln Lys Tyr Glu Tyr Asp Tyr
            100                 105                 110

Trp Gly Gln Gly Thr Leu Val Thr Val Ser
            115                 120

<210> SEQ ID NO 64

```
<211> LENGTH: 123
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 64

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ile Ser Leu Tyr
            20                  25                  30

Ala Val Gly Trp Phe Arg Gln Ala Pro Gly Lys Glu Arg Glu Phe Val
        35                  40                  45

Ala Ala Ile Ser Trp Thr Asp Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ser Ile Arg Gly Leu Gln Lys Tyr Glu Tyr Asp Tyr
            100                 105                 110

Trp Gly Gln Gly Thr Leu Val Thr Val Ser Ser
        115                 120

<210> SEQ ID NO 65
<211> LENGTH: 123
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 65

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ile Ser Leu Tyr
            20                  25                  30

Ala Val Gly Trp Phe Arg Arg Ala Pro Gly Lys Glu Arg Glu Phe Val
        35                  40                  45

Ala Ala Ile Ser Trp Thr Asp Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ser Ile Arg Gly Leu Gln Lys Tyr Glu Tyr Asp Tyr
            100                 105                 110

Trp Gly Gln Gly Thr Leu Val Thr Val Ser Ser
        115                 120

<210> SEQ ID NO 66
<211> LENGTH: 122
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama
```

<400> SEQUENCE: 66

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ile Ser Leu Tyr
            20                  25                  30

Ala Val Gly Trp Phe Arg Arg Ala Pro Gly Lys Glu Arg Glu Phe Val
        35                  40                  45

Ala Ala Ile Ser Trp Thr Asp Ser Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Val Ser Ile Arg Gly Leu Gln Lys Tyr Glu Tyr Asp Tyr
            100                 105                 110

Trp Gly Gln Gly Thr Leu Val Thr Val Ser
        115                 120

<210> SEQ ID NO 67
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 67

Gln Val Lys Leu Glu Glu Ser Gly Gly Gly Leu Val Gln Ala Gly Gly
1               5                   10                  15

Ser Leu Arg Leu Ser Cys Thr Ala Ser Thr Arg Thr Phe Ser Ser Tyr
            20                  25                  30

Ile Met Gly Trp Phe Arg Gln Ala Pro Gly Lys Glu Arg Glu Leu Val
        35                  40                  45

Ala Ala Ile Ser Trp Ser Gly Arg Met Thr His Tyr Ala Asp Ser Val
    50                  55                  60

Lys Gly Arg Phe Ala Ile Ser Arg Asp Asn Ala Lys Asn Thr Val Tyr
65                  70                  75                  80

Leu Gln Met Asn Val Leu Lys Pro Glu Asp Thr Ala Ile Tyr Ser Cys
                85                  90                  95

Ala Ala Asp Arg Thr Thr Ala Trp Gly Ala Pro Arg Ser Gln Tyr Asp
            100                 105                 110

Ser Trp Gly Gln Gly Thr Gln Val Thr Val Ser Ser
        115                 120

<210> SEQ ID NO 68
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Thr Arg Thr Phe Ser Ser Tyr

```
                    20                  25                  30
Ile Met Gly Trp Val Arg Gln Ala Pro Gly Lys Gly Leu Glu Trp Val
                35                  40                  45

Ser Ala Ile Ser Trp Ser Gly Arg Met Thr His Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Ala Asp Arg Thr Thr Ala Trp Gly Ala Pro Arg Ser Gln Tyr Asp
                100                 105                 110

Ser Trp Gly Gln Gly Thr Leu Val Thr Val Ser Ser
                115                 120

<210> SEQ ID NO 69
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Thr Arg Thr Phe Ser Ser Tyr
                20                  25                  30

Ile Met Gly Trp Phe Arg Gln Ala Pro Gly Lys Gly Leu Glu Leu Val
                35                  40                  45

Ser Ala Ile Ser Trp Ser Gly Arg Met Thr His Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Ala Asp Arg Thr Thr Ala Trp Gly Ala Pro Arg Ser Gln Tyr Asp
                100                 105                 110

Ser Trp Gly Gln Gly Thr Leu Val Thr Val Ser Ser
                115                 120

<210> SEQ ID NO 70
<211> LENGTH: 123
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Thr Arg Thr Phe Ser Ser Tyr
                20                  25                  30

Ile Met Gly Trp Phe Arg Gln Ala Pro Gly Lys Glu Arg Glu Leu Val
                35                  40                  45

Ser Ala Ile Ser Trp Ser Gly Arg Met Thr His Tyr Ala Asp Ser Val
            50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Arg Thr Thr Ala Trp Gly Ala Pro Arg Ser Gln Tyr Asp
            100                 105                 110

Ser Trp Gly Gln Gly Thr Leu Val Thr Val Ser
            115                 120

<210> SEQ ID NO 71
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 71

Gln Val Gln Leu Val Glu Ser Gly Gly Gly Leu Val Gln Pro Gly Gly
1               5                   10                  15

Ser Leu Arg Leu Ser Cys Ala Ala Ser Thr Arg Thr Phe Ser Ser Tyr
            20                  25                  30

Ile Met Gly Trp Phe Arg Gln Ala Pro Gly Lys Glu Arg Glu Leu Val
        35                  40                  45

Ala Ala Ile Ser Trp Ser Gly Arg Met Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Arg Thr Thr Ala Trp Gly Ala Pro Arg Ser Gln Tyr Asp
            100                 105                 110

Ser Trp Gly Gln Gly Thr Leu Val Thr Val Ser Ser
            115                 120

<210> SEQ ID NO 72
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 72

Gln Val Gln Leu Val Glu Ser Gly Gly Gly Leu Val Gln Pro Gly Gly
1               5                   10                  15

Ser Leu Arg Leu Ser Cys Ala Ala Ser Thr Arg Thr Phe Ser Ser Tyr
            20                  25                  30

Ile Met Gly Trp Phe Arg Gln Ala Pro Gly Lys Glu Arg Glu Leu Val
        35                  40                  45

Ala Ala Ile Ser Trp Ser Gly Arg Met Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Ser Cys
                85                  90                  95

```
Ala Ala Asp Arg Thr Thr Ala Trp Gly Ala Pro Arg Ser Gln Tyr Asp
            100                 105                 110

Ser Trp Gly Gln Gly Thr Leu Val Thr Val Ser Ser
        115                 120
```

<210> SEQ ID NO 73
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 73

```
Gln Val Gln Leu Val Glu Ser Gly Gly Gly Leu Val Gln Pro Gly Gly
1               5                   10                  15

Ser Leu Arg Leu Ser Cys Ala Ala Ser Thr Arg Thr Phe Ser Ser Tyr
            20                  25                  30

Ile Met Gly Trp Phe Arg Gln Ala Pro Gly Lys Glu Arg Glu Leu Val
        35                  40                  45

Ala Ala Ile Ser Trp Ser Gly Arg Met Thr His Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Ile Tyr Ser Cys
                85                  90                  95

Ala Ala Asp Arg Thr Thr Ala Trp Gly Ala Pro Arg Ser Gln Tyr Asp
            100                 105                 110

Ser Trp Gly Gln Gly Thr Leu Val Thr Val Ser Ser
        115                 120
```

<210> SEQ ID NO 74
<211> LENGTH: 122
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 74

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Ser Arg Tyr
            20                  25                  30

Val Met Gly Trp Phe Arg Gln Ala Pro Gly Lys Glu Arg Glu Phe Val
        35                  40                  45

Ala Ala Ile Thr Trp Gly Gly Thr Pro Asn Tyr Ala Asp Ser Val Lys
    50                  55                  60

Gly Arg Phe Thr Ile Ser Arg Asp Asn Ser Lys Asn Thr Gln Tyr Leu
65                  70                  75                  80

Gln Met Asn Ser Leu Lys Pro Glu Asp Thr Ala Val Tyr Tyr Cys Ala
                85                  90                  95

Ala Gly Leu Gly Trp Asp Ser Arg Tyr Ser Gln Ser Tyr Asn Tyr Trp
            100                 105                 110

Gly Gln Gly Thr Gln Val Thr Val Ser Ser
        115                 120
```

```
<210> SEQ ID NO 75
<211> LENGTH: 123
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 75

Gln Val Gln Leu Val Glu Ser Gly Gly Gly Leu Ala Gln Ala Gly Gly
1               5                   10                  15

Ser Leu Arg Leu Ser Cys Ala Ala Ser Gly Arg Thr Phe Ser Met Asp
            20                  25                  30

Pro Met Ala Trp Phe Arg Gln Pro Pro Gly Lys Glu Arg Glu Phe Val
        35                  40                  45

Ala Ala Gly Ser Ser Thr Gly Arg Thr Thr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Pro Tyr Gly Ala Asn Trp Tyr Arg Asp Glu Tyr Ala Tyr
            100                 105                 110

Trp Gly Gln Gly Thr Gln Val Thr Val Ser Ser
            115                 120

<210> SEQ ID NO 76
<211> LENGTH: 124
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 76

Gln Val Lys Leu Glu Glu Ser Gly Gly Gly Leu Val Gln Ala Gly Gly
1               5                   10                  15

Ser Leu Arg Leu Ser Cys Ala Ala Ser Glu Arg Thr Phe Ser Arg Tyr
            20                  25                  30

Pro Val Ala Trp Phe Arg Gln Ala Pro Gly Ala Glu Arg Glu Phe Val
        35                  40                  45

Ala Val Ile Ser Ser Thr Gly Thr Ser Thr Tyr Tyr Ala Asp Ser Val
    50                  55                  60

Lys Gly Arg Phe Thr Ile Ser Arg Asp Asn Ala Lys Val Thr Val Tyr
65                  70                  75                  80

Leu Gln Met Asn Asn Leu Lys Arg Glu Asp Thr Ala Val Tyr Phe Cys
                85                  90                  95

Ala Val Asn Ser Gln Arg Thr Arg Leu Gln Asp Pro Asn Glu Tyr Asp
            100                 105                 110

Tyr Trp Gly Gln Gly Thr Gln Val Thr Val Ser Ser
            115                 120

<210> SEQ ID NO 77
<211> LENGTH: 122
<212> TYPE: PRT
<213> ORGANISM: Artificial Sequence
<220> FEATURE:
<223> OTHER INFORMATION: Amino Acid
<220> FEATURE:
```

<223> OTHER INFORMATION: Homo Sapiens

<400> SEQUENCE: 77

Lys Gly Gly Lys His His Leu Gly Leu Glu Glu Pro Lys Lys Leu Arg
1               5                   10                  15

Pro Pro Pro Ala Arg Thr Pro Cys Gln Gln Glu Leu Asp Gln Val Leu
            20                  25                  30

Glu Arg Ile Ser Thr Met Arg Leu Pro Asp Glu Arg Gly Pro Leu Glu
        35                  40                  45

His Leu Tyr Ser Leu His Ile Pro Asn Cys Asp Lys His Gly Leu Tyr
    50                  55                  60

Asn Leu Lys Gln Cys Lys Met Ser Leu Asn Gly Gln Arg Gly Glu Cys
65                  70                  75                  80

Trp Cys Val Asn Pro Asn Thr Gly Lys Leu Ile Gln Gly Ala Pro Thr
                85                  90                  95

Ile Arg Gly Asp Pro Glu Cys His Leu Phe Tyr Asn Glu Gln Gln Glu
            100                 105                 110

Ala Arg Gly Val His Thr Gln Arg Met Gln
        115                 120

<210> SEQ ID NO 78
<211> LENGTH: 122
<212> TYPE: PRT
<213> ORGANISM: Artificial Sequence
<220> FEATURE:
<223> OTHER INFORMATION: Amino Acid
<220> FEATURE:
<223> OTHER INFORMATION: Lama Glama

<400> SEQUENCE: 78

Glu Val Gln Leu Gln Ala Ser Gly Gly Gly Leu Val Gln Ala Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
                85                  90                  95

Ala Ala Gly Ser Thr Ser Thr Ala Thr Pro Leu Arg Val Asp Tyr Trp
            100                 105                 110

Gly Lys Gly Thr Gln Val Thr Val Ser Ser
        115                 120

<210> SEQ ID NO 79
<211> LENGTH: 40
<212> TYPE: PRT
<213> ORGANISM: Artificial Sequence
<220> FEATURE:
<223> OTHER INFORMATION: Amino Acid
<220> FEATURE:
<223> OTHER INFORMATION: Synthetic Peptide

<400> SEQUENCE: 79

Lys Thr Phe Lys Thr Arg Lys Ala Ser Ala Gln Ala Ser Leu Ala Ser
1               5                   10                  15

```
Lys Asp Lys Thr Pro Lys Ser Lys Ser Lys Lys Arg Asn Ser Thr Gln
            20                  25                  30

Leu Lys Ser Arg Val Lys Asn Ile
        35                  40
```

<210> SEQ ID NO 80
<211> LENGTH: 525
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 80

```
Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
```

```
                    325                 330                 335
Tyr Val Pro Gly Arg Thr Ala Ser Leu Pro Glu Ala Gly Glu Lys Leu
                340                 345                 350

Phe Pro Tyr Leu Asp Pro Phe Asp Ser Ala Ser Gln Leu Met Glu Pro
                355                 360                 365

Gly Arg Gln Ser Met Asp Leu Val Glu Leu Val Ser Leu Phe Pro Thr
            370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
                420                 425                 430

Arg Glu Leu Ile Ala Tyr Ser Gln Tyr Pro Arg Pro Ser Asp Ile Pro
                435                 440                 445

Gln Trp Asn Ser Asp Lys Pro Ser Leu Lys Asp Ile Lys Ile Met Gly
            450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
                500                 505                 510

Asp Ser Gln Gly Gly Asp Leu Phe Gln Leu Leu Met Pro
            515                 520                 525

<210> SEQ ID NO 81
<211> LENGTH: 5
<212> TYPE: PRT
<213> ORGANISM: Artificial Sequence
<220> FEATURE:
<223> OTHER INFORMATION: Amino Acid
<220> FEATURE:
<223> OTHER INFORMATION: Synthetic Peptide

<400> SEQUENCE: 81

Gly Gly Gly Gly Ser
1               5
```

SERUM ALBUMIN BINDING ANTIBODIES FOR TUNEABLE HALF-LIFE EXTENSION OF BIOLOGICS

CROSS-REFERENCE TO RELATED APPLICATIONS

This application is a U.S. National Phase application under 35 U.S.C. 371 of PCT/CA2019/050514, filed Apr. 24, 2019, which claims priority from and the benefit of U.S. Provisional Patent Application No. 62/661,871 filed on Apr. 24, 2018, the specifications of which are hereby incorporated by reference in their entireties.

REFERENCE TO AN ELECTRONIC SEQUENCE LISTING

The contents of the electronic sequence listing (SEQ.txt; Size: 75,250 bytes; and Date of Creation: Apr. 23, 2021) is herein incorporated by reference in its entirety.

BACKGROUND

(a) Field

The subject matter disclosed generally relates to antibodies or antigen-binding fragments that bind to serum albumin. More specifically, the subject matter relates to antibodies or antigen-binding fragments that bind to serum albumin for half-life extension of biologics, as well as compounds, pharmaceutical compositions, nucleic acid vectors, cells comprising the nucleic acid vectors, and methods of removing molecules from serum.

(b) Related Prior Art

Biologics of less than 40-50 kDa in size possess short serum half-lives due to rapid renal clearance. Strategies to prolong the serum half-life of various biologics (antibody fragments, single-domain antibodies, enzymes, growth factors, peptides) are critically important for efficacy. The half-life of biologics can be extended through various techniques, including, but not limited to PEGylation, PASylation, conjugation to carbohydrates, fusion to an IgG Fc domain, fusion to serum albumin, and fusion to an albumin binding domain or antibody binding domain that recognizes serum albumin. In the latter case, single-domain antibodies (referred to as sdAbs, $V_HHs$, or nanobodies), which are naturally occurring autonomous binding domains found in Camelid species, are ideal agents for which to target serum albumin for half-life extension. The flexibility $V_HHs$ offer in terms of modularity and functionality allow for fusion to many biologics, in both N- and C-terminal orientations, without compensating target binding affinities or specificity.

The requirements for $V_HH$-based half-life extension of biologics are as follows: (i) high affinity binding and species cross-reactivity of the $V_HH$ to the relevant serum albumins (human, monkey, rat, mouse) at pH 7.4, (ii) high affinity binding and species cross-reactivity of the $V_HH$ to the relevant serum albumins (human, monkey, rat, mouse) at pH 5.5, (iii) the anti-serum albumin $V_HH$ cannot compete with FcRn for albumin binding, and (iv) the anti-serum albumin $V_HH$ must retain functionality when fused to biologics through linkers.

On the other hand, many harmful molecules (e.g., protein-based bacterial toxin or venoms) need to be removed as quickly as possible from the body. Increasing their rate of removal will have therapeutic effects and prevent disease. To remove harmful molecules from circulation, a direct neutralizing agent (e.g., antibody) can be used to neutralize the harmful effects of the toxic molecules. Presently, direct neutralization of many toxins is not efficacious enough (the toxic substance is not removed quickly enough from serum) leaving significant room for improvement of therapeutic antibody efficacy.

Therefore, there is a need for additional $V_HHs$ which target multiple serum albumin species, for the purpose of extending the serum half-life of biologics or removal of harmful molecules.

The following application describes the isolation, characterization, and in vivo testing of several llama-derived $V_HHs$ which target multiple serum albumin species, for the purpose of extending the serum half-life of biologics or removal of harmful molecules.

SUMMARY

According to an embodiment, there is provided an antibody or an antigen-binding fragment that binds to serum albumin comprising three complementarity determining regions (CDR1, CDR2 and CDR3), wherein the CDR1, CDR2 and CDR3 comprise an amino acid sequence comprising:

1)
```
                                    (SEQ ID NO: 1)
GFLLRSNTM, (SEQ ID NO: 2)
IRPSGLT,
and (SEQ ID NO: 3)
HTRPPFQRDS
or (SEQ ID NO: 4)
ATRPPFQRDS,
respectively; or 2)
                                    (SEQ ID NO: 5)
GRTFIAYAM, (SEQ ID NO: 6)
ITNFAGGTT,
and (SEQ ID NO: 7)
AADRSAQTMRQVRPVLPY,
respectively; or 3)
                                    (SEQ ID NO: 8)
GRTFDNYVM, (SEQ ID NO: 9)
ISGSGSIT,
and (SEQ ID NO: 10)
AAGSRRTYYREPKFYPS,
respectively; or 4)
                                    (SEQ ID NO: 11)
GSTFSSSSV, (SEQ ID NO: 12)
ITSGGST,
and
```

```
                                          (SEQ ID NO: 13)
NVAGRNWVPISRYSPGPY
or (SEQ ID NO: 14)
AVAGRNWVPISRYSPGPY,
respectively; or 5)
                                          (SEQ ID NO: 15)
GSIESINRM, (SEQ ID NO: 16)
ISKGGST,
and (SEQ ID NO: 17)
AAGPVWEQF,
respectively; or 6)
                                          (SEQ ID NO: 18)
GRTISLYAV, (SEQ ID NO: 19)
ISWTDSST,
and (SEQ ID NO: 20)
AADVSIRGLQKYEYDY,
respectively; or 7)
                                          (SEQ ID NO: 21)
TRTFSSYIM, (SEQ ID NO: 22)
ISWSGRMT,
and (SEQ ID NO: 23)
AADRTTAWGAPRSQYDS,
respectively.
```

The antigen-binding fragment may be a single-domain antibody (sdAb).

The antibody may be an IgA, IgD, IgE, IgG, or IgM.

The CDR1, CDR2 and CDR3 may comprise an amino acid sequence comprising GFLLRSNTM (SEQ ID NO:1), IRPSGLT (SEQ ID NO:2), and HTRPPFQRDS (SEQ ID NO:3) or ATRPPFQRDS (SEQ ID NO:4), respectively.

The CDR1, CDR2 and CDR3 may comprise an amino acid sequence comprising GRTFIAYAM (SEQ ID NO:5), ITNFAGGTT (SEQ ID NO:6), and AADRSAQTMRQVRPVLPY (SEQ ID NO:7), respectively.

The CDR1, CDR2 and CDR3 may comprise an amino acid sequence comprising GRTFDNYVM (SEQ ID NO:8), ISGSGSIT (SEQ ID NO:9), and AAGSRRTYYREPKFYPS (SEQ ID NO:10), respectively.

The CDR1, CDR2 and CDR3 may comprise an amino acid sequence comprising GSTFSSSSV (SEQ ID NO:11), ITSGGST (SEQ ID NO:12), and NVAGRNWVPISRYSPGPY (SEQ ID NO:13) or AVAGRNWVPISRYSPGPY (SEQ ID NO:14), respectively.

The CDR1, CDR2 and CDR3 may comprise an amino acid sequence comprising GSIESINRM (SEQ ID NO:15), ISKGGST (SEQ ID NO:16), and AAGPVWEQF (SEQ ID NO:17), respectively.

The CDR1, CDR2 and CDR3 may comprise an amino acid sequence comprising GRTISLYAV (SEQ ID NO:18), ISWTDSST (SEQ ID NO:19), and AADVSIRGLQKYEYDY (SEQ ID NO:20), respectively.

The CDR1, CDR2 and CDR3 may comprise an amino acid sequence comprising TRTFSSYIM (SEQ ID NO:21), ISWSGRMT (SEQ ID NO:22), and AADRTTAWGAPRSQYDS (SEQ ID NO:23), respectively.

The antibody or an antigen-binding fragment may be humanized or partially humanized.

According to another embodiment, there is provided a compound comprising an antibody or an antigen-binding fragment according to the present invention.

The antibody or an antigen-binding fragment may be linked to the compound via a linker.

The linker may be an amino acid sequence that allows for the functional linking of the compound to the antibody or an antigen-binding fragment.

The amino acid sequence may comprise about 3 to about 40 amino acids.

The linker sequence may be $(GGGGS)_n$ (SEQ ID NO:81) wherein n ≥1, or any suitable linker.

The antibody or an antigen-binding fragment may be fused to an antibody or an antigen-binding fragment, operable to bind a target epitope.

The antibody or an antigen-binding fragment may be linked to a peptide, a polypeptide, a protein, an enzyme, an antibody, an antibody fragment, or combinations thereof, wherein each of the antibody or an antigen-binding fragment and the linked peptide, polypeptide, protein, enzyme, antibody, antibody fragment, or combinations thereof are functional.

According to another embodiment, there is provided a composition comprising the compound of the present invention, and a pharmaceutically acceptable diluent, carrier or excipient.

According to another embodiment, there is provided a nucleic acid vector comprising a nucleotide sequence encoding a compound of the present invention.

According to another embodiment, there is provided a cell comprising the nucleic acid vector of the present invention for expressing the compound of the present invention.

According to another embodiment, there is provided a cell for expressing the compound of the present invention.

According to another embodiment, there is provided a method of removing a molecule from serum, comprising administering a compound according to the present invention specific to the molecule, wherein the antibody or an antigen-binding fragment comprises CDR1, CDR2 and CDR3 comprising an amino acid sequence comprising GRTFDNYVM (SEQ ID NO:8), ISGSGSIT (SEQ ID NO:9), and AAGSRRTYYREPKFYPS (SEQ ID NO:10), respectively.

According to another embodiment, there is provided a use of a compound according to the present invention specific to a molecule for removing the molecule from serum, wherein the sdAb comprises CDR1, CDR2 and CDR3 comprising an amino acid sequence comprising GRTFDNYVM (SEQ ID NO:8), ISGSGSIT (SEQ ID NO:9), and AAGSRRTYYREPKFYPS (SEQ ID NO:10), respectively.

According to another embodiment, there is provided a solid support for purification of albumin, derivatives thereof, or fragments thereof comprising a solid or semi-solid medium linked to an antibody or an antigen-binding fragment according to the present invention or a compound according to the present invention.

According to another embodiment, there is provided a method of purifying albumin comprising contacting an albumin containing sample with a solid support according to the present invention.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which:

FIG. 2A illustrates the sequences of wild-type serum albumin binding $V_H$Hs and their humanized variants. The sequences of isolated (llama, wild-type) and humanized $V_H$Hs are shown. The international ImMunoGeneTics information (IMGT) numbering system is used to distinguish framework regions (FRs) and complementarity determining regions (CDRs). The sequences of (A) R11 (SEQ ID NO:24), R11-H0 (SEQ ID NO:25), R11-H1 (SEQ ID NO:26), R11-H2 (SEQ ID NO:27), R11-H3 (SEQ ID NO:28), R11-H4 (SEQ ID NO:29), R11-H5 (SEQ ID NO:30), R11-H6 (SEQ ID NO:31) $V_H$Hs, (B) R28 (SEQ ID NO:32), R28-H0 (SEQ ID NO:33), R28-H1 (SEQ ID NO:34), R28-H2 (SEQ ID NO:35), R28-H3 (SEQ ID NO:36), R28-H4 (SEQ ID NO:37), R28-H5 (SEQ ID NO:38) $V_H$Hs, (C) M75 (SEQ ID NO:39), M75-H0 (SEQ ID NO:40), M75-H1 (SEQ ID NO:41), M75-H2 (SEQ ID NO:42), M75-H3 (SEQ ID NO:43), M75-H4 (SEQ ID NO:44), M75-H5 (SEQ ID NO:45) $V_H$Hs, (D) M79 (SEQ ID NO:46), M79-H0 (SEQ ID NO:47), m79-H1 (SEQ ID NO:48), M79-H2 (SEQ ID NO:49), M79-H3 (SEQ ID NO:50), M79-H4 (SEQ ID NO:51), M79-H5 (SEQ ID NO:52) $V_H$Hs are provided.

FIG. 2B provides sequences of wild-type serum albumin binding $V_H$Hs and their humanized variants. The sequences of isolated (llama, wild-type) and humanized $V_H$Hs are shown. The international ImMunoGeneTics information (IMGT) numbering system is used to distinguish framework regions (FRs) and complementarity determining regions (CDRs). The sequences of (E) H18 (SEQ ID NO:53), H18-H0 (SEQ ID NO:54), H18-H1 (SEQ ID NO:55), H18-H2 (SEQ ID NO:56), H18-H3 (SEQ ID NO:57), H18-H4 (SEQ ID NO:58), H18-H5 (SEQ ID NO:59) $V_H$Hs, (F) Rh34 (SEQ ID NO:60), Rh34-H0 (SEQ ID NO:61), Rh34-H1 (SEQ ID NO:62), Rh34-H2 (SEQ ID NO:63), Rh34-H3 (SEQ ID NO:64), Rh34-H4 (SEQ ID NO:65), Rh34-H5 (SEQ ID NO:66), $V_H$Hs, and (G) Rh46 (SEQ ID NO:67), Rh46-H0 (SEQ ID NO:68), Rh46-H1 (SEQ ID NO:69), Rh46-H2 (SEQ ID NO:70), Rh46-H3 (SEQ ID NO:71), Rh46-H4 (SEQ ID NO:72), Rh46-H5 (SEQ ID NO:73) $V_H$Hs are provided.

DETAILED DESCRIPTION

Figure 1:
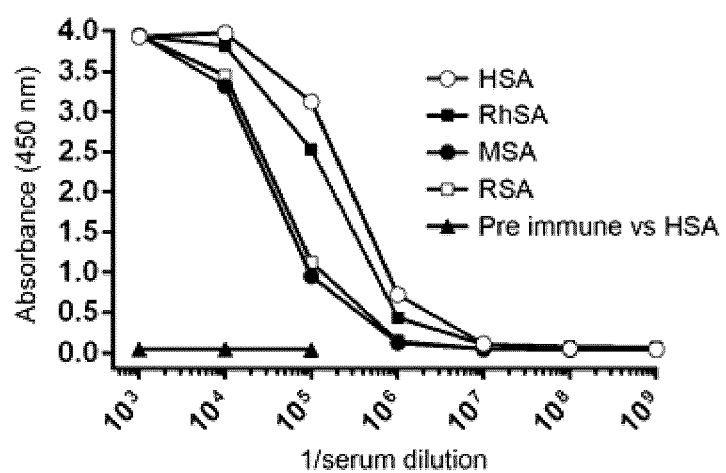
FIG. 1 illustrates the results from immunization of a llama in order to generate serum albumin binding single domain antibodies ($V_H$Hs). An ELISA shows the llama serum response to various serum albumins day 42 post immunization with human serum albumin (HSA). Pre-immune serum drawn before the first immunization is shown as a control. RhSA: rhesus serum albumin; MSA: mouse serum albumin; RSA: rat serum albumin.

The present invention is directed to a technology for extending the serum half-life of biologics, or increasing the rate of removal and neutralization of harmful molecules. In embodiments there is disclosed an antibody or an antigen-binding fragment that binds to serum albumin comprising four framework regions (FR1 to FR4) and three complementarity determining regions (CDR1, CDR2 and CDR3). According to an embodiment, the antibody or an antigen binding fragment may be a single domain antibody (sdAb) that binds to serum albumin comprising four framework regions (FR1 to FR4) and three complementarity determining regions (CDR1, CDR2 and CDR3).

The CDR1, CDR2 and CDR3 of the invention may comprise any one of the following amino acid sequence:

1)
GFLLRSNTM, (SEQ ID NO: 1)

IRPSGLT, (SEQ ID NO: 2)
and

HTRPPFQRDS (SEQ ID NO: 3)
or

ATRPPFQRDS, (SEQ ID NO: 4)
respectively; or

-continued

2)

GRTFIAYAM, (SEQ ID NO: 5)

ITNFAGGTT, (SEQ ID NO: 6)
and

AADRSAQTMRQVRPVLPY, (SEQ ID NO: 7)
respectively; or

3)

GRTFDNYVM, (SEQ ID NO: 8)

ISGSGSIT, (SEQ ID NO: 9)
and

AAGSRRTYYREPKFYPS, (SEQ ID NO: 10)
respectively; or

4)

GSTFSSSSV, (SEQ ID NO: 11)

ITSGGST, (SEQ ID NO: 12)
and

NVAGRNWVPISRYSPGPY (SEQ ID NO: 13)
or

AVAGRNWVPISRYSPGPY, (SEQ ID NO: 14)
respectively; or

5)

GSIESINRM, (SEQ ID NO: 15)

ISKGGST, (SEQ ID NO: 16)
and

AAGPVWEQF, (SEQ ID NO: 17)
respectively; or

6)

GRTISLYAV, (SEQ ID NO: 18)

ISWTDSST, (SEQ ID NO: 19)
and

AADVSIRGLQKYEYDY, (SEQ ID NO: 20)
respectively; or

7)

TRTFSSYIM, (SEQ ID NO: 21)

ISWSGRMT, (SEQ ID NO: 22)
and

AADRTTAWGAPRSQYDS, (SEQ ID NO: 23)
respectively.

Figure 2B:
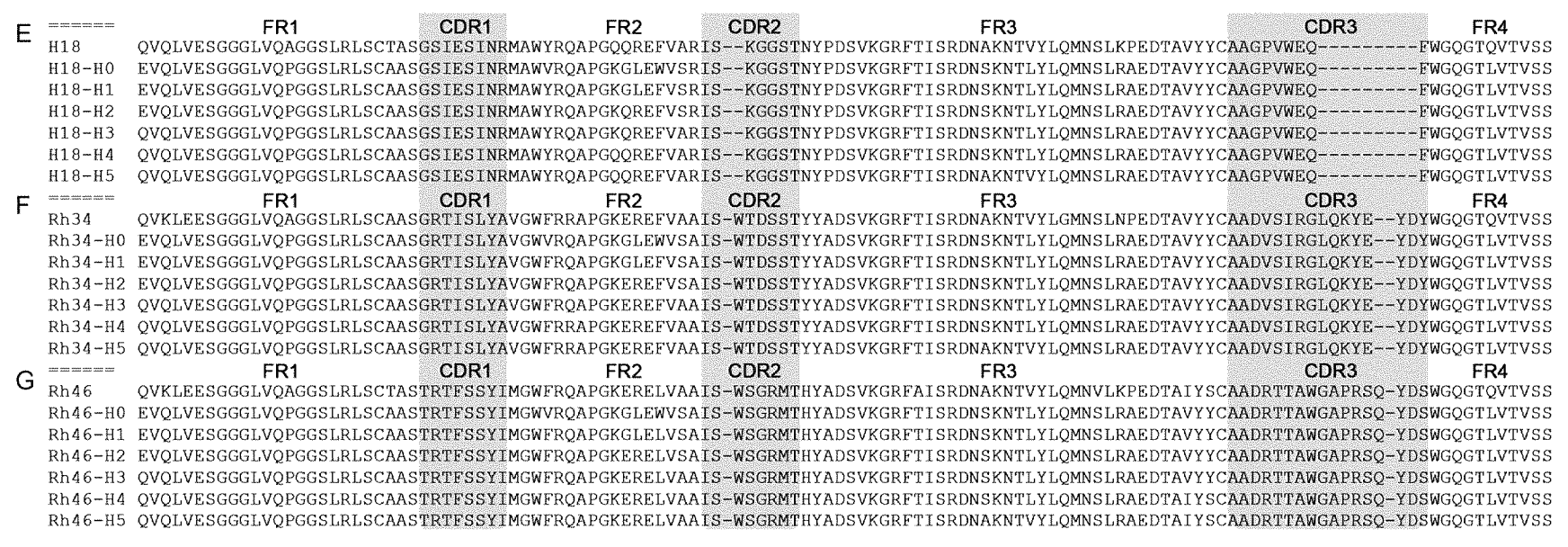

According to embodiments, the sdAb of the present invention may be the R11 sdAb (SEQ ID NO:24), and humanized versions thereof (H0 to H6) SEQ ID NOS:25-31); the R28 sdAb (SEQ ID NO:32), and humanized versions thereof (H0 to H5) SEQ ID NOS:33-38); the M75 sdAb (SEQ ID NO:39), and humanized versions thereof (H0 to H5) SEQ ID NOS:40-45); the M79 sdAb (SEQ ID NO:46), and humanized versions thereof (H0 to H5) SEQ ID NOS:47-52); the H18 sdAb (SEQ ID NO:53), and humanized versions thereof (H0 to H5) SEQ ID NOS:54-59); the Rh34 sdAb (SEQ ID NO:60), and humanized versions thereof (H0 to H5) SEQ ID NOS:61-66); and the Rh46 sdAb (SEQ ID NO:67), and humanized versions thereof (H0 to H5) SEQ ID NOS:68-73). See Tables 1 to Tables 3 below, and FIGS. 2A and 2B.

TABLE 1

Wild-type $V_HH$ affinities for serum albumins from various species.

| $V_HH$ | $K_D$ (nM) at pH 7.4 | | | | $K_D$ (nM) at pH 5.5 | | | | h-FcRn blocking? |
|---|---|---|---|---|---|---|---|---|---|
| | HSA | RhSA | RSA | MSA | HSA | RhSA | RSA | MSA | |
| R11 | 93 | 159 | 22 | 14[#] | 29 | 116 | 30 | — | No |
| R28 | 12 | 38 | 0.4 | 160 | 1.8 | 6 | 0.3 | — | No |
| M75 | 1.2 | 2.9 | 315 | 510 | 735 | — | n.b. | — | — |
| M79 | 122 | 85 | 13 | 406[#] | 7 | 2 | 7 | — | No |
| H18 | 34 | 48 | n.b. | — | 46 | 42 | n.b. | — | No |
| Rh34 | 286 | 333 | n.b. | — | 129 | 167 | n.b. | — | No |
| Rh46 | 80 | 81 | n.b. | — | 41 | 30 | n.b. | — | No |

Unless noted, all values were determined by single cycle kinetic (SCK) SPR measurements on a Biacore T200
[#]determined by ITC
"—": not determined
n.b.: no binding
HSA: human serum albumin
RhSA: rhesus serum albumin
RSA: rat serum albumin
MSA: mouse serum albumin
h-FcRn: human neonatal Fc receptor

TABLE 2

In vivo serum half-lives of various anti-serum albumin $V_HH$-fusions in rat

| Fusion protein description | Name | Serum $T_{1/2}$ (h)* |
|---|---|---|
| Monovalent $V_HH$ + anti-serum albumin $V_HH$ | B39 control | ~0.5[α] |
| | B39-A20.1 control | 1.4 |
| | B39-R11 | 46.1 |
| | B39-R28 | 31.1 |
| | B39-M75 | 4.3 |
| | B39-M79 | 31.9 |
| Biparatopic $V_HH$-$V_HH$ + anti-serum albumin $V_HH$ | A20-A26 control | 1.8 |
| | A20-A26-M75 | 6.8 |
| | A20-A26-M79 | 45.0 |
| Growth factor binding protein + anti-serum albumin $V_HH$ | CIBP2 control | n.d.[#] |
| | CIBP2-M75 | 4.9[#] |
| | CIBP2-M79 | 40.3[#] |
| BBB carrier $V_HH$ + peptide + anti-serum albumin $V_HH$ | FC5-ABP control | 1.1[α,#] |
| | FC5-ABP-M75 | 0.5[α,#] |
| | FC5-ABP-M79 | 25.4[#] |
| Enzyme + anti-serum albumin $V_HH$ | IDS-C1 control (140 nmol/kg) | 0.9[α,#] |
| | IDS-R28 (80 nmol/kg) | 2.8[#] |
| | IDS-M79 (80 nmol/kg) | 3.1[#] |
| | IDS-R28 (160 nmol/kg) | 4.4[#] |
| | IDS-M79 (160 nmol/kg) | 3.6[#] |
| Monovalent $V_HH$ + humanized anti-serum albumin $V_HH$ | B39-M75-H1 | 3.8 |
| | B39-R28-H5 | 51.2 |
| | B39-R11-H6 | 41.4 |

*Mean serum $T_{1/2}$ (terminal half-life, in h, unless otherwise noted), from n = 3 rats per group, determined by non-compartmental analysis using PK Solver v2.0 (Zhang et al, 2010).
[α]alpha half-life, β half-life could not be determined
[#]determined by MRM analysis
BBB: blood brain barrier
n.d.: could not be determined

TABLE 3

Biophysical characteristics of wild-type and humanized anti-serum albumin $V_HH_S$.

| $V_HH$ | # positions humanized | Yield[1] (mg) | SEC (%) main peak[2] | Stability (SEC, % main peak)[3] | $T_m$(° C.) ±SEM[4] | $K_D$HSA (nM)[5] | $K_D$RhSA (nM)[5] | $K_D$RSA (nM)[5] | $K_D$HSA (nM)[6] | $K_D$RhSA (nM)[6] | $K_D$RSA (nM)[6] |
|---|---|---|---|---|---|---|---|---|---|---|---|
| R11 | 0 | 5.25 | 94.3 | 98.2 | 69.64 ± 0.09 | 93.1 | 159 | 61.7 | 28.9 | 116 | 29.9 |
| R11-H0 | 19 | 0.38 | — | — | — | — | — | — | — | — | — |
| R11-H1 | 17 | 0.46 | 85.8 | 93.8 | — | n.b. | n.b. | n.b. | — | — | — |
| R11-H2 | 16 | 0.85 | 50.6 | — | — | n.b. | n.b. | n.b. | — | — | — |
| R11-H3 | 14 | 1.87 | 96.0 | 99.0 | 61.64 ± 0.09 | c.b. | c.b. | c.b. | — | — | — |
| R11-H4 | 12 | 6.37 | 96.5 | 98.5 | 68.58 ± 0.07 | c.b. | c.b. | c.b. | — | — | — |
| R11-H5 | 10 | 3.89 | 96.3 | 93.2 | 65.16 ± 0.11 | 307 | 643 | 196 | 98.2 | 525 | 160 |
| R11-H6 | 8 | 7.06 | 96.3 | 99.1 | 67.47 ± 0.09 | 252 | 561 | 151 | 67.5 | 511 | 123 |
| R28 | 0 | 5.50 | 95.4 | 90.2 | 71.56 ± 0.20 | 12.1 | 38.2 | 0.4 | 1.8 | 5.9 | 0.3 |
| R28-H0 | 15 | 0.09 | — | — | — | — | — | — | — | — | — |
| R28-H1 | 13 | 1.77 | 85.3 | 96.6 | 66.13 ± 0.12 | 162 | 2710 | 5.3 | 15.2 | 28.7 | 6.5 |
| R28-H2 | 11 | 2.97 | 93.7 | 98.8 | 66.55 ± 0.14 | 147 | 2630 | 4.1 | 6.6 | 668 | 1 |
| R28-H3 | 9 | 7.43 | 95.5 | 96.6 | 70.88 ± 0.08 | 51.3 | 625 | 2.4 | 47.2 | 1270 | 1.8 |
| R28-H4 | 7 | 1.98 | 89.5 | 80.9 | 66.84 ± 0.23 | 11.5 | 1740 | 1.1 | 51.6 | 341 | 5.3 |
| R28-H5 | 6 | 4.49 | 95.8 | 93.5 | 68.12 ± 0.26 | 11.1 | 145 | 0.4 | 2 | 7.3 | 3.5 |
| M75 | 0 | 5.88 | 96.9 | 93.5 | 79.77 ± 0.07 | 1.2 | 2.9 | 315 | 735 | n.b | n.b. |
| M75-H0 | 15 | 0.43 | — | — | — | — | — | — | — | — | — |
| M75-H1 | 13 | 5.82 | 97.9 | 97.0 | 78.03 ± 0.08 | 3.2 | 6.1 | 659 | — | — | — |
| M75-H2 | 11 | 6.23 | 94.4 | 96.9 | 73.16 ± 0.13 | 7.8 | 63.6 | 2490 | — | — | — |
| M75-H3 | 9 | 5.53 | 93.5 | 99.1 | 78.61 ± 0.08 | 4.8 | 17.7 | 1260 | — | — | — |
| M75-H4 | 7 | 5.46 | 95.9 | 97.7 | 75.98 ± 0.09 | 2.8 | 6.7 | 377 | — | — | — |
| M75-H5 | 5 | 5.78 | 94.2 | 99.0 | 80.88 ± 0.07 | 2.1 | 4.6 | 62.4 | — | — | — |
| M79 | 0 | 9.83 | 98.1 | 98.2 | 67.16 ± 0.09 | 122 | 84.6 | 12.6 | 7.1 | 2.0 | 7.1 |
| M79-H0 | 19 | 0.27 | — | — | — | — | — | — | — | — | — |
| M79-H1 | 17 | 0.27 | — | — | — | — | — | — | — | — | — |
| M79-H2 | 16 | 8.20 | 96.7 | 98.5 | 63.26 ± 0.09 | 76.2 | 62.1 | 10.4 | 6.5 | 2.6 | 5.9 |
| M79-H3 | 14 | 4.99 | 98.7 | 99.2 | 60.94 ± 0.09 | 53.3 | 36.7 | 8.7 | 9.6 | 2.9 | 12.2 |
| M79-H4 | 11 | 7.63 | 98.3 | 95.7 | 64.66 ± 0.08 | 58.9 | 38.7 | 10 | 8.4 | 2.9 | 8.8 |
| M79-H5 | 9 | 8.20 | 98.1 | 98.6 | 70.44 ± 0.12 | 103 | 86.5 | 20.2 | 8.1 | 4.2 | 6.6 |
| H18 | 0 | 8.38 | 98.0 | — | 72.76 ± 0.11 | 33.9 | 47.6 | n.b. | 46.2 | 42.2 | n.b. |
| H18-H0 | 14 | 0.11 | — | — | — | — | — | — | — | — | — |
| H18-H1 | 12 | 0.82 | 67.6 | — | 61.65 ± 0.14 | 52.8 | 91.5 | n.b. | 56.3 | 92.2 | n.b. |
| H18-H2 | 10 | 0.12 | — | — | — | — | — | — | — | — | — |
| H18-H3 | 8 | 10.54 | 93.5 | — | 69.52 ± 0.11 | 19.1 | 38.2 | n.b. | 22.3 | 57.6 | n.b. |
| H18-H4 | 7 | 10.84 | 92.3 | — | 68.92 ± 0.14 | 58.6 | 34.4 | n.b. | 57.1 | 72.7 | n.b. |
| H18-H5 | 5 | 12.03 | 92.3 | — | 69.60 ± 0.09 | 59.4 | 91.7 | n.b. | 46.6 | 70.7 | n.b. |
| Rh34 | 0 | 0.65 | 91.6 | — | agg | 286 | 333 | n.b. | 129 | 167 | n.b. |
| Rh34-H0 | 16 | 0.04 | — | — | — | — | — | — | — | — | — |
| Rh34-H1 | 14 | 0.53 | 63.8 | — | — | 824 | 1350 | n.b. | 1560 | 1920 | n.b. |
| Rh34-H2 | 12 | 2.56 | 76.0 | — | — | 1330 | 1470 | n.b. | 2320 | 3080 | n.b. |
| Rh34-H3 | 10 | 3.71 | 86.3 | — | — | 1370 | 1260 | n.b. | 2310 | 1810 | n.b. |
| Rh34-H4 | 9 | 1.61 | 92.1 | — | — | 647 | 739 | n.b. | 974 | 2250 | n.b. |
| Rh34-H5 | 7 | 2.53 | 94.1 | — | — | 410 | 589 | n.b. | 524 | 1420 | n.b. |
| Rh46 | 0 | 4.25 | 97.5 | — | 65.38 ± 0.04 | 80.1 | 80.8 | n.b. | 41.3 | 29.6 | n.b. |
| Rh46-H0 | 19 | 0.08 | — | — | — | — | — | — | — | — | — |
| Rh46-H1 | 17 | 5.15 | 95.2 | — | 66.29 ± 0.16 | 583 | 707 | n.b. | 97.7 | 40.8 | n.b. |
| Rh46-H2 | 15 | 9.83 | 96.6 | — | 67.44 ± 0.09 | 426 | 456 | n.b. | 87.3 | 44.1 | n.b. |
| Rh46-H3 | 13 | 10.13 | 94.1 | — | 72.44 ± 0.09 | 289 | 415 | n.b. | 70.3 | 34.0 | n.b. |
| Rh46-H4 | 11 | 6.95 | 94.8 | — | 67.55 ± 0.12 | 237 | 405 | n.b. | 51.5 | 25.2 | n.b. |
| Rh46-H5 | 9 | 14.26 | 94.6 | — | 69.31 ± 0.10 | 233 | 343 | n.b. | 54.9 | 24.1 | n.b. |

[1] Purified mg of $V_HH$ from 250 mL *E. coli* cultures (periplasmic extraction, IMAC purification)
[2] SEC monomer peak area after IMAC purification of $V_HH_S$ (Superdex 75 Increase column, 0.5 mL/min, HBS-EP buffer)
[3] SEC monomer peak area after 4 week storage of peak fractions from[2] at 4° C. (Superdex 75 Increase column, 0.5 mL/min, HBS-EP buffer)
[4] Determined by circular dichroism spectroscopy unfolding at 210 nm (25-106° C., 1° C./min, 100 mM NaPi buffer)
[5] SPR performed at pH 7.4, using single-cycle kinetic measurements on a Biacore T200
[6] SPR performed at pH 5.5, using single-cycle kinetic measurements on a Biacore T200
HSA: human serum albumin
RhSA: rhesus serum albumin
RSA: rat serum albumin
"—": not determined
n.b.: no binding by SPR
c.b.: complex binding by SPR, data not analyzable
agg: aggregation upon heating, $T_m$ not determined According to other embodiments, the antibody or an antigen-binding fragment of the present invention may be sdAb having sequences substantially identical to sdAb R11, R28, M75, M79, H18, Rh34 and Rh46, operable to bind to serum albumin from multiple species, including, but not limited to, human, monkey, rat, and mouse. A substantially identical sequence may comprise one or more conservative amino acid mutations. It is known in the art that one or more conservative amino acid mutation to a reference sequence may yield a mutant peptide with no substantial change in physiological, chemical, physico-chemical or functional properties compared to the reference sequence; in such a case, the reference and mutant sequences would be considered "substantially identical" polypeptides. A conservative amino acid substitution is defined herein as the substitution of an amino acid residue for another amino acid residue with similar chemical properties (e.g. size, charge, or polarity). According to one embodiment, these conservative amino acid mutations may be made to the framework regions of the sdAb while maintaining the CDR sequences listed above and the overall structure of the CDR of the antibody or fragment; thus the specificity and binding of the antibody are maintained. According to another embodiment, these conservative amino acid mutations may be made to the framework regions of the sdAb and the CDR sequence listed above while maintaining the antigen-binding function of the overall structure of the CDR of the antibody or fragment; thus the specificity and binding of the antibody are maintained.

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), BLAST-P, Blast-N, or FASTA-N, or any other appropriate software that is known in the art.

The substantially identical sequences of the present invention may be at least 90% identical; in another example, the substantially identical sequences may be at least 90, 91, 92, 93, 94, 95, 96, 97, 98, 99, or 100% identical, or any percentage therebetween, at the amino acid level to sequences described herein. Importantly, the substantially identical sequences retain the activity and specificity of the reference sequence. In a non-limiting embodiment, the difference in sequence identity may be due to conservative amino acid mutation(s). In a non-limiting example, the present invention may be directed to an antibody or antigen-binding fragment comprising a sequence at least 95%, 98%, or 99% identical to that of the antibodies described herein.

The antibody or an antigen-binding fragment of the present invention may be used for example to improve the half-life of the compounds in serum, by targeting an albumin moiety. As used herein, the expression "targeting an albumin moiety" is intended to mean that the antibody or an antigen-binding fragment of the present invention are enabled to bind to serum albumin and particularly to human, rhesus, mouse and rat serum albumin.

The term "antibody", also referred to in the art as "immunoglobulin" (Ig), as used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H1$, $C_H2$, $C_H3$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen-binding determinants of the molecule, and thus determines the specificity of an antibody for its target antigen. The majority of sequence variability occurs in six hypervariable regions, three each per variable heavy ($V_H$) and light ($V_L$) chain; the hypervariable regions combine to form the antigen-binding site, and contribute to binding and recognition of an antigenic determinant. The specificity and affinity of an antibody for its antigen is determined by the structure of the hypervariable regions, as well as their size, shape, and chemistry of the surface they present to the antigen. Various schemes exist for identification of the regions of hypervariability, the two most common being those of Kabat and of Chothia and Lesk. Kabat and Wu (1991) define the "complementarity-determining regions" (CDR) based on sequence variability at the antigen-binding regions of the $V_H$ and $V_L$ domains. Chothia and Lesk (1987) define the "hypervariable loops" (H or L) based on the location of the structural loop regions in the $V_H$ and $V_L$ domains. These individual schemes define CDR and hypervariable loop regions that are adjacent or overlapping, those of skill in the antibody art often utilize the terms "CDR" and "hypervariable loop" interchangeably, and they may be so used herein. The CDR/loops are identified herein according to the IMGT nomenclature scheme (i.e., CDR1, 2 and 3, for each variable region).

An "antibody fragment" or "antigen-binding fragment" as referred to herein may include any suitable antigen-binding antibody fragment known in the art. The antibody fragment may be a naturally-occurring antibody fragment, or may be obtained by manipulation of a naturally-occurring antibody or by using recombinant methods. For example, an antibody fragment may include, but is not limited to a Fv, single-chain Fv (scFv; a molecule consisting of $V_L$ and $V_H$ connected with a peptide linker), Fab, F(ab)$_2$, single-domain antibody (sdAb; a fragment composed of a single $V_L$ or $V_H$ or a $V_H$H), and multivalent presentations of any of these. Antibody fragments such as those just described may require linker sequences, disulfide bonds, or other type of covalent bond to link different portions of the fragments; those of skill in the art will be familiar with the requirements of the different types of fragments and various approaches and various approaches for their construction.

In a non-limiting example, the antigen-binding fragment of the present invention may be an sdAb derived from naturally-occurring sources (i.e. in effect, an additional sdAb as the albumin binding sdAb of the present invention). Heavy chain antibodies of camelid origin (Hamers-Casterman et al, 1993) lack light chains and thus their antigen binding sites consist of one domain, termed $V_HH$. SdAbs have also been observed in shark and are termed $V_{NAR}$ (Nuttall et al, 2003). Other sdAbs may be engineered based on human Ig heavy and light chain sequences (Jespers et al, 2004; To et al, 2005). As used herein, the term "sdAb" includes those sdAb directly isolated from $V_H$, $V_HH$, $V_L$, or $V_{NAR}$ reservoir of any origin through phage display or other technologies, sdAb derived from the aforementioned sdAb, recombinantly produced sdAb, as well as those sdAb generated through further modification of such sdAb by humanization, affinity maturation, stabilization, solubilization, camelization, or other methods of antibody engineering. Also encompassed by the present invention are homologues, derivatives, or fragments that retain the antigen-binding function and specificity of the sdAb.

SdAbs possess desirable properties for antibody molecules, such as high thermostability, high detergent resistance, relatively high resistance to proteases (Dumoulin et al, 2002) and high production yield (Arbabi-Ghahroudi et al, 1997); they can also be engineered to have very high affinity by isolation from an immune library (Li et al, 2009) or by in vitro affinity maturation (Davies & Riechmann, 1996). Further modifications to increase stability, such as the introduction of non-canonical disulfide bonds (Hussack et al, 2011a,b; Kim et al, 2012), may also be brought to the sdAb.

A person of skill in the art would be well-acquainted with the structure of a single-domain antibody (see, for example, 3DWT, 2P42 in Protein Data Bank). An sdAb comprises a single immunoglobulin domain that retains the immunoglobulin fold; most notably, only three CDR/hypervariable loops form the antigen-binding site. However, and as would be understood by those of skill in the art, not all CDR may be required for binding the antigen. For example, and without wishing to be limiting, one, two, or three of the CDR may contribute to binding and recognition of the antigen by the sdAb of the present invention. The CDR of the sdAb or variable domain are referred to herein as CDR1, CDR2, and CDR3.

The present invention further encompasses an antibody or an antigen-binding fragment that is "humanized" using any suitable method known in the art, for example, but not limited to CDR grafting and veneering. Humanization of an antibody or an antigen-binding fragment comprises replacing an amino acid in the sequence with its human counterpart, as found in the human consensus sequence, without loss of antigen-binding ability or specificity; this approach reduces immunogenicity of the antibody or antigen-binding fragment when introduced into human subjects. In the process of CDR grafting, one or more than one of the CDR defined herein may be fused or grafted to a human variable region ($V_H$, or $V_L$), to other human antibody (IgA, IgD, IgE, IgG, and IgM), to other human antibody fragment framework regions (Fv, scFv, Fab) or to other proteins of similar size and nature onto which CDR can be grafted (Nicaise et al, 2004). In such a case, the conformation of the one or more than one hypervariable loop is likely preserved, and the affinity and specificity of the antibody or an antigen-binding fragment for its target (i.e., human/rhesus/rat/mouse serum albumin, collectively referred to as serum albumin) is likely minimally affected. CDR grafting is known in the art and is described in at least the following: U.S. Pat. Nos. 6,180,370, 5,693,761, 6,054,297, 5,859,205, and European Patent No. 626390. Veneering, also referred to in the art as "variable region resurfacing", involves humanizing solvent-exposed positions of the antibody or fragment; thus, buried nonhumanized residues, which may be important for CDR conformation, are preserved while the potential for immunological reaction against solvent-exposed regions is minimized. Veneering is known in the art and is described in at least the following: U.S. Pat. Nos. 5,869,619, 5,766,886, 5,821,123, and European Patent No. 519596. Persons of skill in the art would also be amply familiar with methods of preparing such humanized antibody fragments and humanizing amino acid positions.

The antibody or an antigen-binding fragment used with the present invention may also comprise additional sequences to aid in expression, detection or purification of a recombinant antibody or an antigen-binding fragment. Any such sequences or tags known to those of skill in the art may be used. For example, and without wishing to be limiting, the antibody or antigen-binding fragment may comprise a targeting or signal sequence (for example, but not limited to ompA or pelB), a detection/purification tag (for example, but not limited to c-Myc, HA, HisS, or His6), or a combination thereof. In another example, the additional sequence may be a biotin recognition site such as that described by Cronan et al in WO 95/04069 or Voges et al in WO/2004/076670. As is also known to those of skill in the art, linker sequences may be used in conjunction with the additional sequences or tags, or may serve as a detection/purification tag.

In another embodiment, there is disclosed a compound comprising antibody or an antigen-binding fragment according to the present invention. In embodiments, the antibody or an antigen-binding fragment of the compound may be linked to the remainder of the compound via a linker (also known as a linker sequence. As known to those of skill in the art, linker sequences may be used in conjunction with the antibody or antigen-binding fragment of the present invention of the compound of the present invention. As used herein, the term "linker sequences" is intended to mean short peptide sequences that occur between protein domains. Linker sequences are often composed of flexible residues like glycine and serine so that the adjacent protein domains are free to move relative to one another. The linker sequence can be any linker sequence known in the art that would allow for the antibody and polypeptide of a compound, of the present invention to be operably linked for the desired function. The linker may be any sequence in the art (either a natural or synthetic linker) that allows for an operable fusion comprising an antibody or fragment linked to a polypeptide. For example, the linker sequence may be a linker sequence L such as $(GGGGS)_n$, wherein n equal to or greater than 1, or from about 1 to about 5, or from about 1 to 15, or n may be any number of linker that would allow for the operability of the compound of the present invention. In another example, the linker may be an amino acid sequence, for example, an amino acid sequence that comprises about 3 to about 40 amino acids, or about 5 to about 40 amino acids, or about 10 to about 40 amino acids, or about 15 to about 40 amino acids, or about 20 to about 40 amino acids, or about 25 to about 40 amino acids, or about 30 to about 40 amino acids, or about 35 to about 40 amino acids, or about 3 to about 35 amino acids, or about 5 to about 35 amino acids, or about 10 to about 35 amino acids, or about 15 to about 35 amino acids, or about 20 to about 35 amino acids, or about 25 to about 35 amino acids, or about 30 to about 35 amino acids, or about 3 to about 30 amino acids, or about 5 to about 30 amino acids, or about 10 to about 30 amino acids, or about 15 to about 30 amino acids, or about 20 to about 30 amino acids, or about 25 to about 30 amino acids, or about 3 to about 25 amino acids, or about 5 to about 25 amino acids, or about 10 to about 25 amino acids, or about 15 to about 25 amino acids, or about 20 to about 25 amino acids, or about 3 to about 20 amino acids, or about 5 to about 20 amino acids, or about 10 to about 20 amino acids, or about 15 to about 20 amino acids, or about 3 to about 15 amino acids, or about 5 to about 15 amino acids, or about 10 to about 15 amino acids, or about 15 to about 20 amino acids, or about 3 to about 10 amino acids, or about 5 to about 10 amino acids, or about 3 to about 5 amino acids, or about 3, 5, 10, 15, 20, 25, 30, 35, or 40 amino acids.

According to an embodiment, the antibody or an antigen-binding fragment of the compound may be fused to any one of a peptide, polypeptide (e.g. growth factor CIBP2, antimicrobial cyclic peptides), a protein, an enzyme or polypeptide [such as for example iduronate-2-sulfatase (IDS), acid beta-glucosidase (GCase), serine proteases, growth factors], an antibody or a fragment operable to bind a target epitope (e.g. anti-microbial antibodies, anti-inflammatory antibodies, intrabodies, BBB-crossing antibodies, neurodegeneration targets antibodies, ion channel targeting antibodies for pain, imaging, diagnostic, affinity purification reagents, anti-cancer targets, checkpoint inhibitors, GPCR targeting antibodies), or combinations thereof, in which both the antibody or an antigen-binding fragment and the rest of the compound remain functional for their intended purpose. In a preferred embodiment, the compound may be fused to an antibody or an antigen-binding fragment, operable to bind a target epitope.

The antibody or antigen-binding fragment of the present invention may also be in a multivalent display format, also referred to herein as multivalent presentation. Multimerization may be achieved by any suitable method of known in the art. For example, and without wishing to be limiting in any manner, multimerization may be achieved using self-assembly molecules such as those described in Zhang et al (2004a; 2004b) and WO2003/046560, where pentabodies are produced by expressing a fusion protein comprising the antibody or antigen-binding fragment of the present invention and the pentamerization domain of the B-subunit of an AB5 toxin family (Merritt & Hol, 1995). A multimer may also be formed using the multimerization domains described by Zhu et al. (2010); this form, referred to herein as a "combody" form, is a fusion of the antibody or fragment of the present invention with a coiled-coil peptide resulting in a multimeric molecule (Zhu et al., 2010). Other forms of multivalent display are also encompassed by the present invention. For example, and without wishing to be limiting, the antibody or antigen-binding fragment may be presented as a dimer, a trimer, or any other suitable oligomer. This may be achieved by methods known in the art (Spiess et al, 2015), for example direct linking connection (Nielsen et al, 2000), c-jun/Fos interaction (de Kruif & Logtenberg, 1996), "Knob into holes" interaction (Ridgway et al, 1996).

Another method known in the art for multimerization is to dimerize the antibody or antigen-binding fragment using an Fc domain, for example, but not limited to human Fc domains. The Fc domains may be selected from various classes including, but not limited to, IgG, IgM, or various subclasses including, but not limited to IgG1, IgG2, etc. In this approach, the Fc gene in inserted into a vector along with the sdAb gene to generate a sdAb-Fc fusion protein (Bell et al, 2010; Iqbal et al, 2010); the fusion protein is recombinantly expressed then purified. For example, and without wishing to be limiting in any manner, multivalent display formats may encompass chimeric or humanized formats of antibodies $V_HH$ of the present invention linked to an Fc domain, or bi or tri-specific antibody fusions with two or three antibodies $V_HH$ recognizing unique epitopes. Such antibodies are easy to engineer and to produce, can greatly extend the serum half-life of sdAb, and may be excellent tumor imaging reagents (Bell et al., 2010).

The Fc domain in the multimeric complex as just described may be any suitable Fc fragment known in the art. The Fc fragment may be from any suitable source; for example, the Fc may be of mouse or human origin. In a specific, non-limiting example, the Fc may be the mouse Fc2b fragment or human Fc1 fragment (Bell et al, 2010; Iqbal et al, 2010). The Fc fragment may be fused to the N-terminal or C-terminal end of the $V_HH$ or humanized versions of the present invention.

Each subunit of the multimers described above may comprise the same or different antibodies or antigen-binding fragments of the present invention, which may have the same or different specificity. Additionally, the multimerization domains may be linked to the antibody or antigen-binding fragment using a linker, as required; such a linker should be of sufficient length and appropriate composition to provide flexible attachment of the two molecules, but should not hamper the antigen-binding properties of the antibody. As defined above, the linker sequence can be any linker known in the art that would allow for the compound of the present invention to be prepared and be operable for the desired function. For example, such a linker sequence should be of sufficient length and appropriate composition to provide flexible attachment of the two molecules, but should not hamper the antigen-binding properties of the antibody.

According to another embodiment, the present invention also encompasses a composition comprising one or more than one of the compound as described herein. The composition may comprise a single sdAb and/or compound as described above, or may be a mixture of sdAb or compounds. Furthermore, in a composition comprising a mixture of sdAb or compounds of the present invention, the sdAb or compound may have the same specificity, or may differ in their specificities; for example, and without wishing to be limiting in any manner, the composition may comprise sdAb or compounds specific to albumin (same or different epitope).

The composition may also comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in suspension form, powder form (for example, but limited to lyophilised or encapsulated), capsule or tablet form. For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH to ensure the viability of the antibody or antigen-binding fragment. Dry powders may also include additives to improve stability and/or carriers to increase bulk/volume;

for example, and without wishing to be limiting, the dry powder composition may comprise sucrose or trehalose. In a specific, non-limiting example, the composition may be so formulated as to deliver the antibody or antigen-binding fragment to the gastrointestinal tract of the subject. Thus, the composition may comprise encapsulation, time release, or other suitable technologies for delivery of the sdAb or compounds of the present invention. It would be within the competency of a person of skill in the art to prepare suitable compositions comprising the present sdAb or compounds.

The invention also encompasses nucleic acid vector comprising a nucleotide sequence encoding a sdAb or a compound of the present invention, as well as cells comprising the nucleic acid vector, for expressing the sdAb or compound of the present invention, and cells for expressing the sdAb or compound of the present invention.

According to another embodiment, there is provided a method of removing a molecule from serum, comprising administering a compound according to the present invention, specific to the molecule, wherein the sdAb comprises CDR1, CDR2 and CDR3 comprising an amino acid sequence comprising GRTFDNYVM (SEQ ID NO:8), ISGSGSIT (SEQ ID NO:9), and AAGSRRTYYREPKFYPS (SEQ ID NO:10), respectively.

According to another embodiment, there is provided a use of a compound according to the present invention which is specific to a molecule, for removing the molecule from serum, wherein the sdAb comprises CDR1, CDR2 and CDR3 comprising an amino acid sequence comprising GRTFDNYVM (SEQ ID NO:8), ISGSGSIT (SEQ ID NO:9), and AAGSRRTYYREPKFYPS (SEQ ID NO:10), respectively.

According to another embodiment, there is provided a solid support for purification of albumin, derivatives thereof, or fragments thereof comprising a solid or semi-solid medium linked to an antibody or an antigen-binding fragment according to the present invention or a compound according to any one of claims 12 to 15.

According to another embodiment, there is provided a method of purifying albumin comprising contacting an albumin containing sample with a solid support according to the present invention.

The present invention will be more readily understood by referring to the following examples which are given to illustrate the invention rather than to limit its scope.

Serum Albumin $V_H$H Isolation

Example 1

Llama Immunization

One male llama (*Lama glama*) was immunized by Cedarlane (Burlington, ON, Canada) four times with 100 µg of human serum albumin (HSA; Sigma, Oakville, ON, Canada) in 1 mL of phosphate-buffered saline (PBS), pH 7.4, emulsified in an equal volume of Freund's complete adjuvant for the priming immunization (day 0) or Freund's incomplete adjuvant for the boosting immunizations (days 21, 28 and 35). Pre-immune blood was drawn before the first injection on day 1 and served as a negative control. One week after the final immunization, serum and peripheral blood mononuclear cells (PBMCs) were obtained from the animal (day 42).

Example 2

Fractionation of Serum

Pre-immune and day 42 llama sera were fractionated by protein G and protein A chromatography (Hi Trap, GE Healthcare, Mississauga, ON, Canada) and eluted by acidic elution. Serum fractions A1 (HCAb), A2 (HCAb), G1 (HCAb), and G2 (cIgG) were neutralized with Tris pH 8.8 and dialyzed against PBS pH 7.4 for storage at 4° C. IgG serum fractions were measured using 1.3 $AbS_{280nm}$=1 mg/mL.

Example 3

ELISA of Whole and Fractionated Serum

Total serum (pre-immune and day 42), as well as the resulting fractionated sera, A1 (HCAb), A2 (HCAb), G1 (HCAb), and G2 (conventional IgG), were analyzed for specific binding to serum albumins from human, rhesus, rat and mouse (HSA, RhSA, MSA and RSA, respectively) by ELISA. Wells of NUNC MaxiSorp™ microtiter plates were coated overnight at 4° C. with 1.5 µg of each serum albumin in 100 µL PBS. The next day, wells were blocked with 300 µL of PBS containing 5% (w/v) skim milk and 0.05% (v/v) Tween-20 for 1.5 h at 37° C., then sera were diluted in PBS, added to wells and incubated for 1 h. Wells were washed 3× with PBS containing 0.1% Tween-20 (PBS-T), incubated with HRP-conjugated goat anti-llama IgG (Cedarlane) diluted to 1:10000 in PBS, then washed again 3× with PBS-T. Wells were developed with 100 µL of tetramethylbenzidine substrate (Mandel Scientific, Guelph, ON, Canada) then after 5 min, the reaction was stopped with 100 µL of 1 M H2SO4 and the absorbance at 450 nm was measured using a Multiskan™ FC photometer (Thermo-Fisher, Ottawa, ON, Canada)(FIG. 1).

Example 4

Library Construction

A phage-displayed $V_H$H library was constructed from the heavy-chain-only antibody repertoire of the immunized llama as described previously (Hussack et al, 2011a; Baral et al, 2013). Briefly, total cellular RNA was extracted from approximately 5×10$^7$ peripheral blood mononuclear cells (PBMCs) using a PureLink® RNA Mini Kit (Life Technologies, Carlsbad, Calif.), pooled, then reverse transcribed using SuperScript® VILO™ MasterMix (Life Technologies) as per the manufacturer's instructions. Rearranged $V_H$H genes were amplified using two rounds of semi-nested PCR and cloned into the pMED1 phagemid vector, and then phage were rescued from library-bearing *Escherichia coli* TG1 cells by superinfection with M13KO7 helper phage (Life Technologies) and purified by polyethylene glycol precipitation, essentially as previously described (Hussack et al, 2011a).

Example 5

Panning

The phage-displayed $V_H$H library was panned, essentially as described (Hussack et al, 2011a; Baral et al, 2013), for a single round simultaneously against HSA, RhSA, MSA and RSA immobilized in separate wells. Briefly, wells of NUNC MaxiSorp™ microtiter plates (Thermo-Fisher) were coated overnight at 4° C. with 5 µg of each serum albumin in 100 µL of PBS. The next day, wells were blocked for 1.5 h at 37° C. with 300 µL of PBS containing 5% (w/v) skim milk and 0.05% (v/v) Tween-20, then ~$10^{12}$ phage particles (diluted in 100 µL PBS containing 20% (v/v) SuperBlock™ (Life Technologies)) were applied to each well and incubated at room temperature for 2 h. The wells were washed five times with PBS containing 0.05% (v/v) Tween-20 (PBS-T), five times with PBS and then bound phage were eluted sequentially with 100 µL of 100 mM triethylamine followed by 100 µL of 100 mM glycine, pH 2.0. Both high and low pH phage elutions were neutralized with 50 µL of 1 M Tris.HCl, pH 8.0, pooled and titered. As a control, the library was panned against an antigen-free well containing only blocking solution.

Example 6

Next Generation DNA Sequencing

The original library phage and the phage eluted from each panning (HSA, RhSA, MSA and RSA) were used directly as templates for next generation sequencing (NGS). Approximately $10^6$ phage particles were used as template in 25 µL PCR reactions containing 1×ABI Buffer II, 1.5 mM $MgCl_2$, 200 µM each dNTP (Thermo-Fisher), 5 pmol each of primers NGS-MJ7 (5'CGCTCTTCC-GATCTCTGNNNNNGCCCAGCCGGCCATGGCC) and NGS-MJ8 (5'TGCTCTTCCGATCTGACNNNNNTGAG-GAGACGGTGACCTGG) and 1 U of AmpliTaq® Gold DNA polymerase (Life Technologies) and cycled as follows on an GeneAmp® PCR System 9700 thermal cycler (Applied BioSystems, Foster City, Calif.): 95° C. for 7 min; 35 cycles of (94° C. for 30 s, 55° C. for 45 s, and 72° C. for 2 min); 72° C. for 10 min. The resulting amplicons were purified using PureLink® PCR purification kits (Life Technologies) with a ≥300 bp size cutoff according to the manufacturer's instructions. Each sample was individually barcoded in a second "tagging" 50 µL PCR reaction containing 1× Phusion HF Buffer, 1.5 mM $MgCl_2$, 200 µM each dNTP, 10 pmol of each primer pair P5-seqF (5'AATGA-TACGGCGACCACCGAGATCTACACTCTTTCCCTA-CACGACGCTCT TCCGATCTCTG) and P7-index1-seqR (5' CAAGCAGAAGACGGCATACGAGATCGT-GATGTGACTGGAGTTCAGACGTGT GCTCTTCC-GATCTGAC) sequences. 0.25 U Phusion High-Fidelity DNA polymerase (Thermo-Fisher) and 5 µL first-round PCR as template, then cycled as follows: 98° C. for 30 s; 20 cycles of (98° C. for 10 s, 65° C. for 30 s, and 72° C. for 30 s); 72° C. for 5 min. The final five amplicons (derived from library phage, HSA output phage, RhSA output phage, MSA output phage and RSA output phage) were pooled and purified from 1% (w/v) agarose gels using a QIAquick® gel extraction kit (QIAGEN, Toronto, ON, Canada), desalted using Agencourt AMPure XP beads (Beckman-Coulter, Pasadena, Calif.), then sequenced on a MiSeq Sequencing System (Illumina, San Diego, Calif.) using a 500-cycle MiSeq Reagent Kit V2 and a 5% PhiX genomic DNA spike. From each sample, 1.8-2.4 million reads were generated, of which 0.4-1.2 million were used for analysis after assembly using FLASH (default parameters; (Magoc and Salzberg, 2011) and quality filtering using the FAST-X toolkit with a stringency of Q30 over 95% of each read (Schmieder and Edwards, 2011). The DNA sequence of each $V_H H$ was then translated in silico, and the CDR3 sequence (IMGT positions 105-117) parsed using conserved N-terminal amino acid consensus sequences (YYC). For each panning, the set of CDR3 sequences derived from the output phage was compared to the set from the $V_H H$ library; for each shared CDR3 sequence, an enrichment score was calculated as the frequency in the output phage divided by the frequency in the library. This frequency score was used as a first-pass approximation of the binding behaviour of $V_H H s$ in the library and used for identification of putative serum albumin-binding $V_H H s$ with a range of predicted cross-species reactivity. A fold-enrichment of 10 was used as a cut-off for putative serum albumin binding.

Example 7

Subcloning Expression and Purification

The DNA sequences of seven $V_H$ Hs were synthesized commercially in the pSJF2 expression vector (GenScript, Piscataway, N.J.) and each construct was produced in *E. coli*. Briefly, 1 L 2×YT cultures containing 100 µg/mL ampicillin, 0.1% (w/v) glucose and 0.5 mM IPTG were inoculated with single plasmid-bearing *E. coli* TG1 colonies and grown overnight at 37° C. with 220 rpm shaking. The next morning, periplasmic proteins were extracted by osmotic shock. The resulting supernatant was dialyzed overnight into immobilized metal affinity chromatography buffer A (10 mM HEPES buffer pH7.0, 500 mM NaCl) and sterile filtered. Protein was purified by IMAC using 5 mL HiTrap™ Chelating HP IMAC columns (GE Healthcare), under the control of an ÄKTA™ Express (GE Healthcare). A stepwise gradient of 500 mM imidazole in the above buffer A was used for protein elution. Proteins were stored at 4° C.

Example 8

Phage ELISA and Soluble ELISA

Wells of NUNC MaxiSorp™ microtiter plates were coated overnight at 4° C. with 1.5 µg of each serum albumin in 100 µL PBS. The next day, wells were blocked with 300 µl of PBS containing 5% (w/v) skim milk and 0.05% (v/v) Tween-20 for 1.5 h at 37° C., then serially diluted $V_H H s$ or $V_H H$-bearing phage were added to wells and incubated for 1 h. Wells were washed 3× with PBS containing 0.1% Tween-20 (PBS-T), then incubated in either horseradish peroxidase (HRP)-conjugated rabbit anti-His6 (Cedarlane) or anti-M13 (GE Healthcare) secondary antibody, respectively, both at a dilution of 1:5,000, then washed again 3× with PBS-T and developed with 100 µL of tetramethylbenzidine substrate (Mandel Scientific, Guelph, ON, Canada). After 5 min, the reaction was stopped with 100 µL of 1 M $H_2SO_4$ and the absorbance at 450 nm was measured using a Multiskan™ FC photometer (Thermo-Fisher).

Example 9

Figure 3:
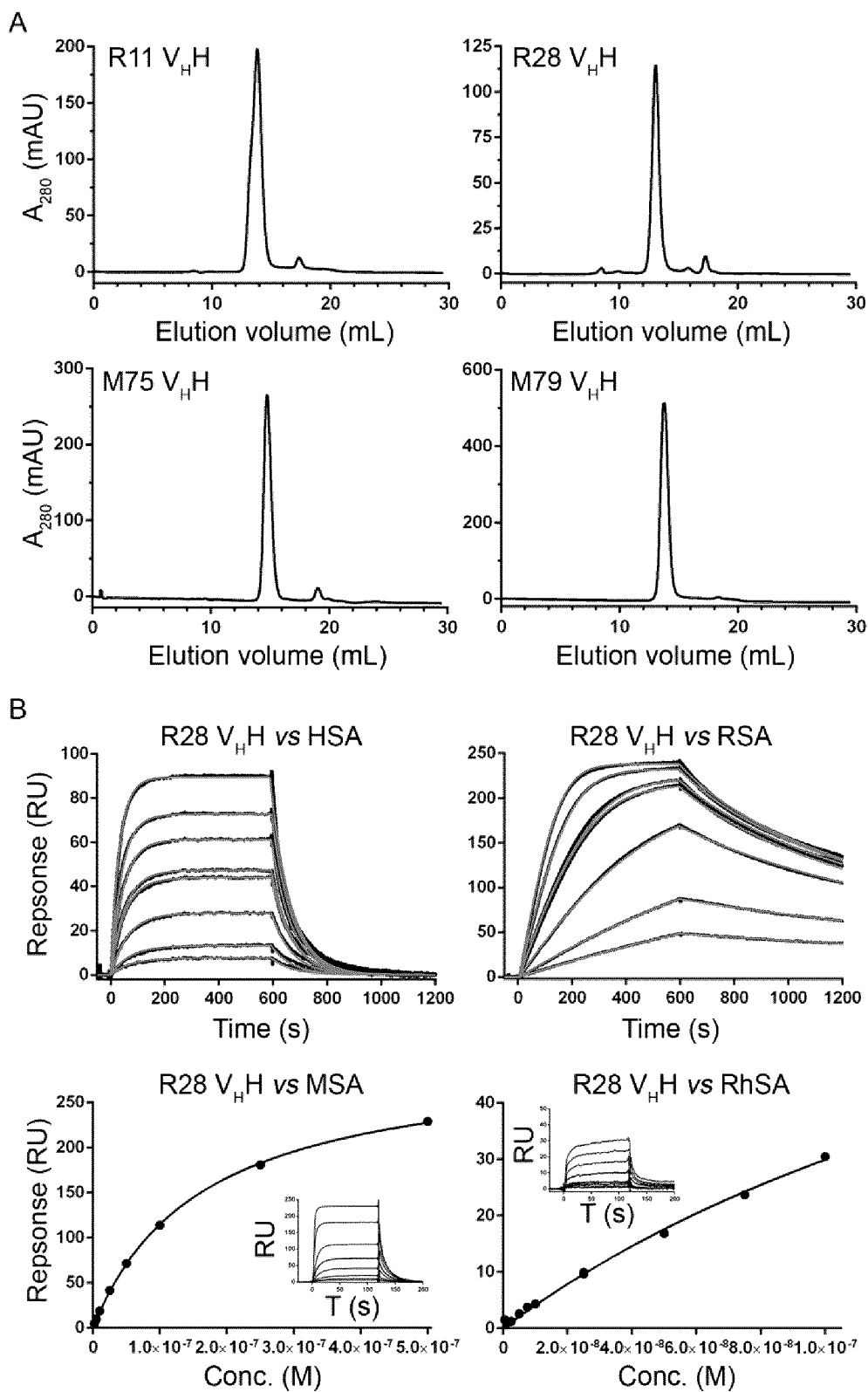
FIG. 3 illustrates the biophysical characterization of serum albumin binding $V_H$Hs. In this example, various assays are shown to characterize the $V_H$Hs. (A) Representative size exclusion chromatography (SEC) profiles illustrating the $V_H$Hs are strictly monomeric and non-aggregating. (B) Representative surface plasmon resonance (SPR) sensorgrams demonstrating the cross-reactive binding of $V_H$Hs to various serum albumins at pH 7.4. HSA: human serum albumin; RhSA: rhesus serum albumin; MSA: mouse serum albumin; RSA: rat serum albumin.

Size Exclusion Chromatography $V_H H s$ were purified by size exclusion chromatography (SEC) using a Superdex™ 75 10/300 GL column (GE Healthcare) under the control of an ÄKTA™-FPLC (GE Healthcare). Briefly 250-500 µg of sample were applied at a flow rate of 0.5 mL/min in a mobile phase that consisted of phosphate buffered saline (PBS pH 7.0). Fractions of 0.5 mL of monomeric $V_H H$ were collected. The results are shown in FIG. 3A.

Example 10

Isothermal Titration Calorimetry

ITC experiments were performed at 25° C. using a MicroCal Auto-ITC$_{200}$ (GE Healthcare). To avoid buffer artifacts all serum albumins and V$_H$Hs were buffer exchanged into PBS using SEC. Settings included 18 automatically defined injections of 2 µL over 5 s and a syringe stirring at 1000 rpm. Concentrations of 50 µM were used for the V$_H$H titrants in the syringe and concentrations of 5 µM of the various serum albumins were in the cell. Data analysis was performed with the Origin software package (GE Healthcare).

Example 11

SPR Binding Assays at pH 7.4

For SPR, a total of 1362-1471 resonance units of each serum albumin protein were immobilized in 10 mM acetate buffer, pH 4.5, on CM5 or CM5 series S sensor chips (GE Healthcare) using an amine coupling kit (GE Healthcare). Kinetic analyses were carried out on a Biacore 3000 or Biacore T200 instrument (GE Healthcare) at 25° C. by injecting V$_H$Hs at various concentration ranges, in HBS-EP+ buffer (10 mM HEPES buffer, pH 7.4 containing 150 mM NaCl, 3 mM EDTA and 0.005% (v/v) surfactant P20) and at a flow rate of 20 µL/min. Data were analyzed using BIAevaluation software version 4.1 (GE Healthcare) and fitted to a 1:1 binding model. Results are shown in FIG. 3B and Table 1.

Example 12

SPR Binding Assays at pH 5.5

Figure 4:
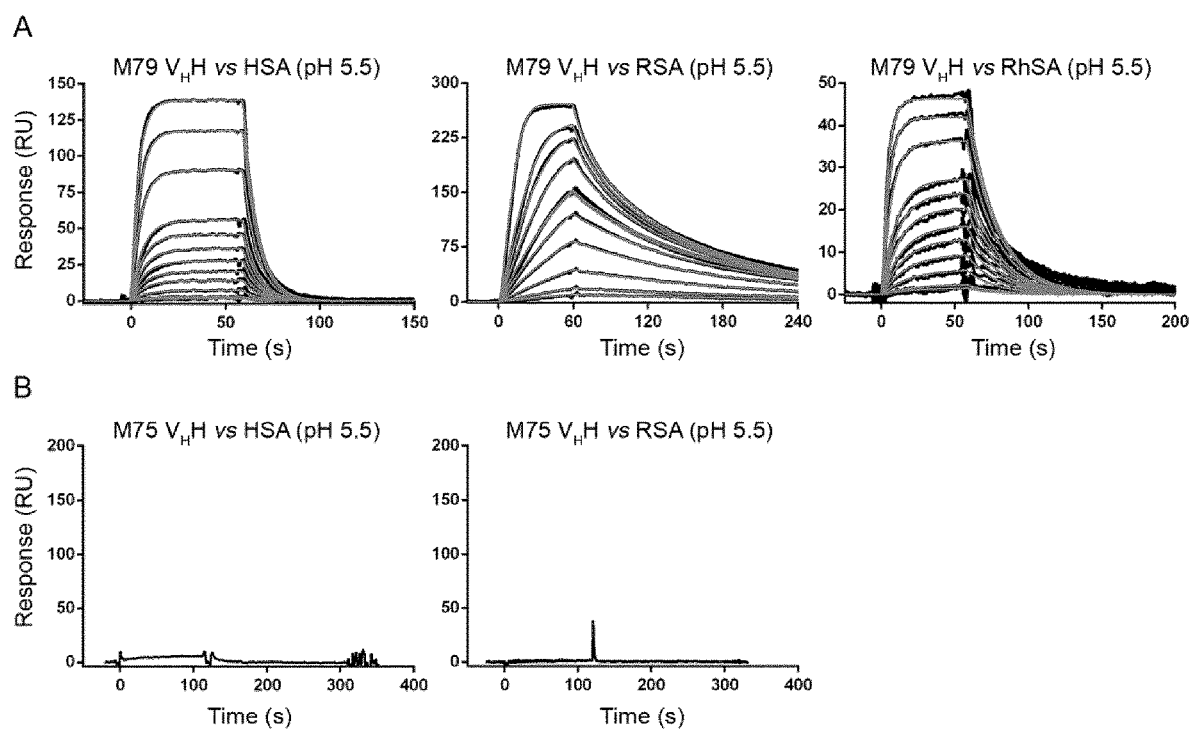
FIG. 4 illustrates the SPR binding analyses of serum albumin binding $V_H$Hs at pH 5.5. The representative SPR sensorgrams illustrate pH-sensitive binding to various serum albumins. (A) M79 $V_H$H binding to HSA, RSA and RhSA at pH 5.5. (B) M75 $V_H$H (at a 100 nM injection) very weakly binds HSA and does not recognize RSA at pH 5.5. HSA: human serum albumin; RhSA: rhesus serum albumin; RSA: rat serum albumin.

SPR experiments were repeated exactly as described above with the exception of the running buffer which was adjusted to pH 5.5 (HBSP-MES: 10 mM HEPES buffer, pH 5.5, 10 mM MES, 150 mM NaCl, 0.005% P20). SEC-purified fractions of monomeric V$_H$Hs were also buffer exchanged into the same pH 5.5 buffer before running the SPR experiments. The results are shown in FIGS. 4A, 4B and Table 1.

Example 13

SPR-Based Epitope Binning

Figure 5:
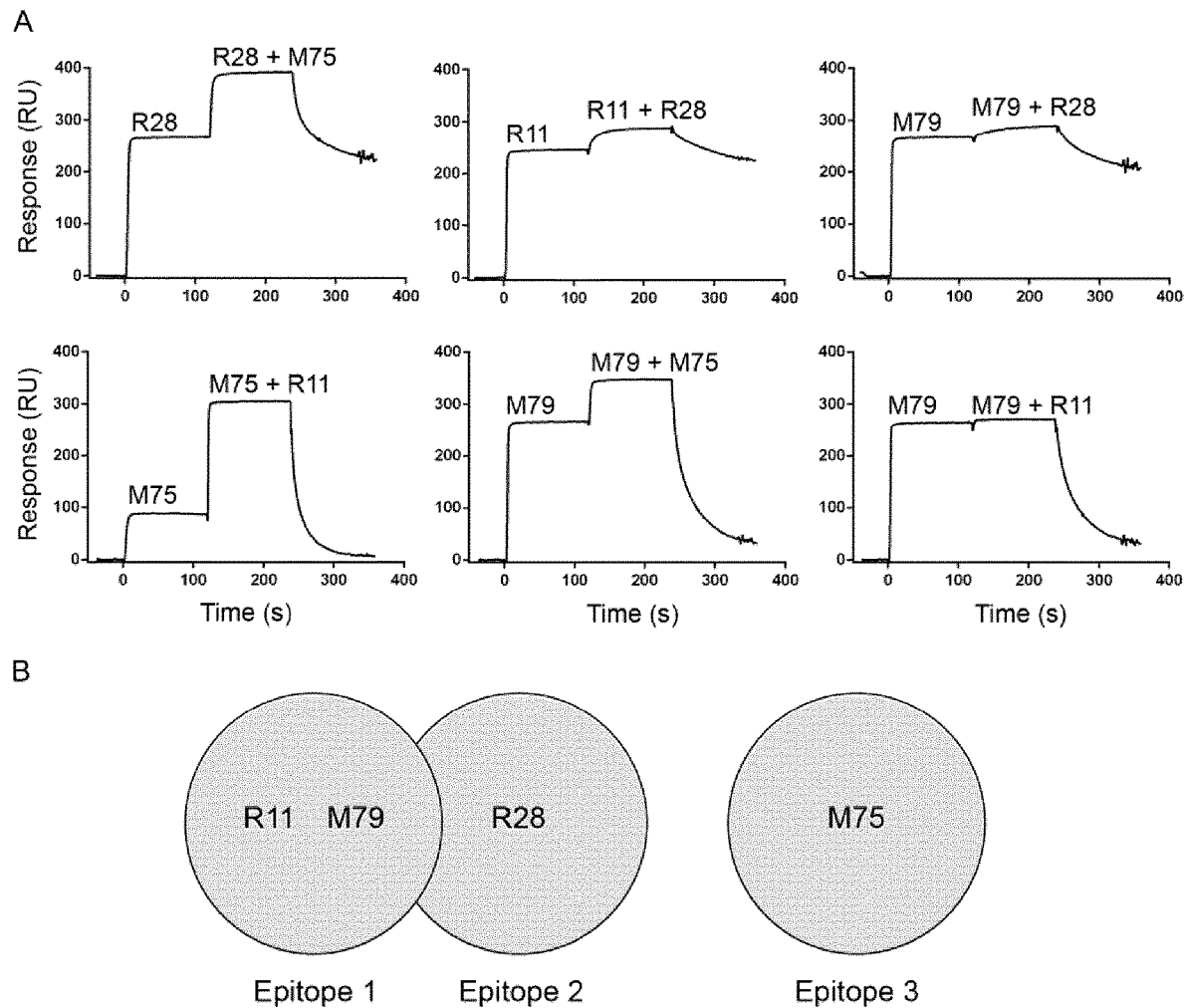
FIG. 5 illustrates SPR-based epitope binning experiments. The SPR-based epitope binning experiments identified the different epitope bins targeted by the pool of serum albumin binding $V_H$Hs. (A) Representative SPR sensorgrams of $V_H$H co-injection experiments of various $V_H$H+$V_H$H combinations. (B) Graphical representation of the three epitopes targeted by the serum albumin $V_H$Hs. R11 and M79 bind the same or a completely overlapping epitope, R28 binds an epitope that is partially overlapping with the R11/M79 epitope and M75 binds an epitope distinct from R11, M79 and R28.

The SPR-based epitope binning experiments identified the different epitope bins targeted by the pool of V$_H$Hs. FIG. 5A shows SPR sensorgrams of V$_H$H co-injection experiments of various V$_H$H+V$_H$H combinations (injected at 10-20×K$_D$ concentrations). FIG. 5B shows a graphical representation of the three epitope bins targeted by the serum albumin V$_H$Hs. R11 and M79 bind the same epitope, R28 binds an epitope that is partially overlapping with the R11/M79 epitope and M75 binds an epitope distinct of R11, M79 and R28.

Example 14

SPR FcRn Competition Binding Assay

Figure 6:
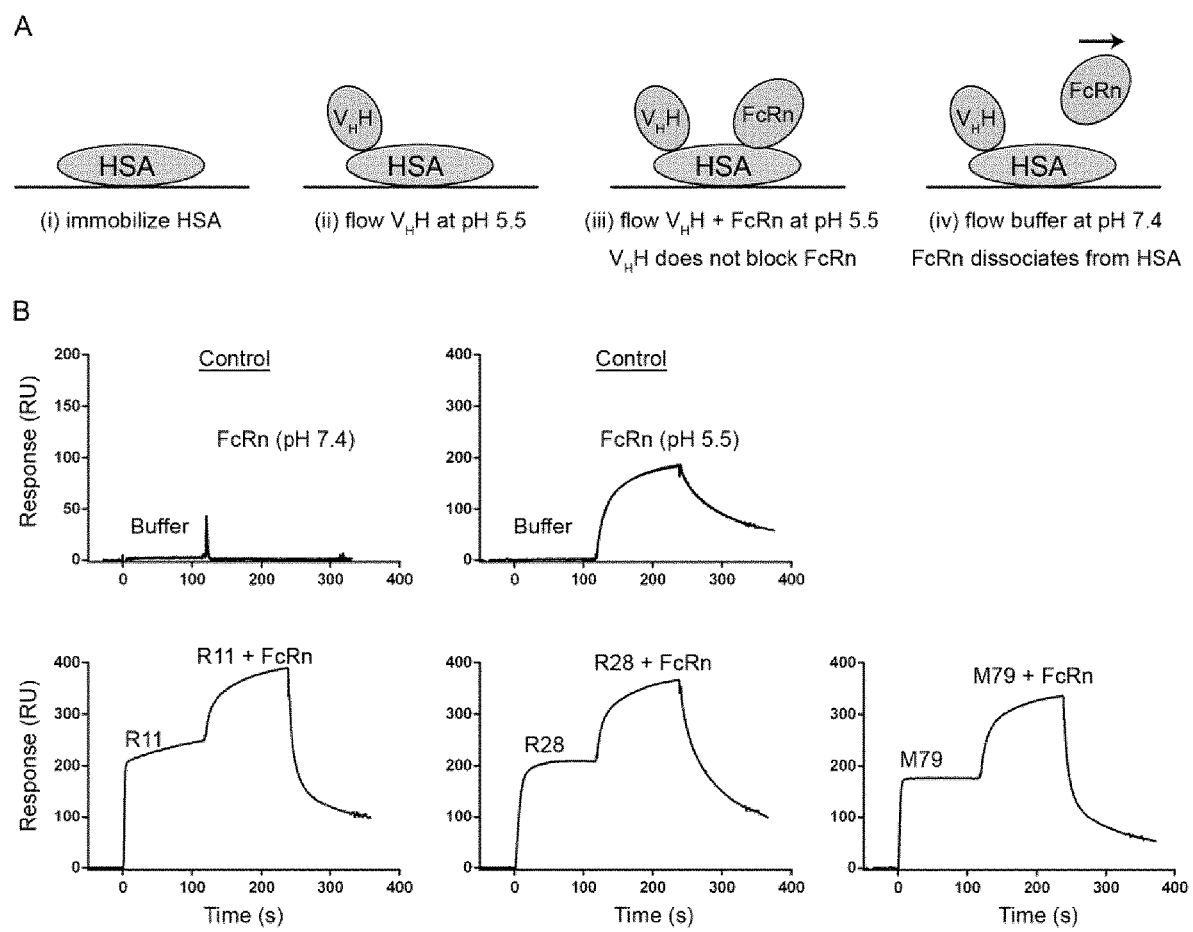
FIG. 6 illustrates SPR-based human FcRn (h-FcRn) binding assays. The assays are used to show that the serum albumin binding $V_H$Hs do not block the interaction of serum albumin with h-FcRn. (A) Graphical representation of the assay design. (B) Top panels showing that h-FcRn does not bind to immobilized HSA at pH 7.4, but does bind at pH 5.5. Lower panels showing R11, R28 and M79 binding to immobilized to HSA at pH 5.5, then injection of h-FcRn illustrates h-FcRn is free to bind HSA, demonstrating the $V_H$Hs do not compete with h-FcRn binding to HSA.

All FcRn binding assays were performed at pH 5.5 using HBSP-MES running buffer. Briefly, human serum albumin was immobilized on a CM5 sensor chip as described above. Human FcRn (h-FcRn, produced recombinantly by NRC) was flowed over immobilized HSA at 2 µM in control experiments to demonstrate binding. To ensure anti-serum albumin V$_H$Hs did not compete with h-FcRn for albumin binding, a co-injection SPR assay was set up as follows. Serum albumin V$_H$Hs were first injected over the HSA surface at concentrations that were 10× their K$_D$ for 120 sat a flow rate of 20 µL/min. Immediately following the first 120 s injection, a second injection followed that contained the V$_H$H and 2 µM h-FcRn. In cases where the V$_H$H did not compete for albumin binding with h-FcRn, sensorgrams show two unique and additive binding responses. The results are shown in FIGS. 6A and 6B.

Anti-Serum Albumin V$_H$H Fusion Proteins

Example 15

Synthesis of Anti-Serum Albumin V$_H$H Fusion Proteins

Figure 7:
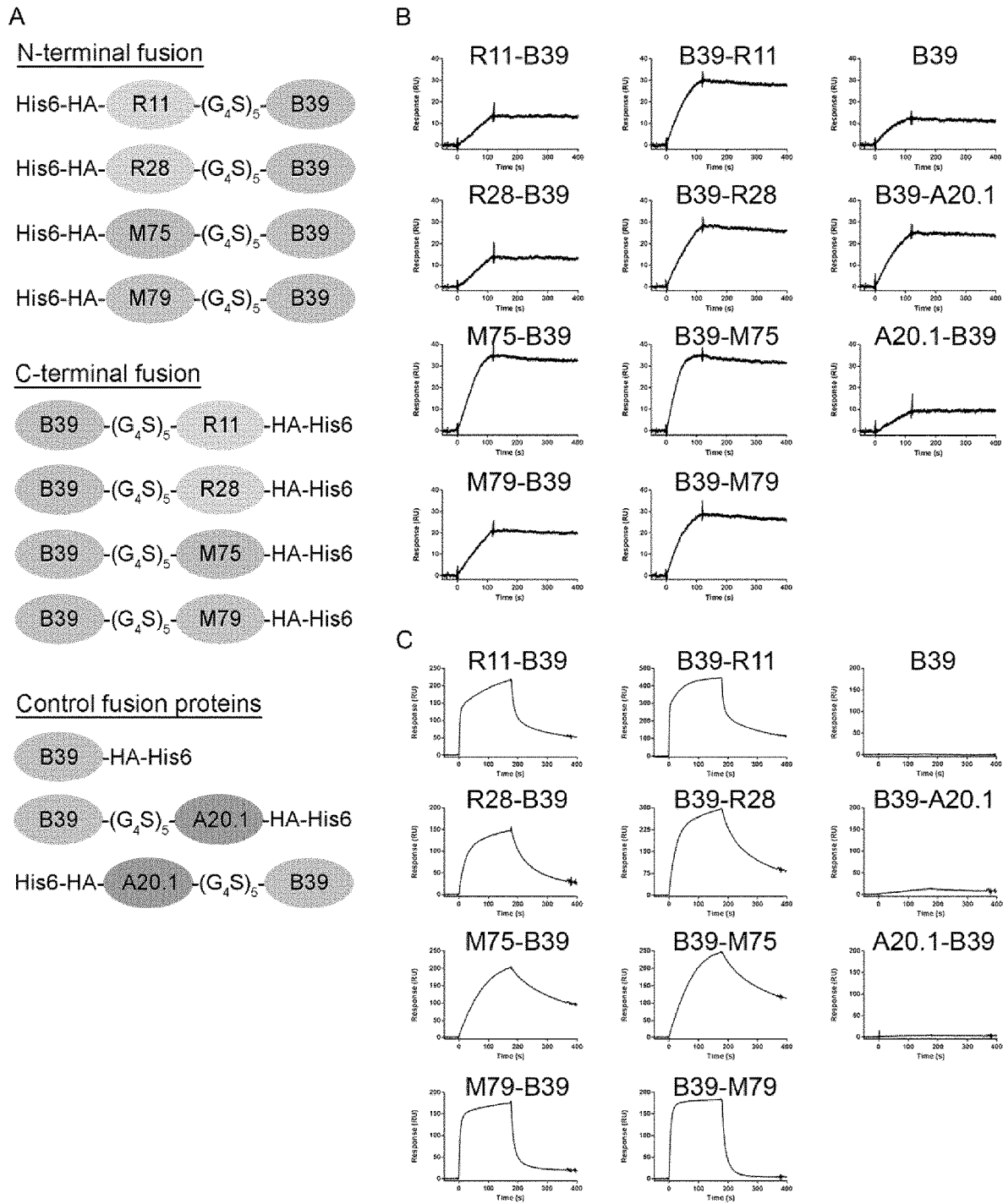
FIG. 7 illustrates that serum albumin $V_H$Hs can be formatted as N-terminal or C-terminal fusions and remain functional. A representative $V_H$H (B39, SEQ ID NO:74; Murase et al, 2014) was used to demonstrate that the serum albumin binding $V_H$Hs can be placed at either the N-terminus or C-terminus of the representative $V_H$H (B39) and retain their ability to bind human serum albumin. (A) Schematic representation of construct designs. (B) SPR assays demonstrating functional binding of constructs to *C. difficile* toxin B (via B39 $V_H$H). (C) SPR assays demonstrating functional binding of constructs to human serum albumin (via R11, R28, M75 or M79 $V_H$Hs).

Anti-serum albumin V$_H$Hs were synthesized as fusion proteins to the C. difficile toxin B V$_H$H (B39; Murase et al, 2014) by Genscript using a (GGGGS)$_5$ linker. A control construct consisting of a C. difficile toxin A V$_H$H (A20; Hussak et al, 2011a) fused to B39 was synthesized as a control, as well as the B39 V$_H$H monomer. Sequences were subcloned into the expression vector PSJF2H with N-terminal HA and 6 His tags. Plasmid DNA (5 µg) were diluted into 50 µl of nuclease-free water to produce DNA stocks (100 ng/µL) stored at −20° C. FIG. 7A illustrates the different constructs prepared.

Example 16

Expression and Purification

Approximately 5 µL of Zymo Research Mix and Go TG1 E. coli competent cells (Cedarlane) were aliquoted into PCR tubes placed on ice. To this, 0.5 µL of DNA plasmid stock was added to cells and incubated on ice for 10 min. The cells were plated onto pre-warmed (at 37° C.) 2YT+ampicillin plates for incubation overnight at 32° C. V$_H$H fusions were expressed using a 5-day M9 minimal media method as previously described (Baral et al, 2013). After induction of protein expression, cell cultures were harvested at 5,000 rpm for 20 min (4° C.), the supernatant was decanted, and the cell contents were extracted from the cell pellet by whole cell lysis. Briefly, each pellet was resuspended in 100 mL of ice-cold lysis buffer (50 mM Tris-HCl buffer, pH 8.0, 25 mM NaCl, 2 mM EDTA, pH 8.0) and frozen at −80° C. for 1 h. Next, pellets were thawed at room temperature with the addition of DTT and PMSF (final of 1 mM and 2 mM, respectively). Freshly prepared lysozyme was added to each culture (150 µg/mL final concentration) and incubated for 30 min. DNAse was added (200 µL of 15 units/µL) for further 30 min incubation. The slurry was then centrifuged at 8,000 rpm for 30 min at 4° C. The resulting supernatant was dialyzed overnight into immobilized metal affinity chromatography (IMAC) buffer A (10 mM HEPES, pH 7.0, 500 mM NaCl) and sterile filtered. Protein was purified by IMAC using 5 mL HiTrap™ Chelating HP columns (GE Healthcare), under the control of an ÄKTA™ Express (GE Healthcare). A step-wise gradient of 500 mM imidazole in the above buffer was used for protein elution. Proteins were stored at 4° C.

Example 17

Size Exclusion Chromatography and SPR

Size exclusion chromatography was performed on all purified $V_HH$-$V_HH$ fusions with a Superdex 75™ column under the control of an ÄKTA™-FPLC (GE Healthcare) to determine their aggregation state and to provide samples for SPR analysis. Briefly, $V_HHs$ were applied at concentrations of 500 μg with a flow rate of 0.5 mL/min in a mobile phase that consisted of HBS-EP running buffer (10 mM HEPES, pH 7.4, 150 mM NaCl, 3 mM EDTA, and 0.005% (v/v) P20 surfactant)(GE Healthcare). Approximately 0.5 mL samples were collected and sent for SPR. A Biacore 3000 instrument was used to assess the functionality of $V_HH$-$V_HH$ fusion proteins, essentially as described above with the exception that a single concentration injection of $V_HH$-$V_HH$ over the human serum albumin and toxin B surfaces was performed. The results are shown in FIGS. 7B and 7C.

Example 18

Endotoxin Removal

To remove endotoxins, affinity purified fusion proteins were concentrated to 5 mL volume for passage through a HiLoad 1660 S75 size exclusion column (GE Healthcare) under control of an ÄKTA™-FPLC. Briefly, the column was cleaned with 0.5 M NaOH followed by 50% isopropanol to remove endotoxins. $V_HH$ fusion protein samples (5 mL) were injected onto the column at 1 mL/min in PBS, pH 7.5, endotoxin-free buffer (Sigma). Collected samples were concentrated on Amicon spin columns (Millipore) to a 1 mL volume and filtered through 0.22 μM filter (Millipore). Samples were then processed on *Proteus* NoEndo™ Mini spin column kits (Generon, Berkshire, UK) as per the manufacturer's instructions. Samples were tested for endotoxin levels prior to rat PK studies.

Example 19

Rat PK Studies

Male Wistar rats (~200 g) were injected (i.v.) with equimolar amounts of $V_HH$ fusion protein (~0.25 mg/mL) for a total dose of ~1 mg/kg equivalent, with endotoxin levels in the range of 0.14-4 EU/mg. Groups of three rats per fusion protein were tested. Serum (50 μL) was collected at nine time points for up to 168 h. Serum samples were frozen at −20° C. until analysis. The results are shown in FIG. 8A-D.

Example 20

ELISA on PK Serum Samples

Figure 8:
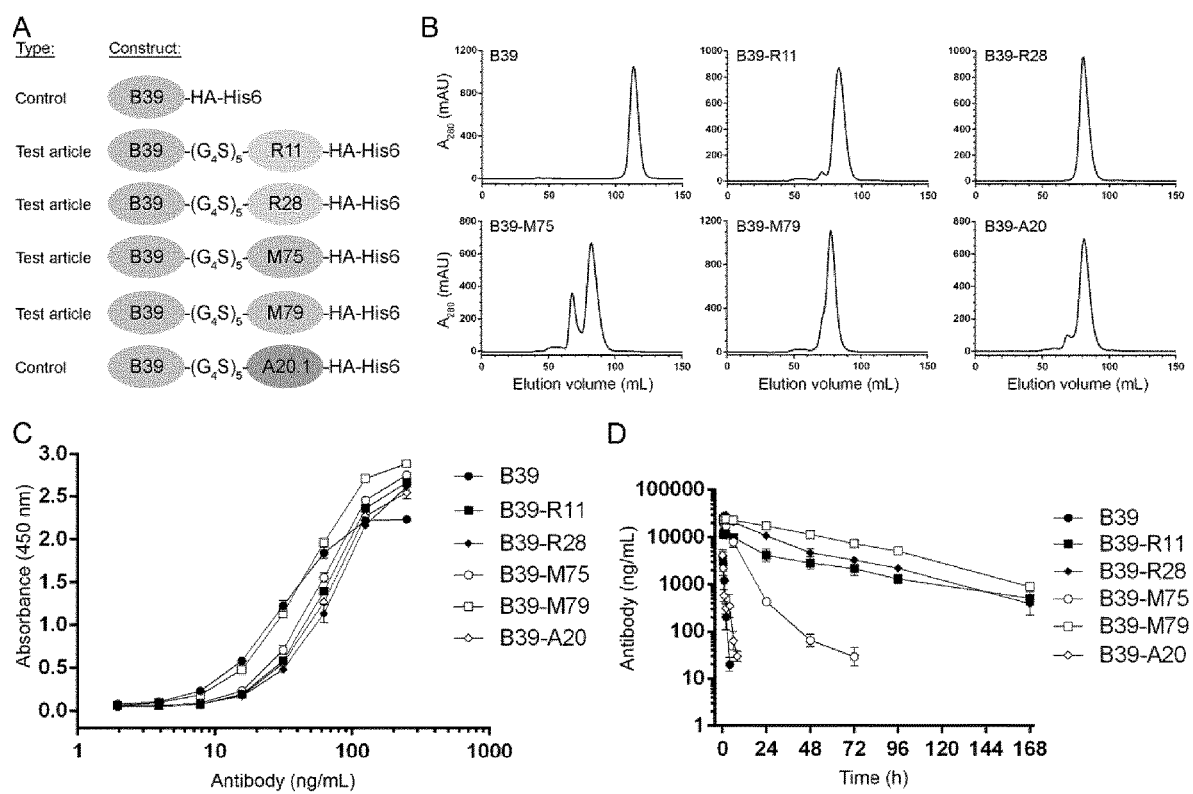
FIG. 8 illustrates the half-life extension of a monovalent single domain antibody in rats. An anti-toxin B $V_H$H B39 is fused to serum albumin binding $V_H$Hs and evaluated in vivo. (A) Design of $V_H$H-$V_H$H dimers that are either control or test articles. B39 is a *C. difficile* toxin B binding antibody. (B) Size exclusion chromatography profiles. (C) ELISA standard curves using toxin B coated on ELISA wells, $V_H$H-$V_H$H constructs added and detected with anti-HA-IgG HRP. (D) Rat in vivo half-life profiles of $V_H$H-$V_H$H fusions injected at 1 mg/kg. The data show that three $V_H$Hs (R11, R28 and M79) significantly extend B39 half-life (31.1-46.1 h) and that the pH sensitive $V_H$H (M75) increases B39 half-life (4.3 h) but to a lesser extent than the aforementioned $V_H$Hs. The half-life of unfused B39 and B39-A20.1 control constructs are ~0.5 h and 1.4 h, respectively.

ELISAs were performed to determine the serum half-life of $V_HH$ fusion proteins in serum, using purified proteins and standard curves. The B39 $V_HH$ antigen, TcdB-RBD (Murase et al, 2014), was coated at 0.3 μg/well in PBS pH 7.4 overnight at 4° C. The next day, wells were blocked in 2% milk in PBS, pH 7.4, for 1 h at 37° C. Next, 100 μL of serum (diluted 1:10, 1:50 or 1:250 in PBS, depending on serum time point) were added to wells in duplicate. Standard curves were also produced on each plate. Serum samples were incubated at room temperature for 1 h. Following three washes with PBS-Tween 20 (0.05%, v/v), a secondary antibody of anti-HA-HRP (1:5000 dilution) in PBS pH 7.4 was added to each well and incubated for 1 h at room temperature. A final set of three washes preceded the addition of the HRP substrate tetramethylbenzidine (Mandel Scientific). The reaction was stopped with 1.5 M phosphoric acid, and the absorbance was measured using a plate reader at 450 nm. The results are shown in FIG. 8C.

Additional Anti-Serum Albumin $V_HH$ Fusion Protein Examples

Example 21

Synthesis of Additional Anti-Serum Albumin $V_HH$ Fusion Constructs

DNA encoding the following nine constructs were synthesized and subcloned as described above. A20-A26, A20-A26-M75, A20-A26-M79, FC5-ABP, FC5-ABP-M75, FC5-ABP-M79, CIBP2, CIBP2-M75, and CIBP2-M79 were all subcloned into the mammalian expression vector pTT5™ (Durocher et al, 2002) with HA and His6 tags. Plasmid DNA (5 μg) were diluted into 50 μL of nuclease-free water to produce DNA stocks (100 ng/μL) stored at −20° C. Iduronate-2-sulfatase (IDS; UniProtKB ref #P22304) enzyme-$V_HH$ conjugates, IDS-R28 and IDS-M79, were designed, expressed and purified by Oxyrane (Gent, Belgium). FIGS. 9A, 10A, 11A and 12A illustrate the different constructs prepared.

Example 22

Transformation and Plasmid Preparation

Approximately 5 μL of Zymo Research Mix and Go TG1 *E. coli* competent cells (Cedarlane) were aliquoted into PCR tubes placed on ice. To this, 0.5 μL of DNA plasmid stock was added to cells and incubated on ice for 10 min. The cells were plated onto pre-warmed (at 37° C.) 2YT+ampicillin plates for incubation overnight at 32° C. Starter cultures of 5 mL of 2YT+ampicillin were inoculated with a single colony and grown at 37° C. for 4 h at which point 1 mL was transferred into 200 mL of 2YT+ampicillin in 500 mL ultra-yield flasks with an air top seal for overnight incubation at 37° C. Plasmid extraction was performed using the endo-free plasmid Maxi prep kit (Thermo-Fisher, Ottawa, ON, Canada). Yields of 300-400 μg of plasmid were obtained for transfection into HEK293-6E cells.

Example 23

Expression and Purification

Mammalian expression was performed essentially as described previously (Durocher et al, 2002). HEK293-6E mammalian cells were cultured from frozen in enriched F17 media at 5% $CO_2$, 60% humidity, 37° C. and 100 rpm shaking. Cultures (100 mL) were transfected with 100 μg DNA/100 μL PEIpro transfection reagent (Polyplus, Illkirch, France) at a cell density of $1.5 \times 10^6$-$1.7 \times 10^6$ cells/mL, 99% cell viability. Cells were fed after 24 h with 2% TNI in enriched F17 media and were then grown for 5 d before harvesting. Harvested cultures were spun at 4000 rpm for 15 min on bench top centrifuge. Supernatants were filtered through a 0.22 μM filter (Millipore), dialyzed into endo-free PBS pH 7.4 (Sigma), then loaded onto an IMAC nickel affinity column (GE Healthcare) on the AKTA system and purified as described earlier. Endotoxins were removed and measured as described above.

Example 24

Rat PK Studies

Rat PK studies were performed exactly as described above (1 mg/kg equivalent) for the other anti-serum albumin $V_HH$ fusion proteins. The results are shown in FIGS. 9E, 10B, 11B, 12D and 13B. One set of rats (FIG. 13B; B39-R11-H6 test group) received 0.5 mg/kg equivalent.

Example 25

ELISA Analysis of A20-A26 PK Serum Samples

ELISA was performed to determine the serum half-life of A20-A26 fusion proteins (with or without fusion to an anti-serum albumin $V_HH$) in serum. The A20-A26 antigen, *C. difficile* toxin A (List Biological Laboratories, Campbell, Calif.) was coated at 0.1 μg/well in PBS, pH 7.4, overnight at 4° C. The next day, wells were blocked in 2% (w/v) milk in PBS, pH 7.5, for 1 h at 37° C. Next, serum samples (diluted 1:100, 1:1,000, 1:5,000 or 1:10,000 in PBS, depending on the fusion protein and time point) were added to wells in duplicate. ELISA plates were incubated at room temperature for 1 h. Following 3 washes with PBS-Tween 20 (0.05%, v/v), secondary antibody of anti-His-HRP (1:5,000 dilution) in PBS, pH 7.4, was added to each well and incubated for 1 h at room temperature. A final set of three washes preceded the addition of the HRP substrate tetramethylbenzidine (Mandel). The reaction was stopped with 1.5 M sulfuric acid, and the absorbance was measured using a plate reader at 450 nm. Serial dilutions of purified proteins were run on the same plates to generate standard curves. The results are shown in FIG. 9B.

Example 26

SPR Analysis

Figure 9:
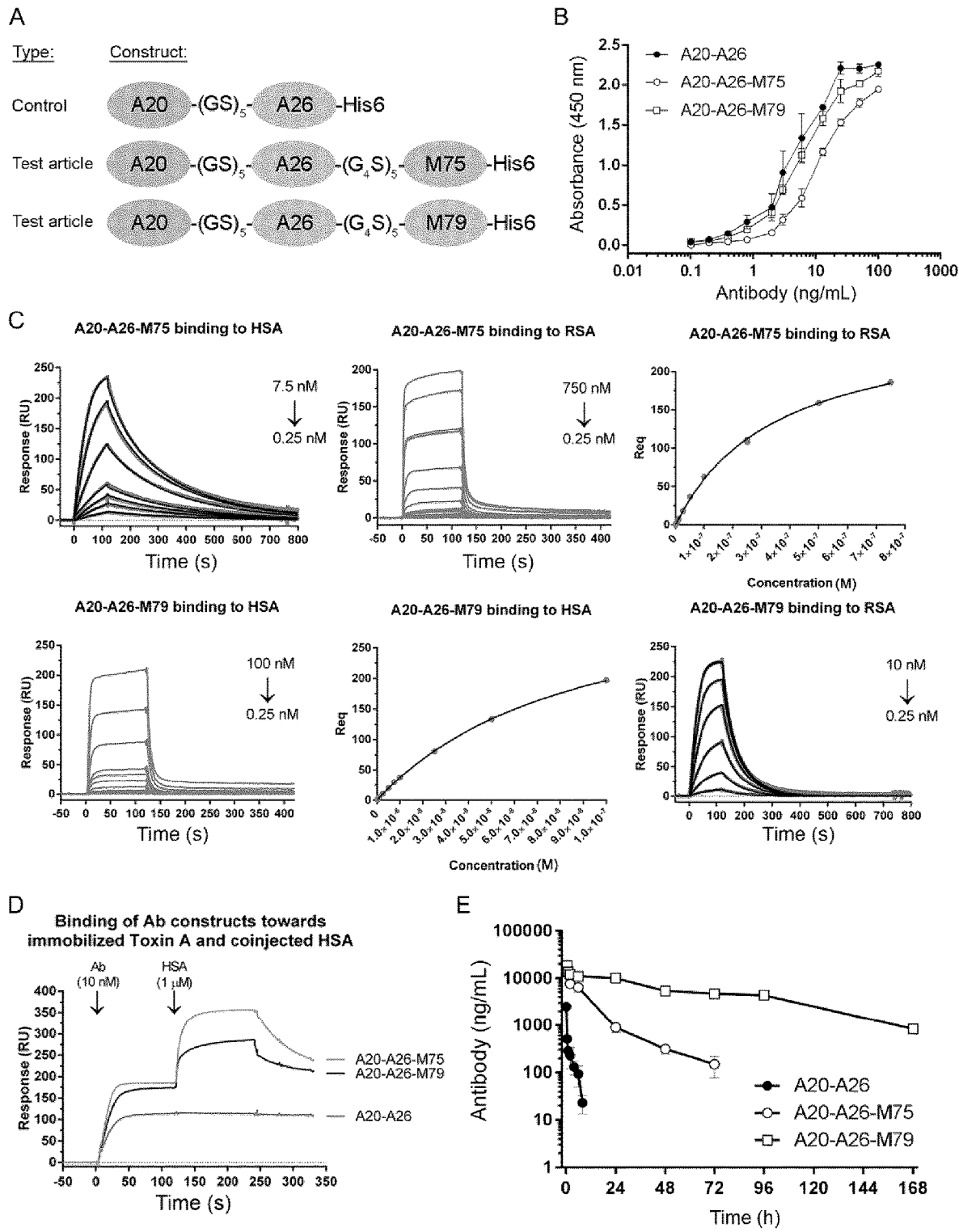
FIG. 9 illustrates the half-life extension of a dimeric single domain antibody in rats. The anti-toxin A $V_H$H-$V_H$H dimer, consisting of anti-*C. difficile* toxin A $V_H$Hs A20 (SEQ ID NO:75) and A26 (SEQ ID NO:76) (Hussack et al 2011a), are fused to serum albumin binding $V_H$Hs and evaluated in vivo. (A) Design of $V_H$H-$V_H$H dimers that are either control or test articles. A20 and A26 bind unique *C. difficile* toxin A epitopes. (B) ELISA standard curves using toxin A coated on ELISA wells, $V_HH$-$V_HH$-$V_HH$ constructs added and detected with anti-His6-IgG HRP. This demonstrates the constructs retain binding to toxin A. (C) SPR assays demonstrating binding of the fusion proteins to human and rat serum albumin surfaces. (D) SPR co-injection assay demonstrating the A20-A26-M75 and A20-A26-M79 fusion proteins can simultaneously bind to toxin A on the SPR surface and to human serum albumin in solution. The control A20-A26 can only bind to toxin A and does not bind human serum albumin in solution, as expected. (E) Rat in vivo half-life profiles of $V_HH$-$V_HH$-$V_HH$ fusions injected at 1 mg/kg. The data show a half-life of 1.8 h for the A20-A26 control construct compared to half-lives of 6.8 h and 45.0 h for A20-A26 fused to M75 and M79, respectively.
Figure 12:
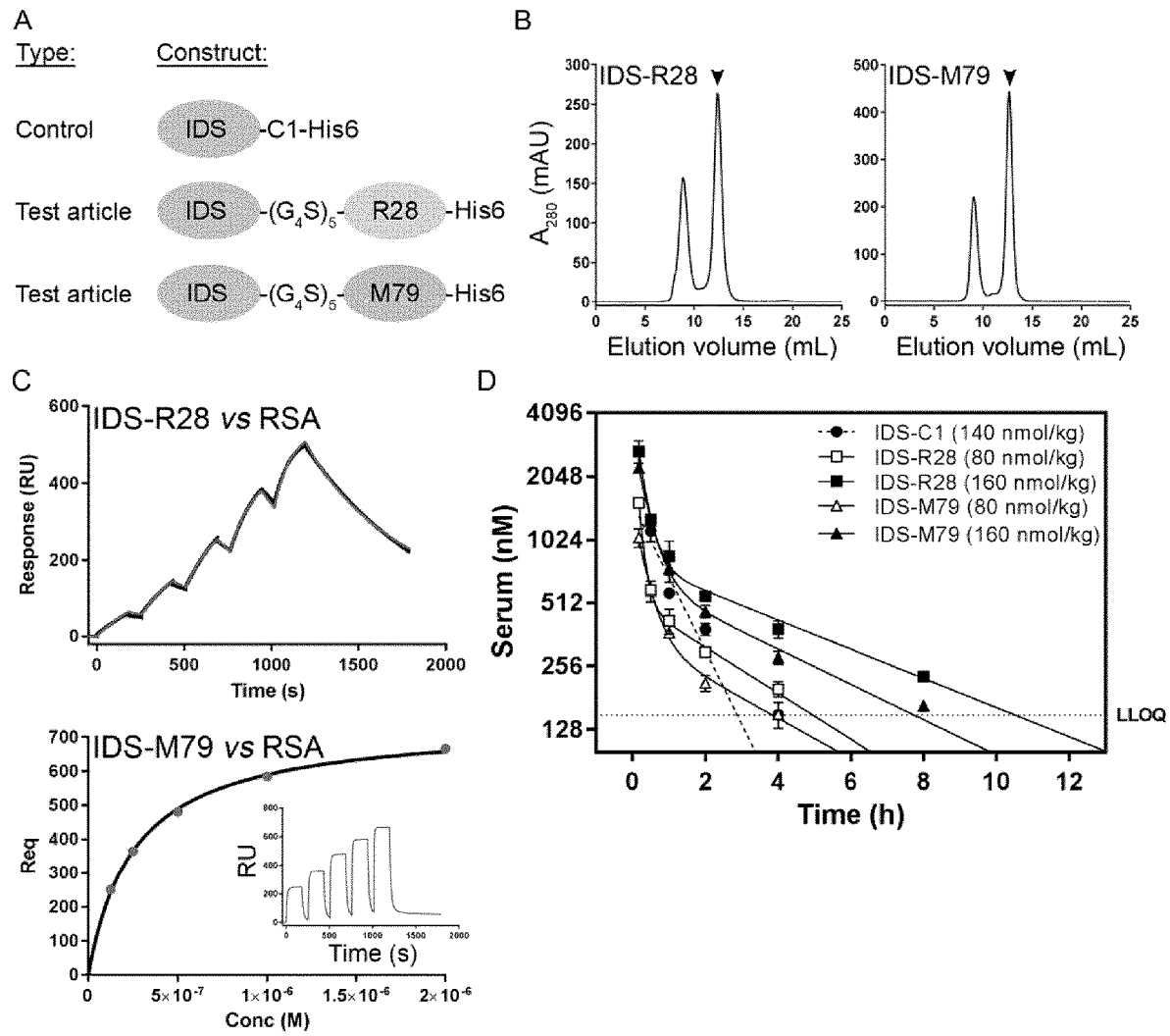
FIG. 12 illustrates the half-life extension of an enzyme. In this example, an enzyme (IDS, SEQ ID NO:80) important in lysosomal storage disease is fused to serum albumin binding $V_H$Hs R28 and M79 and evaluated in vivo. (A) Design of IDS-$V_H$Hs. (B) Size exclusion chromatography profiles. (C) SPR binding profiles of IDS-$V_H$Hs to rat serum albumin with Kos of 55.7 nM and 339 nM for IDS-R28 and IDS-M79, respectively. (D) Rat in vivo half-life profiles of IDS-$V_H$H fusions. The data show a half-life of 0.9 h for the control IDS-C1 enzyme compared to half-lives ranging from 2.8 h to 4.4 h for various IDS-R28 and IDS-M79 constructs tested at different concentrations.

SPR assays were used to demonstrate the binding of the fusion proteins to human and rat serum albumin surfaces (FIG. 9C). A SPR co-injection assay demonstrate that the A20-A26-M75 and A20-A26-M79 fusion proteins can simultaneously bind to toxin A on the surface and to human serum albumin in solution. The control A20-A26 can only bind to toxin A and does not bind human serum albumin in solution, as expected (FIG. 9D). The IDS-R28 and IDS-M79 constructs (FIG. 12A) were SEC purified (FIG. 12B) before confirming that they retain the ability to bind rat serum albumin in SP (FIG. 12C).

Example 27

Figure 10:
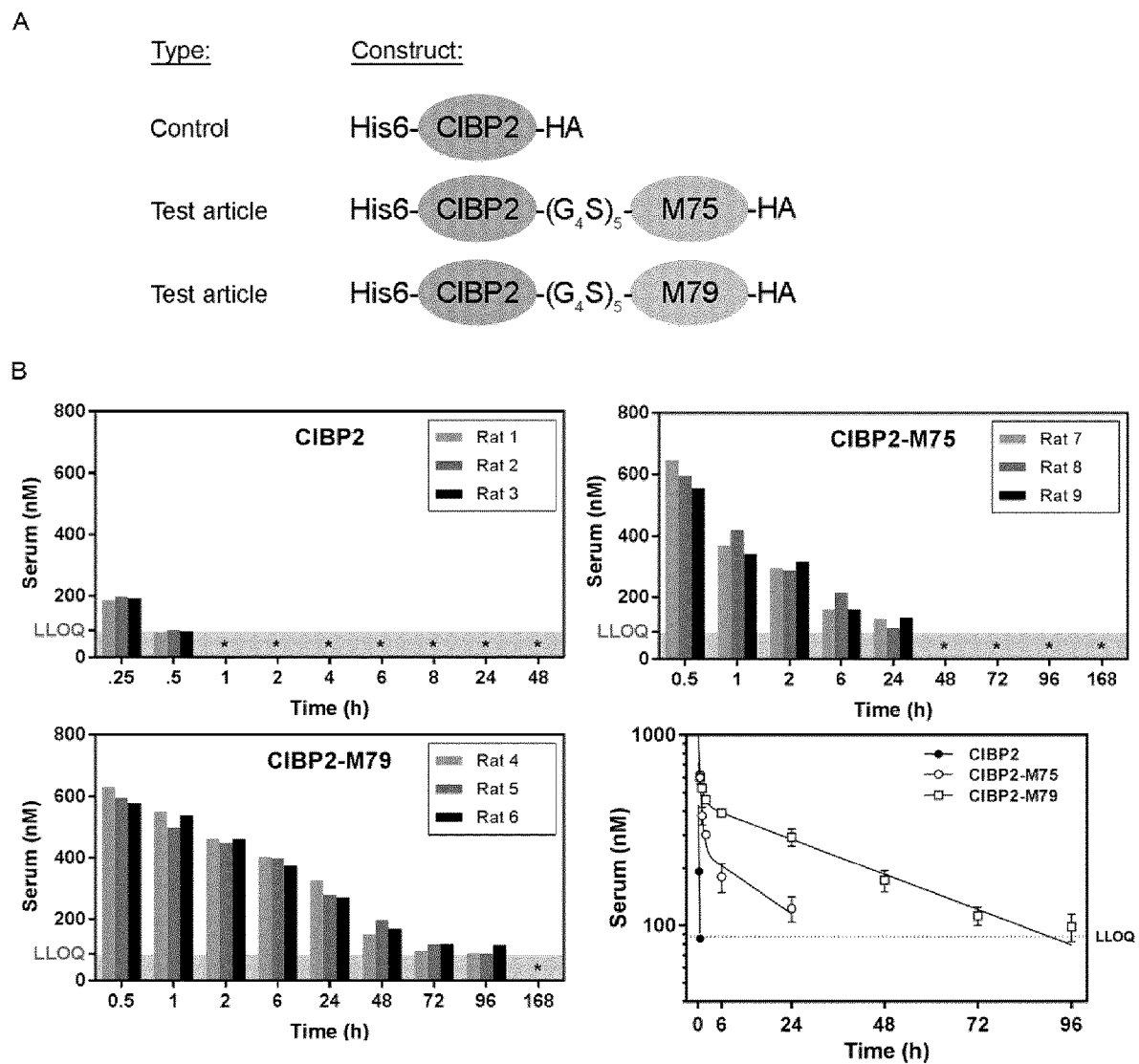
FIG. 10 illustrates the half-life extension of a growth factor binding protein. A growth factor CIBP2 (SEQ ID NO:77)(WO 2008019491 A1; UniProtKB ref #P18065) is fused to serum albumin binding $V_H$Hs and evaluated in vivo. (A) Design of CIBP2-$V_H$Hs that are either control or test articles. (B) Rat in vivo half-life profiles of CIBP2-$V_H$H fusions injected at 1 mg/kg, as determined by MRM mass spectrometry analysis. The data show rapid clearance of the CIBP2 control construct (half-life could not be calculated) compared to half-lives of 4.9 h and 40.3 h for CIBP2 fused to M75 and M79, respectively.
Figure 11:
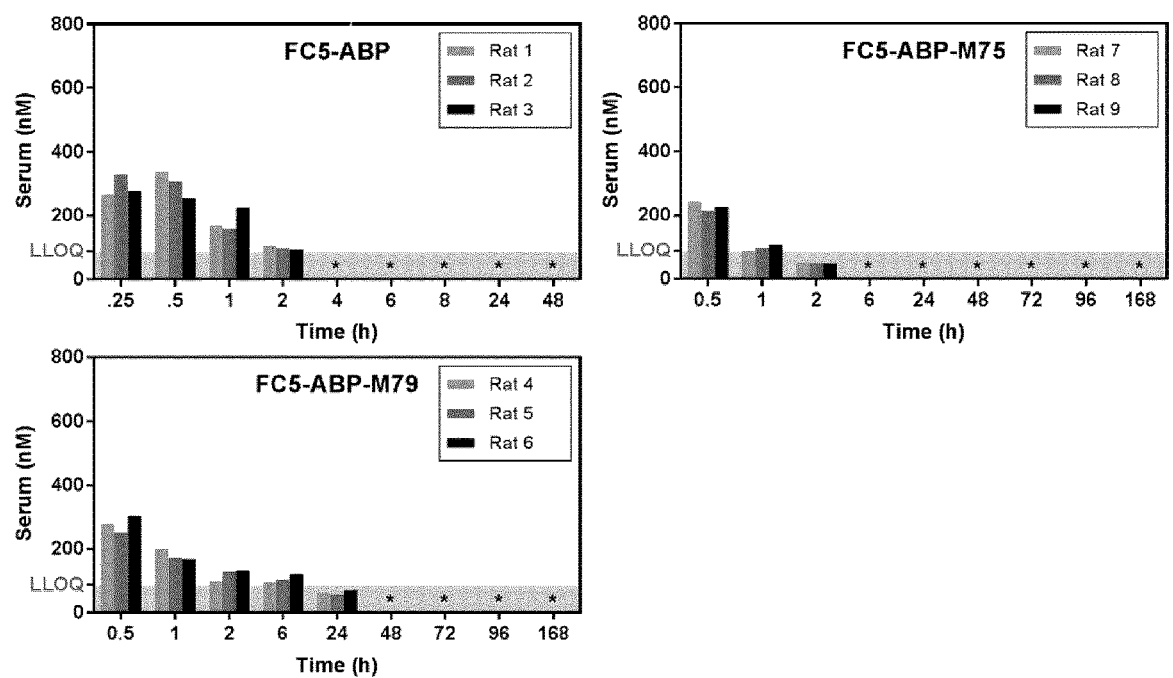
FIG. 11 illustrates half-life extension of a blood brain barrier penetrating antibody FC5 (Muruganandam et al, 2002) fused to an amyloid-β binding peptide (ABP (SEQ ID NO:79); Chakravarthy et al, 2014) construct in rats. FC5-ABP is fused to serum albumin binding $V_H$Hs and evaluated in vivo. (A) Design of FC5-ABP-$V_H$Hs that are either control or test articles. (B) Rat in vivo half-life profiles of FC5-ABP-$V_H$H fusions injected at 1 mg/kg, as determined by MRM mass spectrometry analysis. The data show a half-life of 1.1 h for the FC5-ABP control compared to a half-life of 25.4 h for the FC5-ABP-M79 construct.

MRM Mass Spectrometry Analysis of FC5-ABP, CIBP2 and IDS Fusion Proteins in Rat Serum Using purified protein constructs as controls [CIBP2, CIBP2-M75, CIBP2-M79 (FIG. 10A), FC5-ABP, FC5-ABP-M75, FC5-ABP-M79 (FIG. 11A) and, and IDS, IDS-R28, IDS-M79 (FIG. 12A)], MRM mass spectrometry analysis was used to determine the serum concentrations of the above fusion proteins in rats, essentially as previously described (Haqqani et al, 2013; FIGS. 10B, 11B and 12D).

Example 28

Identification of Lead Humanized $V_HH$s and In Vivo Testing

Figure 13:
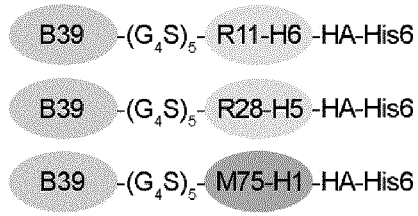
FIG. 13 illustrates the half-life extension of a monovalent single domain antibody in rats using humanized serum albumin binding $V_H$Hs. In this example an anti-toxin B $V_H$H B39 is fused to three representative humanized serum albumin binding $V_H$Hs (M75-H1, SEQ ID NO: 41; R28-H5, SEQ ID NO: 38; R11-H6, SEQ ID NO: 31) and evaluated in vivo. (A) Schematic representation of constructs designed for testing. (B) ELISA standard curves using toxin B coated on ELISA wells, $V_HH$-$V_HH$ constructs added and detected with anti-HA-IgG HRP. (C) Rat in vivo half-life profiles of B39-humanized $V_H$H fusions injected at 1 mg/kg (or 0.5 mg/kg for B39-R11-H6). Serum antibody concentrations were determined by ELISA and obtained from standard curves. The data show a half-life of 3.8 h for B39-M75-H1, 51.2 h for B39-R28-H5 and 41.4 h for B39-R11-H6. The unfused B39 half-life was determined to be 0.5 h (FIG. 8). The data show that all three humanized $V_H$Hs (M75-H1, R28-H5 and R11-H6) extend B39 half-life and that the pH sensitive $V_H$H (M75-H1) increases B39 half-life to a lesser extent. This trend is consistent with the half-life extension of the wild-type versions of these $V_H$Hs. Importantly, $V_H$H humanization did not negatively impact $V_H$H function as in vivo half-life in rats was essentially identical to the durations observed for wild-type $V_H$Hs (Table 2).
Figure 13:
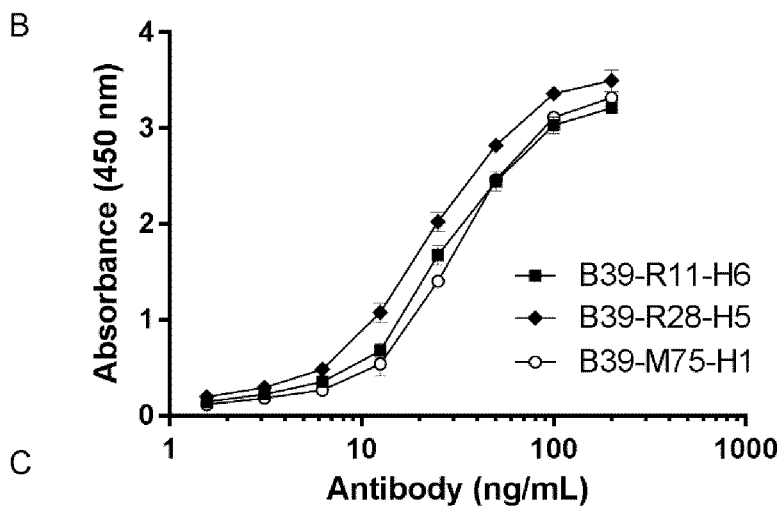
Figure 13:
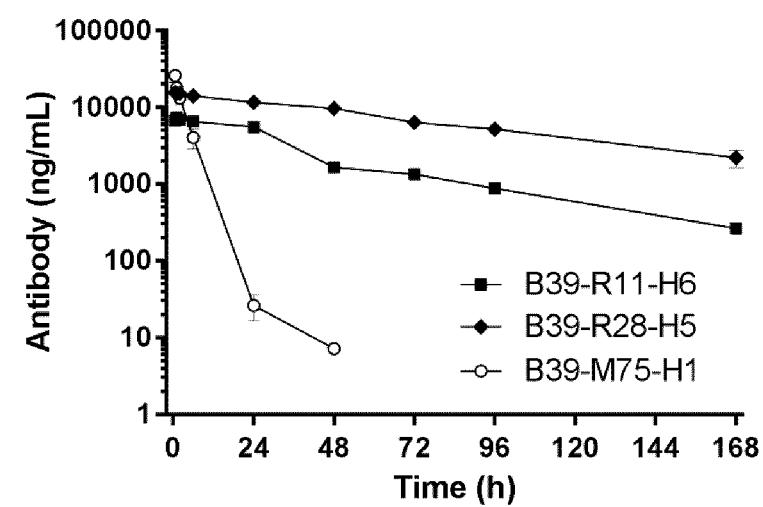

Humanized $V_HH$s were designed (FIG. 2), expressed in *E. coli*, purified by immobilized metal affinity chromatography and assessed by SEC, thermal unfolding ($T_m$) and binding affinity at pH 7.4 and pH 5.5 for albumins from various species. Lead humanized $V_HH$s were fused to B39 $V_HH$ for in vivo half-life extension studies in rats (Table 3, FIG. 13). Based on the biophysical properties described in Table 3 (expression yield, lack of aggregation, preservation of thermal stability and serum albumin binding affinities), the lead humanized version of each $V_HH$ identified are: M75-H1 (SEQ ID NO: 41), M79-H2 (SEQ ID NO: 49), R28-H5 (SEQ ID NO: 38) and R11-H6 (SEQ ID NO: 31). Of these, three examples were fused to the B39 $V_HH$ and the serum half-life evaluated in rats, confirming that humanization of the wild-type $V_HH$ sequences did not negatively impact half-life extension (FIG. 13C).

Example 29

Human Serum Albumin Domain Mapping

Figure 14:
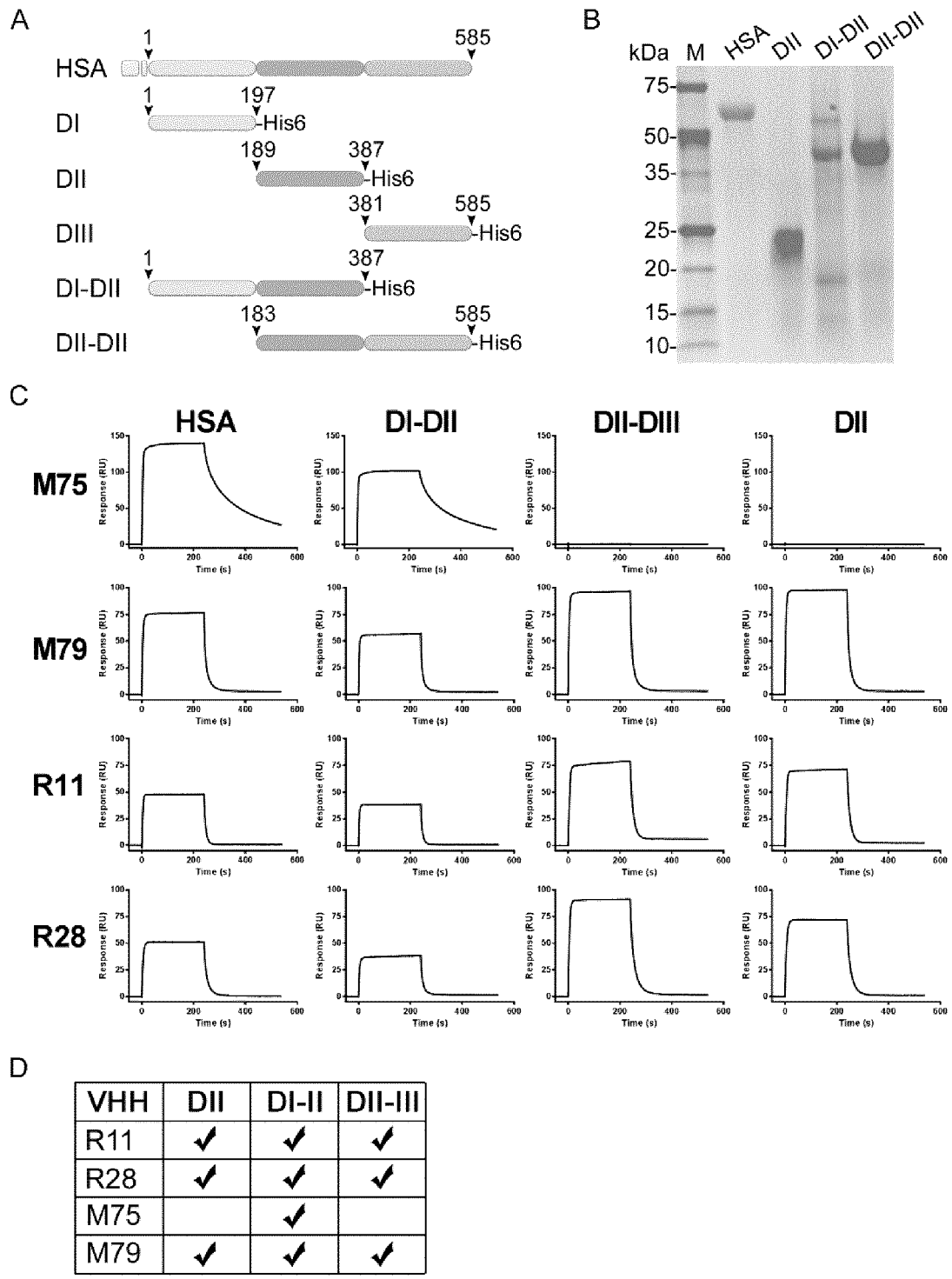
FIG. 14 illustrates crude domain mapping on HSA. Serum albumin is comprised of three major domains (domain 1, DI; domain 2, DII; domain 3, DIII). These domains were expressed and purified from mammalian cells (HEK293 6E) either alone or as fusions (DI, DII, DIII, DI-DII, DII-DIII) to determine the location of $V_H$H binding. (A) Schematic of HSA domains synthesized and cloned into the pTT5 expression vector. Numbers refer to amino acid positions of the mature human serum albumin after signal and pro-peptide cleavage. (B) SDS-PAGE of the constructs expressed and purified. DI and DIII domains could not be expressed. (C) SPR sensorgrams demonstrating the response from injection of 100 nM of each anti-serum albumin $V_H$H (M75, M79, R11 or R28) over amine-coupled surfaces of DII, DI-DII or DII-DIII. (D) Summary of $V_H$H reactivity for various serum albumin domains. From the domain mapping binding studies: M75 binds DI, and M79, R11 and R28 all bind DII of human serum albumin. This is consistent with previous FcRn competition experiments that showed $V_H$Hs did not interfere with FcRn binding to human serum albumin (in DIII). This is also consistent with epitope binning experiments that showed M75 bound an HSA epitope that was distinct from the M79/R11/R28 binding site.

To identify which domain of serum albumin the $V_HH$s described bind, the three major domains of HSA were expressed in mammalian HEK293-6E cells as either individual domains (DI, DII and DIII) or two neighboring domains (DI-DII and DII-DIII). HSA domains were purified by affinity chromatography, subjected to SEC, and used for SPR binding experiments (FIG. 14). The results demonstrated that M75 binds to HSA domain 1 (DI) and R11, R28 and M79 bind to HSA domain 2 (DII). This data is consistent with FcRn competition assays in that none of the $V_HH$s compete with FcRn for albumin binding that occurs in domain 3 of HSA.

Example 30

Figure 15:
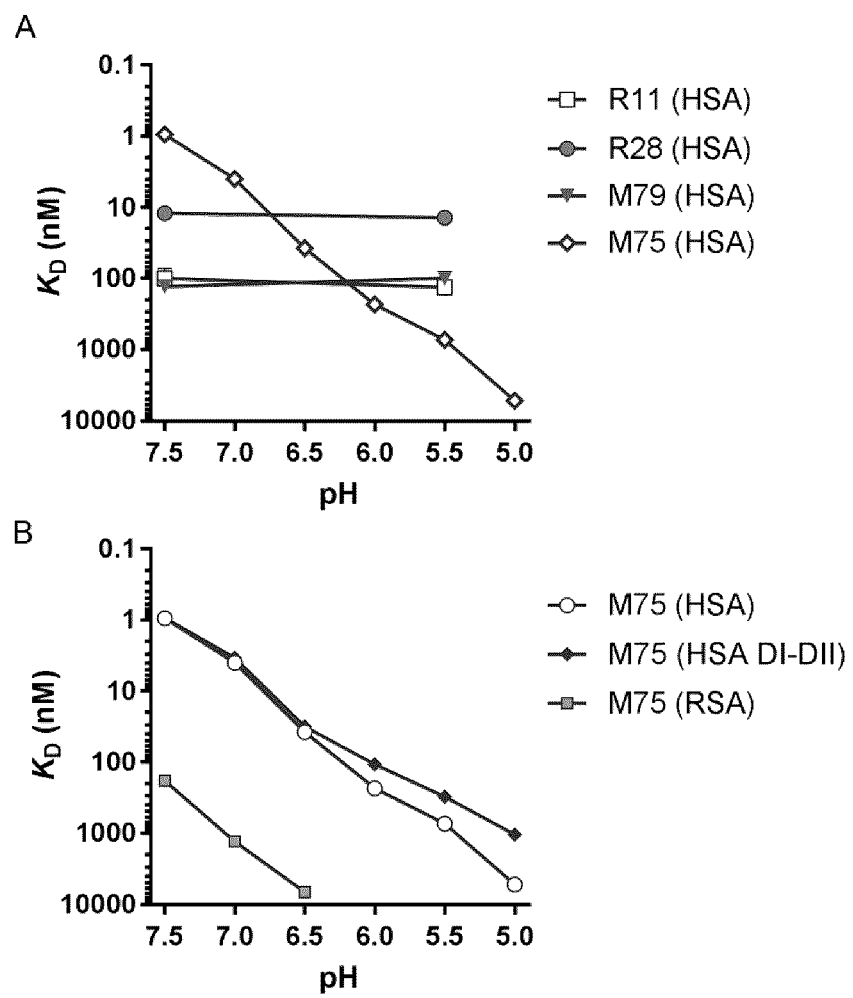
FIG. 15 illustrates the impact of pH on the binding affinity of $V_H$Hs for human and rat serum albumin. (A) Affinity of $V_H$Hs for HSA at various pHs. (B) Affinity of M75 for HSA, HSA DI-DII and RSA at various pHs.

Impact of pH on $V_HH$ Affinities for Serum Albumin $V_HH$ affinities ($K_D$s) for human and rat serum albumin as a function of pH were determined (FIG. 15), to illustrate the unique pH sensitivity of the M75 $V_HH$ for HSA, HSA DI-DII and for RSA. The affinity of M75 for HSA drops significantly, from $K_D$=1.2 nM at pH 7.4 to $K_D$=735 nM at pH 5.5. The affinity of M75 for RSA is $K_D$=315 nM at pH 7.4 while at pH 5.5 the affinity could not be measured because there was no evidence binding. In addition, flowing 50 μM of M75 $V_HH$ over RSA surfaces at pH 6.0 did not show a trace of binding. In comparison, the other three $V_HH$s maintain nearly identical binding affinities for HSA at pHs 7.4 and 5.5.

While preferred embodiments have been described above and illustrated in the accompanying drawings, it will be evident to those skilled in the art that modifications may be made without departing from this disclosure. Such modifications are considered as possible variants comprised in the scope of the disclosure.

| SEQUENCES | | |
|---|---|---|
| SEQ ID NO: | Sequence | Description |
| SEQ ID NO: 1 | GFLLRSNTM | CDR1-R11 |
| SEQ ID NO: 2 | IRPSGLT | CDR2-R11 |
| SEQ ID NO: 3 | HTRPPFQRDS | CDR3.1-R11 |
| SEQ ID NO: 4 | ATRPPFQRDS | CDR3.2-R11 |
| SEQ ID NO: 5 | GRTFIAYAM | CDR1-R28 |
| SEQ ID NO: 6 | ITNFAGGTT | CDR2-R28 |
| SEQ ID NO: 7 | AADRSAQTMRQVRPVLPY | CDR3-R28 |
| SEQ ID NO: 8 | GRTFDNYVM | CDR1-M75 |
| SEQ ID NO: 9 | ISGSGSIT | CDR2-M75 |
| SEQ ID NO: 10 | AAGSRRTYYREPKFYPS | CDR3-M75 |
| SEQ ID NO: 11 | GSTFSSSSV | CDR1-M79 |
| SEQ ID NO: 12 | ITSGGST | CDR2-M79 |
| SEQ ID NO: 13 | NVAGRNWVPISRYSPGPY | CDR3.1-M79 |
| SEQ ID NO: 14 | AVAGRNWVPISRYSPGPY | CDR3.2-M79 |
| SEQ ID NO: 15 | GSIESINRM | CDR1-H18 |
| SEQ ID NO: 16 | ISKGGST | CDR2-H18 |
| SEQ ID NO: 17 | AAGPVWEQF | CDR3-H18 |
| SEQ ID NO: 18 | GRTISLYAV | CDR1-Rh34 |
| SEQ ID NO: 19 | ISWTDSST | CDR2-Rh34 |
| SEQ ID NO: 20 | AADVSIRGLQKYEYDY | CDR3-Rh34 |
| SEQ ID NO: 21 | TRTFSSYIM | CDR1-Rh46 |
| SEQ ID NO: 22 | ISWSGRMT | CDR2-Rh46 |
| SEQ ID NO: 23 | AADRTTAWGAPRSQYDS | CDR3-Rh46 |
| SEQ ID NO: 24 | QVKLEESGGGLVQAGGSLRLSCVGPGFLLRSNTMGWYRQAPGKERELVAFIRPSGLTNYNDAVQGRFTISRDNAKNTVYLQMNALKPEDTAVYYCHTRPPFQRDSWGQGTQVTVSS | R11 sdAb |
| SEQ ID NO: 25 | EVQLVESGGGLVQPGGSLRLSCAASGFLLRSNTMGWVRQAPGKGLEWVSFIRPSGLTNYNDAVQGRFTISRDNSKNTLYLQMNSLRAEDTAVYYCATRPPFQRDSWGQGTLVTVSS | R11-H0 |
| SEQ ID NO: 26 | EVQLVESGGGLVQPGGSLRLSCAASGFLLRSNTMGWYRQAPGKGLELVSFIRPSGLTNYNDAVQGRFTISRDNSKNTLYLQMNSLRAEDTAVYYCATRPPFQRDSWGQGTLVTVSS | R11-H1 |
| SEQ ID NO: 27 | EVQLVESGGGLVQPGGSLRLSCAASGFLLRSNTMGWYRQAPGKGLELVSFIRPSGLTNYNDAVQGRFTISRDNSKNTLYLQMNSLRAEDTAVYYCHTRPPFQRDSWGQGTLVTVSS | R11-H2 |
| SEQ ID NO: 28 | EVQLVESGGGLVQPGGSLRLSCAASGFLLRSNTMGWYRQAPGKERELVSFIRPSGLTNYNDAVQGRFTISRDNSKNTLYLQMNSLRAEDTAVYYCHTRPPFQRDSWGQGTLVTVSS | R11-H3 |
| SEQ ID NO: 29 | QVQLVESGGGLVQPGGSLRLSCAASGFLLRSNTMGWYRQAPGKERELVAFIRPSGLTNYNDAVQGRFTISRDNSKNTLYLQMNSLRAEDTAVYYCHTRPPFQRDSWGQGTLVTVSS | R11-H4 |

-continued

| SEQ ID NO: | Sequence | Description |
|---|---|---|
| SEQ ID NO: 30 | QVQLVESGGGLVQPGGSLRLSCAGPGFLLRSNTMGWY<br>RQAPGKERELVAFIRPSGLTNYNDAVQGRFTISRDNSK<br>NTLYLQMNSLRAEDTAVYYCHTRPPFQRDSWGQGTLV<br>TVSS | R11-H5 |
| SEQ ID NO: 31 | QVQLVESGGGLVQPGGSLRLSCAGPGFLLRSNTMGWY<br>RQAPGKERELVAFIRPSGLTNYNDAVQGRFTISRDNAK<br>NTVYLQMNSLRAEDTAVYYCHTRPPFQRDSWGQGTLV<br>TVSS | R11-H6 |
| SEQ ID NO: 32 | QVQLVESGGGLVQAGGSLRLSCVASGRTFIAYAMGWF<br>RQAPGKEREFVAAITNFAGGTTYYADSVKGRFTISRDNA<br>KTTVYLQMNSLKPEDTALYYCAADRSAQTMRQVRPVLP<br>YWGQGTQVTVSS | R28 sdAb |
| SEQ ID NO: 33 | EVQLVESGGGLVQPGGSLRLSCAASGRTFIAYAMGWV<br>RQAPGKGLEWVSAITNFAGGTTYYADSVKGRFTISRDN<br>SKNTLYLQMNSLRAEDTAVYYCAADRSAQTMRQVRPV<br>LPYWGQGTLVTVSS | R28-H0 |
| SEQ ID NO: 34 | EVQLVESGGGLVQPGGSLRLSCAASGRTFIAYAMGWF<br>RQAPGKGLEFVSAITNFAGGTTYYADSVKGRFTISRDNS<br>KNTLYLQMNSLRAEDTAVYYCAADRSAQTMRQVRPVL<br>PYWGQGTLVTVSS | R28-H1 |
| SEQ ID NO: 35 | EVQLVESGGGLVQPGGSLRLSCAASGRTFIAYAMGWF<br>RQAPGKEREFVSAITNFAGGTTYYADSVKGRFTISRDNS<br>KNTLYLQMNSLRAEDTAVYYCAADRSAQTMRQVRPVL<br>PYWGQGTLVTVSS | R28-H2 |
| SEQ ID NO: 36 | QVQLVESGGGLVQPGGSLRLSCAASGRTFIAYAMGWF<br>RQAPGKEREFVAAITNFAGGTTYYADSVKGRFTISRDNS<br>KNTLYLQMNSLRAEDTAVYYCAADRSAQTMRQVRPVL<br>PYWGQGTLVTVSS | R28-H3 |
| SEQ ID NO: 37 | QVQLVESGGGLVQPGGSLRLSCAASGRTFIAYAMGWF<br>RQAPGKEREFVAAITNFAGGTTYYADSVKGRFTISRDNA<br>KTTVYLQMNSLRAEDTAVYYCAADRSAQTMRQVRPVLP<br>YWGQGTLVTVSS | R28-H4 |
| SEQ ID NO: 38 | QVQLVESGGGLVQPGGSLRLSCAASGRTFIAYAMGWF<br>RQAPGKEREFVAAITNFAGGTTYYADSVKGRFTISRDNA<br>KTTVYLQMNSLRAEDTAVYYCAADRSAQTMRQVRPVL<br>PYWGQGTLVTVSS | R28-H5 |
| SEQ ID NO: 39 | QVQLVESGGGFVQAGGSLRLSCAASGRTFDNYVMAWF<br>RQAPGKEREFVASISGSGSITNYANSVKDRFTISRDSAK<br>NAIYLQMNSLKPEDTALYYCAAGSRRTYYREPKFYPSW<br>GQGTQVTVSS | M75 sdAb |
| SEQ ID NO: 40 | EVQLVESGGGLVQPGGSLRLSCAASGRTFDNYVMAWV<br>RQAPGKGLEWVSSISGSGSITNYANSVKDRFTISRDNSK<br>NTLYLQMNSLRAEDTAVYYCAAGSRRTYYREPKFYPS<br>WGQGTLVTVSS | M75-H0 |
| SEQ ID NO: 41 | EVQLVESGGGLVQPGGSLRLSCAASGRTFDNYVMAWF<br>RQAPGKGLEFVSSISGSGSITNYANSVKDRFTISRDNSK<br>NTLYLQMNSLRAEDTAVYYCAAGSRRTYYREPKFYPS<br>WGQGTLVTVSS | M75-H1 |
| SEQ ID NO: 42 | EVQLVESGGGLVQPGGSLRLSCAASGRTFDNYVMAWF<br>RQAPGKEREFVSSISGSGSITNYANSVKDRFTISRDNSK<br>NTLYLQMNSLRAEDTAVYYCAAGSRRTYYREPKFYPS<br>WGQGTLVTVSS | M75-H2 |
| SEQ ID NO: 43 | QVQLVESGGGLVQPGGSLRLSCAASGRTFDNYVMAWF<br>RQAPGKEREFVASISGSGSITNYANSVKDRFTISRDNSK<br>NTLYLQMNSLRAEDTAVYYCAAGSRRTYYREPKFYPS<br>WGQGTLVTVSS | M75-H3 |
| SEQ ID NO: 44 | QVQLVESGGGLVQPGGSLRLSCAASGRTFDNYVMAWF<br>RQAPGKEREFVASISGSGSITNYANSVKDRFTISRDSSK<br>NALYLQMNSLRAEDTAVYYCAAGSRRTYYREPKFYPS<br>WGQGTLVTVSS | M75-H4 |

| SEQ ID NO: | Sequence | Description |
|---|---|---|
| SEQ ID NO: 45 | QVQLVESGGGLVQPGGSLRLSCAASGRTFDNYVMAWF RQAPGKEREFVASISGSGSITNYANSVKDRFTISRDSAK NAIYLQMNSLRAEDTAVYYCAAGSRRTYYREPKFYPSW GQGTLVTVSS | M75-H5 |
| SEQ ID NO: 46 | QVKLEESGGGLVQAGGSLKLSCAASGSTFSSSSVGWY RQAPGQQRELVAAITSGGSTNTADSVKGRFTMSRDNA KNTVYLQMRDLKPEDTAVYYCNVAGRNWVPISRYSPG PYWGQGTQVTVSS | M79 sdAb |
| SEQ ID NO: 47 | EVQLVESGGGLVQPGGSLRLSCAASGSTFSSSSVGWV RQAPGKGLEWVSAITSGGSTNTADSVKGRFTISRDNSK NTLYLQMNSLRAEDTAVYYCAVAGRNWVPISRYSPGPY WGQGTLVTVSS | M79-H0 |
| SEQ ID NO: 48 | EVQLVESGGGLVQPGGSLRLSCAASGSTFSSSSVGWY RQAPGKGLELVSAITSGGSTNTADSVKGRFTISRDNSKN TLYLQMNSLRAEDTAVYYCAVAGRNWVPISRYSPGPY WGQGTLVTVSS | M79-H1 |
| SEQ ID NO: 49 | EVQLVESGGGLVQPGGSLRLSCAASGSTFSSSSVGWY RQAPGKGLELVSAITSGGSTNTADSVKGRFTISRDNSKN TLYLQMNSLRAEDTAVYYCNVAGRNWVPISRYSPGPY WGQGTLVTVSS | M79-H2 |
| SEQ ID NO: 50 | EVQLVESGGGLVQPGGSLRLSCAASGSTFSSSSVGWY RQAPGKQRELVSAITSGGSTNTADSVKGRFTISRDNSK NTLYLQMNSLRAEDTAVYYCNVAGRNWVPISRYSPGPY WGQGTLVTVSS | M79-H3 |
| SEQ ID NO: 51 | QVQLVESGGGLVQPGGSLRLSCAASGSTFSSSSVGWY RQAPGQQRELVAAITSGGSTNTADSVKGRFTISRDNSK NTLYLQMNSLRAEDTAVYYCNVAGRNWVPISRYSPGPY WGQGTLVTVSS | M79-H4 |
| SEQ ID NO: 52 | QVQLVESGGGLVQPGGSLRLSCAASGSTFSSSSVGWY RQAPGQQRELVAAITSGGSTNTADSVKGRFTISRDNAK NTVYLQMNSLRAEDTAVYYCNVAGRNWVPISRYSPGP YWGQGTLVTVSS | M79-H5 |
| SEQ ID NO: 53 | QVQLVESGGGLVQAGGSLRLSCTASGSIESINRMAWYR QAPGQQREFVARISKGGSTNYPDSVKGRFTISRDNAKN TVYLQMNSLKPEDTAVYYCAAGPVWEQFWGQGTQVTV SS | H18 sdAb |
| SEQ ID NO: 54 | EVQLVESGGGLVQPGGSLRLSCAASGSIESINRMAWVR QAPGKGLEWVSRISKGGSTNYPDSVKGRFTISRDNSKN TLYLQMNSLRAEDTAVYYCAAGPVWEQFWGQGTLVTV SS | H18-H0 |
| SEQ ID NO: 55 | EVQLVESGGGLVQPGGSLRLSCAASGSIESINRMAWYR QAPGKGLEFVSRISKGGSTNYPDSVKGRFTISRDNSKN TLYLQMNSLRAEDTAVYYCAAGPVWEQFWGQGTLVTV SS | H18-H1 |
| SEQ ID NO: 56 | EVQLVESGGGLVQPGGSLRLSCAASGSIESINRMAWYR QAPGKQREFVSRISKGGSTNYPDSVKGRFTISRDNSKN TLYLQMNSLRAEDTAVYYCAAGPVWEQFWGQGTLVTV SS | H18-H2 |
| SEQ ID NO: 57 | QVQLVESGGGLVQPGGSLRLSCAASGSIESINRMAWYR QAPGKQREFVARISKGGSTNYPDSVKGRFTISRDNSKN TLYLQMNSLRAEDTAVYYCAAGPVWEQFWGQGTLVTV SS | H18-H3 |
| SEQ ID NO: 58 | QVQLVESGGGLVQPGGSLRLSCAASGSIESINRMAWYR QAPGQQREFVARISKGGSTNYPDSVKGRFTISRDNSKN TLYLQMNSLRAEDTAVYYCAAGPVWEQFWGQGTLVTV SS | H18-H4 |
| SEQ ID NO: 59 | QVQLVESGGGLVQPGGSLRLSCAASGSIESINRMAWYR QAPGQQREFVARISKGGSTNYPDSVKGRFTISRDNAKN TVYLQMNSLRAEDTAVYYCAAGPVWEQFWGQGTLVTV SS | H18-H5 |

| SEQ ID NO: | Sequence | Description |
|---|---|---|
| SEQ ID NO: 60 | QVKLEESGGGLVQAGGSLRLSCAASGRTISLYAVGWFR<br>RAPGKEREFVAAISWTDSSTYYADSVKGRFTISRDNAK<br>NTVYLGMNSLNPEDTAVYYCAADVSIRGLQKYEYDYWG<br>QGTQVTVSS | Rh34 sdAb |
| SEQ ID NO: 61 | EVQLVESGGGLVQPGGSLRLSCAASGRTISLYAVGWVR<br>QAPGKGLEWVSAISWTDSSTYYADSVKGRFTISRDNSK<br>NTLYLQMNSLRAEDTAVYYCAADVSIRGLQKYEYDYWG<br>QGTLVTVSS | Rh34-H0 |
| SEQ ID NO: 62 | EVQLVESGGGLVQPGGSLRLSCAASGRTISLYAVGWFR<br>QAPGKGLEFVSAISWTDSSTYYADSVKGRFTISRDNSK<br>NTLYLQMNSLRAEDTAVYYCAADVSIRGLQKYEYDYWG<br>QGTLVTVSS | Rh34-H1 |
| SEQ ID NO: 63 | EVQLVESGGGLVQPGGSLRLSCAASGRTISLYAVGWFR<br>QAPGKEREFVSAISWTDSSTYYADSVKGRFTISRDNSK<br>NTLYLQMNSLRAEDTAVYYCAADVSIRGLQKYEYDYWG<br>QGTLVTVS | Rh34-H2 |
| SEQ ID NO: 64 | QVQLVESGGGLVQPGGSLRLSCAASGRTISLYAVGWF<br>RQAPGKEREFVAAISWTDSSTYYADSVKGRFTISRDNS<br>KNTLYLQMNSLRAEDTAVYYCAADVSIRGLQKYEYDYW<br>GQGTLVTVSS | Rh34-H3 |
| SEQ ID NO: 65 | QVQLVESGGGLVQPGGSLRLSCAASGRTISLYAVGWF<br>RRAPGKEREFVAAISWTDSSTYYADSVKGRFTISRDNS<br>KNTLYLQMNSLRAEDTAVYYCAADVSIRGLQKYEYDYW<br>GQGTLVTVSS | Rh34-H4 |
| SEQ ID NO: 66 | QVQLVESGGGLVQPGGSLRLSCAASGRTISLYAVGWF<br>RRAPGKEREFVAAISWTDSSTYYADSVKGRFTISRDNA<br>KNTVYLQMNSLRAEDTAVYYCAADVSIRGLQKYEYDYW<br>GQGTLVTVS | Rh34-H5 |
| SEQ ID NO: 67 | QVKLEESGGGLVQAGGSLRLSCTASTRTFSSYIMGWFR<br>QAPGKERELVAAISWSGRMTHYADSVKGRFAISRDNAK<br>NTVYLQMNVLKPEDTAIYSCAADRTTAWGAPRSQYDS<br>WGQGTQVTVSS | Rh46 sdAb |
| SEQ ID NO: 68 | EVQLVESGGGLVQPGGSLRLSCAASTRTFSSYIMGWV<br>RQAPGKGLEWVSAISWSGRMTHYADSVKGRFTISRDN<br>SKNTLYLQMNSLRAEDTAVYYCAADRTTAWGAPRSQY<br>DSWGQGTLVTVSS | Rh46-H0 |
| SEQ ID NO: 69 | EVQLVESGGGLVQPGGSLRLSCAASTRTFSSYIMGWFR<br>QAPGKGLELVSAISWSGRMTHYADSVKGRFTISRDNSK<br>NTLYLQMNSLRAEDTAVYYCAADRTTAWGAPRSQYDS<br>WGQGTLVTVSS | Rh46-H1 |
| SEQ ID NO: 70 | EVQLVESGGGLVQPGGSLRLSCAASTRTFSSYIMGWFR<br>QAPGKERELVSAISWSGRMTHYADSVKGRFTISRDNSK<br>NTLYLQMNSLRAEDTAVYYCAADRTTAWGAPRSQYDS<br>WGQGTLVTVS | Rh46-H2 |
| SEQ ID NO: 71 | QVQLVESGGGLVQPGGSLRLSCAASTRTFSSYIMGWF<br>RQAPGKERELVAAISWSGRMTHYADSVKGRFTISRDNS<br>KNTLYLQMNSLRAEDTAVYYCAADRTTAWGAPRSQYD<br>SWGQGTLVTVSS | Rh46-H3 |
| SEQ ID NO: 72 | QVQLVESGGGLVQPGGSLRLSCAASTRTFSSYIMGWF<br>RQAPGKERELVAAISWSGRMTHYADSVKGRFTISRDNS<br>KNTLYLQMNSLRAEDTAIYSCAADRTTAWGAPRSQYDS<br>WGQGTLVTVSS | Rh46-H4 |
| SEQ ID NO: 73 | QVQLVESGGGLVQPGGSLRLSCAASTRTFSSYIMGWF<br>RQAPGKERELVAAISWSGRMTHYADSVKGRFTISRDNA<br>KNTVYLQMNSLRAEDTAIYSCAADRTTAWGAPRSQYDS<br>WGQGTLVTVSS | Rh46-H5 |
| SEQ ID NO: 74 | QVQLVESGGGLVQAGGSLRLSCAASGLTFSRYVMGWF<br>RQAPGKEREFVAAITWGGTPNYADSVKGRFTISRDNSK<br>NTQYLQMNSLKPEDTAVYYCAAGLGWDSRYSQSYNY<br>WGQGTQVTVSS | B39 |

SEQUENCES

| SEQ ID NO: | Sequence | Description |
|---|---|---|
| SEQ ID NO: 75 | QVQLVESGGGLAQAGGSLRLSCAASGRTFSMDPMAW FRQPPGKEREFVAAGSSTGRTTYYADSVKGRFTISRDN AKNTVYLQMNSLKPEDTAVYYCAAAPYGANWYRDEYA YWGQGTQVTVSS | A20 |
| SEQ ID NO: 76 | QVKLEESGGGLVQAGGSLRLSCAASERTFSRYPVAWF RQAPGAEREFVAVISSTGTSTYYADSVKGRFTISRDNAK VTVYLQMNNLKREDTAVYFCAVNSQRTRLQDPNEYDY WGQGTQVTVSS | A26 |
| SEQ ID NO: 77 | KGGKHHLGLEEPKKLRPPPARTPCQQELDQVLERISTM RLPDERGPLEHLYSLHIPNCDKHGLYNLKQCKMSLNGQ RGECWCVNPNTGKLIQGAPTIRGDPECHLFYNEQQEAR GVHTQRMQ | CIBP2 |
| SEQ ID NO: 78 | EVQLQASGGGLVQAGGSLRLSCAASGFKITHYTMGWF RQAPGKEREFVSRITWGGDNTFYSNSVKGRFTISRDNA KNTVYLQMNSLKPEDTADYYCAAGSTSTATPLRVDYW GKGTQVTVSS | FC5 |
| SEQ ID NO: 79 | KTFKTRKASAQASLASKDKTPKSKSKKRNSTQLKSRVK NI | ABP |
| SEQ ID NO: 80 | SETQANSTTDALNVLLIIVDDLRPSLGCYGDKLVRSPNID QLASHSLLFQNAFAQQAVCAPSRVSFLTGRRPDTTRLY DFNSYWRVHAGNFSTIPQYFKENGYVTMSVGKVFHPGI SSNHTDDSPYSWSFPPYHPSSEKYENTKTCRGPDGEL HANLLCPVDVLDVPEGTLPDKQSTEQAIQLLEKMKTSAS PFFLAVGYHKPHIPFRYPKEFQKLYPLENITLAPDPEVPD GLPPVAYNPWMDIRQREDVQALNISVPYGPIPVDFQRKI RQSYFASVSYLDTQVGRLLSALDDLQLANSTIIAFTSDH GWALGEHGEWAKYSNFDVATHVPLIFYVPGRTASLPEA GEKLFPYLDPFDSASQLMEPGRQSMDLVELVSLFPTLA GLAGLQVPPRCPVPSFHVELCREGKNLLKHFRFRDLEE DPYLPGNPRELIAYSQYPRPSDIPQWNSDKPSLKDIKIM GYSIRTIDYRYTVWVGFNPDEFLANFSDIHAGELYFVDS DPLQDHNMYNDSQGGDLFQLLMP | IDS |

REFERENCES

1. Arbabi-Ghahroudi, M., Desmyter, A., Wyns, L., Hamers, R., Muyldermans, S. (1997) *FEBS Lett* 414:521-6.
2. Baral, T. N., MacKenzie, R., Arbabi-Ghahroudi, M. (2013) *Curr Protoc Immunol* 103: Unit 2.17.
3. Bell, A., Wang, Z. J., Arbabi-Ghahroudi, M., Chang, T. A., Durocher, Y., Trojahn, U., Baardsnes, J., Jaramillo, M. L., Li, S., Baral, T. N., O'Connor-McCourt, M., MacKenzie, R., Zhang, J. (2010) *Cancer Lett* 289:81-90.
4. Chakravarthy, B., Ito, S., Atkinson, T., Gaudet, C., Ménard, M., Brown, L., Whitfield, J. (2014) *Biochem Biophys Res Commun* 445:656-60.
5. Chothia, C., Lesk, A. M. (1987) *J Mol Biol* 196:901-17.
6. Davies, J., Riechmann, L. (1996) *Immunotechnology* 2:169-79.
7. de Kruif, J., Logtenberg, T. (1996) *J Biol Chem* 271:7630-4.
8. Dumoulin, M., Conrath, K., Van Meirhaeghe, A., Meersman, F., Heremans, K., Frenken, L. G., Muyldermans, S., Wyns, L., Matagne, A. (2002) *Protein Sci* 11:500-15.
9. Durocher, Y., Perret, S., Kamen, A. (2002) *Nucleic Acids Res* 30:E9.
10. Hamers-Casterman, C., Atarhouch, T., Muyldermans, S., Robinson, G., Hamers, C., Songa, E. B., Bendahman, N., Hamers, R. (1993) *Nature* 363:446-8.
11. Haqqani, A. S., Caram-Salas, N., Ding, W., Brunette, E., Delaney, C. E., Baumann, E., Boileau, E., Stanimirovic, D. (2013) *Mol Pharm* 10:1542-56.
12. Hussack, G., Arbabi-Ghahroudi, M., van Faassen, H., Songer, J. G., Ng, K. K., MacKenzie, R., Tanha, J. (2011a) *J Biol Chem* 286:8961-76.
13. Hussack, G., Hirama, T., Ding, W., MacKenzie, R., Tanha, J. (2011b) *PLoS One* 6:e28218.
14. Iqbal, U., Trojahn, U., Albaghdadi, H., Zhang, J., O'Connor-McCourt, M., Stanimirovic D., Tomanek, B., Sutherland, G., Abulrob, A. (2010) *Br J Pharmacol* 160: 1016-28.
15. Jespers, L., Schon, O., James, L. C., Veprintsev, D., Winter G. (2004) *J Mol Biol* 337:893-903.
16. Kabat, E. A., Wu, T. T., (1991) *J Immunol* 147:1709-1719.
17. Kim, D. Y., Kandalaft, H., Ding, W., Ryan, S., van Faassen, H., Hirama, T., Foote, S. J., MacKenzie, R., Tanha, J. (2012) *Protein Eng Des Sel* 25:581-9.
18. Li, S., Zheng, W., Kuolee, R., Hirama, T., Henry, M., Makvandi-Nejad, S., Fjallman, T., Chen, W., Zhang, J. (2009) *Mol Immunol* 46:1718-26.
19. Magoč, T., Salzberg, S. L. (2011) *Bioinformatics* 27:2957-63.
20. Merritt, E. A., Hol, W. G. (1995) *Curr Opin Struct Biol* 5:165-71.
21. Murase, T., Eugenio, L., Schorr, M., Hussack, G., Tanha, J., Kitova, E. N., Klassen, J. S., Ng, K. K. (2014) *J Biol Chem* 289:2331-43.
22. Muruganandam, A., Tanha, J., Narang, S., Stanimirovic, D. (2002) *FASEB J* 16:240-2.

23. Nicaise, M., Valerio-Lepiniec, M., Minard, P., Desmadril, M. (2004) *Protein Sci* 13:1882-91.
24. Nielsen, U. B., Adams, G. P., Weiner, L. M., Marks, J. D. (2000) *Cancer Res* 60:6434-40.
25. Nuttall, S. D., Krishnan, U. V., Doughty, L., Pearson, K., Ryan, M. T., Hoogenraad, N. J., Hattarki, M., Carmichael, J. A., Irving, R. A., Hudson, P. J. (2003) *Eur J Biochem* 270:3543-54.
26. Ridgway, J. B., Presta, L. G., Carter, P. (1996) *Protein Eng* 9:617-21.
27. Schmieder, R., Edwards, R. (2011) *Bioinformatics* 27:863-4.
28. Spiess, C, Zhai, Q., Carter, P. J. (2015) *Mol Immunol* 67:95-106.
29. To, R., Hirama, T., Arbabi-Ghahroudi, M., MacKenzie, R., Wang, P., Xu, P., Ni, F., Tanha, J. (2005) *J Biol Chem* 280:41395-403.
30. Zhang, J., Tanha, J., Hirama, T., Khieu, N. H., To, R., Tong-Sevinc, H., Stone, E., Brisson, J. R., MacKenzie, C. R. (2004a) *J Mol Biol* 335:49-56.
31. Zhang, J., Li, Q., Nguyen, T. D., Tremblay, T. L., Stone, E., To, R., Kelly, J., MacKenzie C. R. (2004b) *J Mol Biol* 341:161-9.
32. Zhang, Y., Hou, M., Zhou, J., Xie, S. (2010) *Comput Methods Programs Biomed* 99:306-14.
33. Zhu, X., Wang, L., Liu, R., Flutter, B., Li, S., Ding, J., Tao, H., Liu, C., Sun, M., Gao, B. (2010) *Immunol Cell Biol* 88:667-75.

The invention claimed is:

1. An antibody or an antigen-binding fragment that binds to serum albumin comprising three complementarity determining regions (CDR1, CDR2 and CDR3), wherein said CDR1, CDR2 and CDR3 comprise an amino acid sequence comprising:

1)
```
                                         (SEQ ID NO: 1)
GFLLRSNTM, (SEQ ID NO: 2)
IRPSGLT,
and (SEQ ID NO: 3)
HTRPPFQRDS
or (SEQ ID NO: 4)
ATRPPFQRDS,
respectively; or
```

2)
```
                                         (SEQ ID NO: 5)
GRTFIAYAM, (SEQ ID NO: 6)
ITNFAGGTT,
and (SEQ ID NO: 7)
AADRSAQTMRQVRPVLPY,
respectively; or
```

3)
```
                                         (SEQ ID NO: 8)
GRTFDNYVM, (SEQ ID NO: 9)
ISGSGSIT,
and
```

```
                                        (SEQ ID NO: 10)
AAGSRRTYYREPKFYPS,
respectively; or 4)
                                        (SEQ ID NO: 11)
GSTFSSSSV, (SEQ ID NO: 12)
ITSGGST,
and (SEQ ID NO: 13)
NVAGRNWVPISRYSPGPY
or (SEQ ID NO: 14)
AVAGRNWVPISRYSPGPY,
respectively; or 5)
                                        (SEQ ID NO: 15)
GSIESINRM, (SEQ ID NO: 16)
ISKGGST,
and (SEQ ID NO: 17)
AAGPVWEQF,
respectively; or 6)
                                        (SEQ ID NO: 18)
GRTISLYAV, (SEQ ID NO: 19)
ISWTDSST,
and (SEQ ID NO: 20)
AADVSIRGLQKYEYDY,
respectively; or 7)
                                        (SEQ ID NO: 21)
TRTFSSYIM, (SEQ ID NO: 22)
ISWSGRMT,
and (SEQ ID NO: 23)
AADRTTAWGAPRSQYDS,
respectively.
```

2. The antibody or an antigen-binding fragment of claim 1, wherein said antigen-binding fragment is a single-domain antibody (sdAb).

3. The antibody or an antigen-binding fragment of claim 1, wherein said antibody is an IgA, IgD, IgE, IgG, or IgM.

4. The antibody or an antigen-binding fragment of claim 1, wherein said CDR1, CDR2 and CDR3 comprise an amino acid sequence comprising GFLLRSNTM (SEQ ID NO:1), IRPSGLT (SEQ ID NO:2), and HTRPPFQRDS (SEQ ID NO:3) or ATRPPFQRDS (SEQ ID NO:4), respectively.

5. The antibody or an antigen-binding fragment of claim 1, wherein said CDR1, CDR2 and CDR3 comprise an amino acid sequence comprising GRTFIAYAM (SEQ ID NO:5), ITNFAGGTT (SEQ ID NO:6), and AADRSAQTMRQVRPVLPY (SEQ ID NO:7), respectively.

6. The antibody or an antigen-binding fragment of claim 1, wherein said CDR1, CDR2 and CDR3 comprise an amino acid sequence comprising GRTFDNYVM (SEQ ID NO:8), ISGSGSIT (SEQ ID NO:9), and AAGSRRTYYREPKFYPS (SEQ ID NO:10), respectively.

7. The antibody or an antigen-binding fragment of claim 1, wherein said CDR1, CDR2 and CDR3 comprise an amino acid sequence comprising GSTFSSSSV (SEQ ID NO:11), ITSGGST (SEQ ID NO:12), and NVAGRNWVPISRYSPGPY (SEQ ID NO:13) or AVAGRNWVPISRYSPGPY (SEQ ID NO:14), respectively.

8. The antibody or an antigen-binding fragment of claim 1, wherein said CDR1, CDR2 and CDR3 comprise an amino acid sequence comprising GSIESINRM (SEQ ID NO:15), ISKGGST (SEQ ID NO:16), and AAGPVWEQF (SEQ ID NO:17), respectively.

9. The antibody or an antigen-binding fragment of claim 1, wherein said CDR1, CDR2 and CDR3 comprise an amino acid sequence comprising GRTISLYAV (SEQ ID NO:18), ISWTDSST (SEQ ID NO:19), and AADVSIRGLQKYEYDY (SEQ ID NO:20), respectively.

10. The antibody or an antigen-binding fragment of claim 1, wherein said CDR1, CDR2 and CDR3 comprise an amino acid sequence comprising TRTFSSYIM (SEQ ID NO:21), ISWSGRMT (SEQ ID NO:22), and AADRTTAWGAPRSQYDS (SEQ ID NO:23), respectively.

11. The antibody or an antigen-binding fragment of claim 1, wherein said antibody or an antigen-binding fragment is humanized.

12. A compound comprising an antibody or an antigen-binding fragment according to claim 1, and a peptide, a protein, or an enzyme.

13. The compound of claim 12, wherein said antibody or an antigen-binding fragment is linked to said compound via a linker sequence.

14. The compound of claim 13, wherein said is linker sequence is $(GGGGS)_n$ (SEQ ID NO:81), wherein n≥1.

15. The compound of claim 14, wherein said linker sequence is an amino acid sequence that allows for the functional linking of said compound to said antibody or an antigen-binding fragment.

16. The compound of claim 15, wherein said amino acid sequence comprises about 3 to about 40 amino acids.

17. The compound of claim 12, wherein said antibody or an antigen-binding fragment is fused to an antibody or an antigen-binding fragment, operable to bind a target epitope.

18. A method of removing a molecule from serum, comprising administering a compound according to claim 17 specific to said molecule, wherein said antibody or an antigen-binding fragment comprises CDR1, CDR2 and CDR3 comprising an amino acid sequence comprising GRTFDNYVM (SEQ ID NO:8), ISGSGSIT (SEQ ID NO:9), and AAGSRRTYYREPKFYPS (SEQ ID NO:10), respectively.

19. The compound of claim 12, wherein said antibody or an antigen-binding fragment is linked to a peptide, a polypeptide, a protein, an enzyme, an antibody, an antibody fragment, or combinations thereof, wherein each of said antibody or an antigen-binding fragment and said linked peptide, polypeptide, protein, enzyme, antibody, antibody fragment, or combinations thereof is functional.

20. A composition comprising the compound of claim 12, and a pharmaceutically acceptable diluent, carrier or excipient.

* * * * *